(12) United States Patent
Wager et al.

(10) Patent No.: US 7,115,600 B2
(45) Date of Patent: Oct. 3, 2006

(54) HISTAMINE-3 RECEPTOR MODULATORS

(75) Inventors: Travis T. Wager, New London, CT (US); Ramalakshmi Y. Chandrasekaran, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 93 days.

(21) Appl. No.: 11/045,968

(22) Filed: Jan. 28, 2005

(65) Prior Publication Data

US 2005/0171181 A1 Aug. 4, 2005

Related U.S. Application Data

(60) Provisional application No. 60/541,151, filed on Feb. 2, 2004.

(51) Int. Cl.
*A61K 31/496* (2006.01)
*A61K 31/541* (2006.01)
*A61K 31/4995* (2006.01)
*C07D 241/50* (2006.01)
*C07D 403/10* (2006.01)
*C07D 417/10* (2006.01)

(52) U.S. Cl. .................. 514/227.8; 514/249; 514/372; 544/60; 544/372; 544/349

(58) Field of Classification Search .................. 544/60, 544/372, 349
See application file for complete search history.

(56) References Cited

U.S. PATENT DOCUMENTS 5,541,343 A * 7/1996 Himmelsbach et al. ..... 514/424

* cited by examiner

*Primary Examiner*—Kamal A. Saeed
*Assistant Examiner*—Jason M. Nolan
(74) *Attorney, Agent, or Firm*—Steve T. Zelson; Jolene W. Appleman

(57) ABSTRACT

This invention is directed to a compound of the formula I

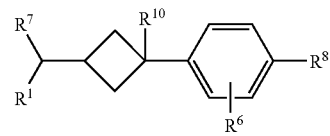

as defined herein, or a pharmaceutically acceptable salt thereof; a pharmaceutical composition containing a compound of formula I, a method of treatment of a disorder or condition that may be treated by modulating histamine H3 receptors, the method comprising administering to a mammal in need of such treatment a compound of formula I as described above, and a method of treatment of a disorder or condition selected from the group consisting of depression, mood disorders, schizophrenia, anxiety disorders, Alzheimer's disease, attention-deficit hyperactivity disorder (ADHD), psychotic disorders, sleep disorders, obesity, dizziness, epilepsy, motion sickness, respiratory diseases, allergy, allergy-induced airway responses, allergic rhinitis, nasal congestion, allergic congestion, congestion, hypotension, cardiovascular disease, diseases of the GI tract, hyper and hypo motility and acidic secretion of the gastro-intestinal tract, the method comprising administering to a mammal in need of such treatment a compound of formula I as described above.

22 Claims, No Drawings

HISTAMINE-3 RECEPTOR MODULATORS

The entire disclosure of parent application 60/541,151 filed Feb. 2, 2004 is fully incorporated herein by reference thereto.

BACKGROUND OF THE INVENTION

This invention is directed to compounds of formula I described herein, to pharmaceutical composition comprising such compounds, and to methods of treatment of disorders or conditions that may be treated by modulating histamine H3 receptors using such compounds.

Histamine is a well-known mediator in hypersensitive reactions, such as allergies, hay fever, and asthma, which are commonly treated with antagonists of histamine or "antihistamines." It has also been established that histamine receptors exist in at least two distinct types, referred to as H receptor, or HR, and H2 receptor, or H2R.

A third histamine receptor, the H3 receptor, is believed to play a role in neurotransmission in the central nervous system, where the H3 receptor is thought to be disposed presynaptically on histaminergic nerve endings (Nature, 302, S32-837 (1983)). The existence of the H3 receptor has been confirmed by the development of selective H3 receptor agonists and antagonists (Nature, 327, 117–123 (1987)) and has subsequently been shown to regulate the release of ther neurotransmitters in both the central nervous system and peripheral organs, particularly the lungs, cardiovascular system and gastrointestinal tract.

A number of diseases or conditions may be treated with histamine H3 receptor ligands wherein the H3 ligand may be an antagonist, inverse agonist, agonist or partial agonist, see: (Imamura et al., Circ. Res., (1996) 78, 475–481); (Imamura et. al., Circ. Res., (1996) 78, 863–869); (Lin et al., Brain Res. (1990) 523, 325–330); (Monti et al., Neuropsychopharmacology (1996) 15, 31 35); (Sakai, et al., Life Sci. (1991) 48, 2397–2404); (Mazurkiewiez-Kwilecki and Nsonwah, Can. J. Physiol. Pharmacol. (1989) 67, 75–78); (Panula, P. et al., Neuroscience (1998) 44, 465–481); (Wada et al., Trends in Neuroscience (1991) 14, 415); (Monti et al., Eur. J. Pharmacol. (1991) 205, 283); (Mazurkiewicz-Kwilecki and Nsonwah, Can. J. Physiol. Pharmacol. (1989) 67, 75–78); (Haas et al., Behav. Brain Res. (1995) 66, 41–44); (De Almeida and Izquierdo, Arch. Int. Pharmacodyn. (1986) 283, 193–198); (Kamei et al., Psychopharmacology (1990) 102, 312–318); (Kamei and Sakata, Jpn. J. Pharmacol. (199 1) 57, 437–482); (Schwartz et al., Psychopharmacology; The fourth Generation of Progress, Bloom and Kupfer (eds.), Raven Press, New York, (1995) 3 97); (Shaywitz et al., Psychopharmacology (1984) 82, 73–77); (Dumery and Blozovski, Exp. Brain Res. (1987) 67, 61–69); (Tedford et al., J. Pharmacol. Exp. Ther. (1995) 275, 598–604); (Tedford et al., Soc. Neurosci. Abstr. (1996) 22, 22); (Yokoyama et al., Eur. J. Pharmacol. (1993) 234, 129); (Yokoyama and Iinuma, CNS Drugs (1996) 5, 321); (Onodera et al., Prog. Neurobiol. (1994) 42, 685); (Leurs and Timmerman, Prog. Drug Res. (1992) 39, 127); (The Histamine H3 Receptor, Leurs and Timmerman (eds), Elsevier Science, Amsterdam, The Netherlands (1998); (Leurs et al., Trends in Pharm. Sci. (1998) 19, 177–183); (Phillips et al., Annual Reports in Medicinal Chemistry (1998) 33, 31–40); (Matsubara et al., Eur. J. Pharmacol. (1992) 224, 145); (Rouleau et al., J. Pharmacol. Exp. Ther. (1997) 281, 1085); (Adam Szelag, "Role of histamine H3-receptors in the proliferation of neoplastic cells in vitro", Med. Sci. Monit., 4(5): 747–755, (1998)); (Fitzsimons, C., H. Duran, F. Labombarda, B. Molinari and E. Rivera, "Histamine receptors signalling in epidermal tumor cell lines with H-ras gene alterations", Inflammation Res., 47 (Suppl. 1): S50–S51, (1998)); (R. Leurs, R. C. Vollinga and H. Timmerman, "The medicinal chemistry and therapeutic potentials of ligand of the histamine H3 receptor", Progress in Drug Research 45: 170–165, (1995)); (R. Levi and N. C. E. Smith, "Histamine H3-receptors: A new frontier in myocardial ischernia", J. Pharm. Exp. Ther., 292: 825–830, (2000)); (Hatta, E., K Yasuda and R. Levi, "Activation of histamine H3 receptors inhibits carrier-mediated norepinephrine release in a human model of protracted myocradial ischemia", J. Pharm. Exp. Ther., 283: 494–500, (1997); (H. Yokoyama and K. Iinuma, "Histamine and Seizures: Implications for the treatment of epilepsy", CNS Drugs, 5(5); 321–330, (1995)); (K. Hurukami, H. Yokoyama, K. Onodera, K. Iinuma and T. Watanabe, AQ-0 145, "A newly developed histamine H3 antagonist, decreased seizure susceptibility of eletrically induced convulsions in mice", Meth. Find. Exp. Clin. Pharmacol., 17(C): 70–73, (1995); (Delaunois A., Gustin P., Garbarg M., and Ansay M., "Modulation of acetylcholine, capsaicin and substance P effects by histamine H3 receptors in isolated perfused rabbit lungs", European Journal of Pharmacology 277(2–3): 243–50, (1995)); and (Dimitriadou, et al., "Functional relationship between mast cells and C-sensitive nerve fibres evidenced by histamine H3-receptor modulation in rat lung and spleen", Clinical Science 87(2): 151–63, (1994). Such diseases or conditions include cardiovascular disorders such as acute myocardial infarction; memory processes, dementia and cognition disorders such as Alzheimer's disease and attention-deficit hyperactivity disorder; neurological disorders such as Parkinson's disease, schizophrenia, depression, epilepsy, and seizures or convulsions; cancer such as cutaneous carcinoma," medullary thyroid carcinoma and melanoma; respiratory disorders such as asthma; sleep disorders such as narcolepsy; vestibular dysfunction such as Meniere's disease; gastrointestinal disorders, inflammation, migraine, motion sickness, obesity, pain, and septic shock.

H3 receptor antagonists have also been previously described in, for example, WO 03/050099, WO 02/0769252, and WO 02/12224. The histamine H3 receptor, or H3R, regulates the release of histamine and other neurotransmitters, including serotonin and acetylcholine. H3R is relatively neuron specific and inhibits the release of certain monoamines such as histamine. Selective antagonism of H3R raises brain histamine levels and inhibits such activities as food consumption while minimizing non-specific peripheral consequences. Antagonists of the receptor increase synthesis and release of cerebral histamine and other monoamines. By this mechanism, they induce a prolonged wakefulness, improved cognitive function, reduction in food intake and normalization of vestibular reflexes. Accordingly, the receptor is an important target for new therapeutics in Alzheimer disease, mood and attention adjustments, including attention deficit hyperactive disorder (ADHD), cognitive deficiencies, obesity, dizziness, schizophrenia, epilepsy, sleeping disorders, narcolepsy and motion sickness, and various forms of anxiety.

The majority of histamine H3 receptor antagonists to date resemble histamine in possessing an imidazole ring which may be substituted, as described, for example, in WO96/38142. Non-imidazole neuroactive compounds such as beta histamines (Arrang, Eur. J. Pharm. 1985, 111: 72–84) demonstrated some histamine H3 receptor activity but with poor potency. EP 978512 and EP 0982300A2 disclose non-imidazole alkylamines as histamine H3 receptor antagonists.

WO 00/06254 describes non-imidazole alkylamines as histamine-3 receptor ligands. Other receptor antagonists have been described in WO02/32893 and WO02/06233.

This invention is directed to histamine H3 receptor modulators, including antagonists and inverse agonists, useful for treating the conditions listed in the preceding paragraphs. The compounds of this invention are highly selective for the histamine H3 receptor vs. other histamine receptors, and possess remarkable drug disposition properties (pharmacokinetics). In particular, the compounds of this invention selectively distinguish H3R from the other receptor subtypes H1R, H2R. In view of the art's interest in histamine H3 receptor agonists, inverse agonists and antagonists, novel compounds which interact with the histamine H3 receptor would be a highly desirable contribution to the art. The present invention provides such a contribution to the art being based on the finding that a novel class of cyclobutyl aryl diamines has a high and specific affinity to the histamine H3 receptor.

SUMMARY OF THE INVENTION

This invention is directed to a compound of the formula I

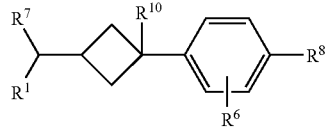

or a pharmaceutically acceptable salt thereof, wherein:
R$^1$ is selected from the group consisting of N$_3$, OR$^4$, and NR$^2$R$^3$;
R$^2$ and R$^3$ are each independently selected from the group consisting of hydrogen;
$C_1$–$C_8$ alkyl optionally substituted with 1 to 4 halogens;
$C_1$–$C_4$ alkyl group optionally substituted with a substituent selected from the group consisting of OH, one to four $C_1$–$C_4$ alkyl, $C_3$–$C_7$ cycloalkyl, $C_1$–$C_4$ dialkylamino, $C_6$–$C_{14}$ aryl optionally substituted with a halogen and optionally substituted with $C_6$–$C_{10}$ aryloxy optionally substituted with one to two halogens, and 5–10-membered heteroaryl optionally substituted with a $C_6$–$C_{10}$ aryl group and optionally substituted with one to three $C_1$–$C_4$ alkyl groups;
$C_3$–$C_7$ cycloalkyl;
$C_6$–$C_{14}$ aryl;
3–8-membered heterocycloalkyl optionally substituted with one or more $C_1$–$C_4$ alkyl-carbonyl group;
$C_6$–$C_{10}$ arylsulfonyl optionally substituted with one or more $C_1$–$C_2$ alkyl;
5–10-membered heteroaryl; and
$C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl;
wherein R$^3$ can be further selected from the group consisting of
$C_6$–$C_{14}$ arylcarbonyl-$C_6$–$C_{14}$ aryl; $C_6$–$C_{14}$ arylcarbonyl-3–8-membered heterocycloalkyl; $C_3$–$C_8$ cycloalkylcarbonyl-$C_6$–$C_{14}$ aryl; $C_3$–$C_8$ cycloalkylcarbonyl-3–8-membered heterocycloalkyl; 3–8-membered heterocycloalkylcarbonyl-$C_6$–$C_{14}$ aryl; and 3–8-membered heterocycloalkylcarbonyl-3–8-membered heterocycloalkyl;

or R$^3$ and R$^2$ together with the nitrogen of the NR$^2$R$^3$ group form a first 5-, 6-, or 7-membered aliphatic ring, wherein one of the carbons in the first 5-, 6-, or 7-membered aliphatic ring is optionally replaced by O, S, NR$^{2'}$, or CO, and the first 5-, 6-, or 7-membered aliphatic ring is optionally fused to a $C_6$–$C_{10}$ arylene and is optionally substituted at a ring carbon with a substituent selected from the group consisting of
5–10-membered heteroaryl optionally substituted with one or more halogens and optionally substituted with one or more $C_1$–$C_2$ alkyl,
$C_1$–$C_4$ alkoxy optionally substituted with one or more $C_1$–$C_2$ alkoxy and optionally substituted with one or more $C_1$–$C_4$ dialkylaminocarbonyl, and
one or two $C_1$–$C_4$ alkyl optionally and independently substituted with one or more $C_1$–$C_2$ alkoxy;
wherein R$^{2'}$ is
hydrogen;
$C_1$–$C_8$ alkyl optionally substituted with 1 to 4 halogens;
5–10-membered heteroaryl optionally substituted with a substituent selected from the group consisting of halogen, $C_1$–$C_4$ alkyl, $C_1$–$C_2$ alkoxy, $C_6$–$C_{10}$ aryl, $C_1$–$C_4$ alkylaminocarbonyl, and cyano;
$C_1$–$C_4$ alkyl group optionally substituted with a substituent selected from the group consisting of $C_1$–$C_2$ alkoxycarbonyl, 5–10-membered heteroaryl optionally substituted with one or more $C_1$–$C_2$ alkyl, one to four $C_1$–$C_4$ alkyl, $C_3$–$C_7$ cycloalkyl, and $C_6$–$C_{14}$ aryl;
$C_6$–$C_{10}$ aryl optionally substituted with one or two $C_1$–$C_2$ alkyl;
$C_1$–$C_4$ alkylcarbonyl;
or $C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl;
R$^4$ is
hydrogen;
$C_1$–$C_8$ alkyl optionally substituted with 1 to 4 halogens;
$C_1$–$C_4$ alkyl optionally substituted with a substituent selected from the group consisting of
$C_3$–$C_7$ cycloalkyl,
5–10-membered heteroaryl, and
$C_6$–$C_{14}$ aryl optionally substituted with a substituent selected from the group consisting of one, two or three halogens, cyano, one or two $C_1$–$C_2$ alkoxy, $C_1$–$C_2$ di- or tri-fluoroalkyl, $C_1$–$C_4$ alkyl optionally substituted with $C_6$–$C_{10}$ arylsulfonyl, nitro, and 5–10-membered heteroaryl;
5–10-membered heteroaryl optionally fused to a $C_6$–$C_{10}$ arylene group that is optionally substituted with one or more halogens or one or more $C_1$–$C_2$ alkoxy, wherein the 5–10-membered heteroaryl is optionally substituted with a substituent selected from the group consisting of:
$C_6$–$C_{10}$ aryl optionally substituted with one or more halogens, one or more $C_1$–$C_2$ alkoxy, or one or more $C_1$–$C_2$ alkyl;
$C_6$–$C_{10}$ arylcarbonyl optionally substituted with one or more halogens;
one or more halogens;
one to three $C_1$–$C_4$ alkyl groups optionally substituted with one or more $C_6$–$C_{10}$ aryl optionally and independently substituted with one or more halogens or one or more $C_1$–$C_2$ alkoxy;
$C_1$–$C_2$ di- or tri-fluoroalkyl;
1 to 2 $C_1$–$C_2$ alkoxy groups;
3–8-membered heterocycloalkyl;
5–10-membered heteroarylamino;

$C_1–C_2$ alkylaminocarbonyl-$C_1–C_2$-alkylamino;

$C_6–C_{10}$ arylaminocarbonyl;

$C_6–C_{10}$ arylaminocarbonyl-$C_1–C_2$-alkylamino optionally substituted with one or more halogens at the $C_6–C_{10}$ aryl moiety of $C_6–C_{10}$ arylaminocarbonyl;

5–10-membered heteroaryl optionally substituted with one or more $C_6–C_{10}$ aryl or one or more $C_1–C_2$ alkyl;

$C_6–C_{10}$ aryloxy optionally substituted with one or more $C_1–C_2$ alkoxy or one or more halogens; and $C_1–C_4$ dialkylamino;

$C_6–C_{14}$ aryl optionally substituted with one or more halogens and optionally substituted with one or more $C_6–C_{10}$ aryloxy optionally and independently substituted with one to two halogens;

$C_6–C_{14}$ aryl-$C_0–C_4$ alkylene-O—$C_0–C_4$ alkyl, wherein each $C_0–C_4$ alkyl and each $C_0–C_4$ alkylene is optionally substituted with one to four $C_1–C_4$ alkyl; or $C_6–C_{10}$ arylsulfonyl optionally substituted with $C_1–C_2$ alkyl;

$R^6$ is hydrogen, $C_1–C_4$ alkyl or halogen;

$R^7$ is hydrogen, $SO_2C_1–C_{10}$ alkyl, $C_1–C_8$ alkyl optionally substituted with 1 to 4 halogens, $C_3–C_7$ cycloalkyl-$C_0–C_4$ alkyl, $C_6–C_{14}$ aryl-$C_0–C_4$ alkyl, 5–10-membered heteroaryl-$C_0–C_4$ alkyl, or $C_6–C_{14}$ aryl-$C_0–C_4$ alkylene-O—$C_0–C_4$ alkyl, wherein each $C_0–C_4$ alkyl and each $C_0–C_4$ alkylene is optionally substituted with one to four $C_1–C_4$ alkyl;

$R^{10}$ is OH, halogen or hydrogen;

$R^8$ is CN, —$CHR^7NR^{2''}R^{3''}$ or $C(=NR^{12})$—$NR^{13}R^{13'}$, wherein $R^{13}$ and $R^{13'}$ are each independently hydrogen or $C_1–C_6$ alkyl and $R^{12}$ is hydrogen, $C_1–C_6$ alkyl OH, O—$C_1–C_6$ alkyl, $NH_2$, $NHC_1–C_6$ alkyl, or $N(C_1–C_6$ alkyl$)_2$, or wherein $C(=NR^{12})$—$NR^{13}R^{13'}$ represents a five-membered heteroaryl group, wherein $R^{12}$ is O, NH, or $NC_1–C_6$ alkyl, $R^{13}$ and $R^{13'}$ taken together represent N or $CR^{13''}$ double bonded to the nitrogen of the $NR^{13}R^{13'}$ group, and $R^{13''}$ is hydrogen or $C_1–C_6$ alkyl;

or when $R^8$ is ortho to $R^6$, $R^6$ and $R^8$ together with the carbons of the aromatic ring to which $R^6$ and $R^8$ are attached may form a 5-membered carbocyclic ring;

$R^{2''}$ is hydrogen, $C_1–C_8$ alkyl optionally substituted with 1 to 4 halogens, $C_3–C_7$ cycloalkyl-$C_0–C_4$ alkyl, $C_6–C_{14}$ aryl-$C_0–C_4$ alkyl, 5–10-membered heteroaryl-$C_0–C_4$ alkyl, or $C_6–C_{14}$ aryl-$C_0–C_4$ alkylene-O—$C_0–C_4$ alkyl, wherein each $C_0–C_4$ alkyl and each $C_0–C_4$ alkylene is optionally substituted with one to four $C_1–C_4$ alkyl;

$R^{3''}$ is hydrogen, $C_1–C_8$ alkyl optionally substituted with 1 to 4 halogens, $C_6–C_{14}$ aryl, $C_6–C_{14}$ arylcarbonyl-$C_6–C_{14}$ aryl, $C_6–C_{14}$ arylcarbonyl-3–8-membered heterocycloalkyl, $C_3–C_8$ cycloalkylcarbonyl-$C_6–C_{14}$ aryl, $C_3–C_8$ cycloalkylcarbonyl-3–8-membered heterocycloalkyl, 3–8-membered heterocycloalkyl, 3–8-membered heterocycloalkylcarbonyl-$C_6–C_{14}$ aryl, or 3–8-membered heterocycloalkylcarbonyl-3–8-membered heterocycloalkyl;

or $R^{3''}$ and $R^{2''}$ together with the nitrogen of the $CHR^7NR^{2''}R^{3''}$ group form a second 5-, 6- or 7-membered aliphatic ring, wherein one of the carbons in the second 5-, 6-, or 7-membered aliphatic ring is optionally replaced by O, S, $NR^{11}$, or C=O and the second 5-, 6-, or 7-membered aliphatic ring is optionally substituted with one or two $C_1–C_4$ alkyl or optionally substituted with OH, wherein $R^{11}$ is hydrogen, $C_1–C_8$ alkyl optionally substituted with 1 to 4 halogens, $C_3–C_7$ cycloalkyl-$C_0–C_4$ alkyl, $C_6–C_{14}$ aryl-$C_0–C_4$ alkyl, 5–10-membered heteroaryl-$C_0–C_4$ alkyl, or $C_6–C_{14}$ aryl-$C_0–C_4$ alkylene-O—$C_0–C_4$ alkyl, wherein each $C_0–C_4$ alkyl and each $C_0–C_4$ alkylene is optionally substituted with one to four $C_1–C_4$ alkyl; and $R^{7'}$ is hydrogen, $C_1–C_8$ alkyl optionally substituted with 1 to 4 halogens, $C_3–C_7$ cycloalkyl-$C_0–C_4$ alkyl, $C_6–C_{14}$ aryl-$C_0–C_4$ alkyl, 5–10-membered heteroaryl-$C_0–C_4$ alkyl, $C_6–C_{14}$ aryl-$C_0–C_4$ alkylene-O—$C_0–C_4$ alkyl, wherein each $C_0–C_4$ alkyl and each $C_0–C_4$ alkylene is optionally substituted with one to four $C_1–C_4$ alkyl, or $SO_2C_1–C_{10}$ alkyl.

This invention is also directed to:

a pharmaceutical composition for treating, for example, a disorder or condition that may be treated by modulating histamine H3 receptors, the composition comprising a compound of formula I as described above, and optionally a pharmaceutically acceptable carrier;

a method of treatment of a disorder or condition that may be treated by modulating histamine H3 receptors, the method comprising administering to a mammal in need of such treatment a compound of formula I as described above; and a pharmaceutical composition for treating, for example, a disorder or condition selected from the group consisting of depression, mood disorders, schizophrenia, anxiety disorders, Alzheimer's disease, attention-deficit hyperactivity disorder (ADHD), psychotic disorders, sleep disorders, obesity, dizziness, epilepsy, motion sickness, respiratory diseases, allergy, allergy-induced airway responses, allergic rhinitis, nasal congestion, allergic congestion, congestion, hypotension, cardiovascular disease, diseases of the GI tract, hyper and hypo motility and acidic secretion of the gastro-intestinal tract, the composition comprising a compound of formula I as described above, and optionally a pharmaceutically acceptable carrier.

This invention is also directed to a method of treatment of a disorder or condition selected from the group consisting of the disorders or conditions listed herein, the method comprising administering to a mammal in need of such treatment a compound of formula I as described above.

The invention is also directed to a composition comprising a compound of formula I, a histamine $H_1$ antagonist, and optionally a pharmaceutically acceptable carrier.

The invention is also directed to a method of treatment of a condition selected from the group consisting of allergic rhinitis, nasal congestion, and allergic congestion in a mammal, the method comprising administering a compound of formula I and a histamine $H_1$ antagonist to a mammal in need of such treatment.

The invention is also directed to a composition comprising a compound of formula I, a neurotransmitter re-uptake blocker and optionally a pharmaceutically acceptable carrier.

The invention is also directed to a method of treatment of a condition selected from the group consisting of depression, mood disorders and schizophrenia in a mammal, the method comprising administering a compound of formula I and a neurotransmitter re-uptake blocker to a mammal in need of such treatment.

The pharmaceutical composition and method of this invention may also be used for preventing a relapse in a disorder or condition described in the previous paragraphs. Preventing such relapse is accomplished by administering to a mammal in need of such prevention a compound of formula I as described above and is contemplated as a method of treatment.

DETAILED DESCRIPTION OF THE INVENTION

The compound of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

Isotopically-labeled compounds of formula I, including compounds of formula I isotopically-labeled to be detectable by PET or SPECT, are also within the scope of the invention.

Cis and trans isomers of the inventive compound of formula I are also within the scope of the invention.

When a first group or substituent is substituted by two or more groups or substituents, the invention includes without limitation embodiments in which a combination of such groups or substituents is present. For example, a 5–10-membered heteroaryl optionally substituted with a substituent selected from the group consisting of "halogen, $C_1$–$C_4$ alkyl, $C_1$–$C_2$ alkoxy, $C_6$–$C_{10}$ aryl, $C_1$–$C_4$ alkylaminocarbonyl, and cyano" is a 5–10-membered heteroaryl which may be substituted with any of the substituents within the quotation marks or with a combination of the substituents within the quotation marks.

When a first group or substituent is substituted by two or more groups or substituents, it is understood that the number of such substituents may not exceed the number of positions in the first group or substituent that are available for substitution.

The term "alkyl" refers to straight or branched chains of carbon atoms. Exemplary alkyl groups are $C_1$–$C_6$ saturated alkyl groups, which include methyl, ethyl, propyl, isopropyl, butyl, isobutyl, pentyl, isopentyl, hexyl, and the like, including all regioisomeric forms thereof, and straight and branched chain forms thereof. The term "alkyl" is also used to denote straight or branched chains of carbon atoms having one or more carbon-carbon double bonds, such as vinyl, allyl, butenyl, and the like, as well as straight or branched chains of carbon atoms having one or more carbon-carbon triple bonds, such as ethynyl, propargyl, butynyl, and the like. The term "aryl" denotes a cyclic, aromatic hydrocarbon. Examples of aryl groups include phenyl, naphthyl, anthracenyl, phenanthrenyl, and the like. The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon-carbon double bonds in the ring. Examples of cycloalkyl groups include cyclopropyl, cyclobutyl, cyclopentyl, cyclohexyl, cycloheptyl, and the like, as well as cyclopentenyl, cyclopentadienyl, cyclohexenyl, cyclohexadienyl, cyclobutadienyl, and the like. As used herein, the term "cycloalkyl" is also intended to denote a cyclic group comprising at least two fused rings, such as adamantanyl, decahydronaphthalinyl, norbornanyl, where the cyclic group may also have one or more carbon-carbon double bonds in one or both rings, such as in bicyclo[4.3.0]nona-3,6(1)-dienyl, dicyclopentadienyl, 1,2,3,4-tetrahydronaphthalinyl (tetralinyl), indenyl, and the like. The term "halogen" represents chloro, fluoro, bromo, and iodo. The term "heteroaryl" denotes a monocyclic or bicyclic aromatic group wherein one or more carbon atoms are replaced with heteroatoms selected from the group consisting of nitrogen, oxygen, and sulfur. If the heteroaryl group contains more than one heteroatom, the heteroatoms may be the same or different. Preferred heteroaryl groups are five- and six-membered rings that contain from one to three heteroatoms independently selected from oxygen, nitrogen, and sulfur. Examples of preferred five- and six-membered heteroaryl groups include benzo[b]thienyl, chromenyl, furyl, imidazolyl, indazolyl, indolizinyl, indolyl, isobenzofuranyl, isoindolyl, isoquinolyl, isothiazolyl, isoxazolyl, naphthyridinyl, oxadiazolyl, oxazinyl, oxazolyl, phthalazinyl, pteridinyl, purinyl, pyranyl, pyrazinyl, pyrazolyl, pyridazinyl, pyridyl, pyrimidyl, pyrrolyl, quinolizinyl, quinolyl, quinoxalinyl, thiazolyl, thienyl, triazinyl, triazolyl, and xanthenyl.

The term "heterocycloalkyl" denotes a cycloalkyl system, wherein "cycloalkyl" is defined above, in which one or more of the ring carbon atoms are replaced with a heteroatom selected from the group consisting of nitrogen, oxygen, and sulfur. Examples of such heterocycloalkyl groups include azabicycloheptanyl, azetidinyl, benzazepinyl, 1,3-dihydroisoindolyl, indolinyl, tetrahydrofuryl, tetrahydroquinolinyl, tetrahydroisoquinolinyl, morpholinyl, piperazinyl, piperidyl, pyrrolidinyl, and, tetrahydro-2H-1,4-thiazinyl.

A cyclic group may be bonded to another group in more than one way. If no particular bonding arrangement is specified, then all possible arrangements are intended. For example, the term "pyridyl" includes 2-, 3-, or 4-pyridyl, and the term "thienyl" includes 2- or 3-thienyl.

The term "$C_0$–$C_4$" includes the embodiment where there are no carbons in a chain. Thus, for example, the groups "$C_3$–$C_7$ cycloalkyl-$C_0$–$C_4$ alkyl," "$C_6$–$C_{14}$ aryl-$C_0$–$C_4$ alkyl," "5–10-membered heteroaryl-$C_0$–$C_4$ alkyl," and "$C_6$–$C_{14}$ aryl-$C_0$–$C_4$ alkylene-O—$C_0$–$C_4$ alkyl" include $C_3$–$C_7$ cycloalkyl, $C_6$–$C_{14}$ aryl, 5–10-membered heteroaryl, and $C_6$–$C_{14}$ aryl-O—$C_0$–$C_4$ alkyl, respectively.

The term "$C_1$–$C_4$ dialkylamino" refers to a dialkylamino group in which each alkyl group is independently a $C_1$–$C_4$ alkyl group.

"Modulating histamine H3 receptors," as used herein, refers to acting as a histamine H3 receptor modulator. Examples of histamine H3 receptor modulators include histamine H3 receptor antagonists and histamine H3 receptor inverse agonists. Similarly, "modulating histamine H3 receptors," includes acting as a histamine H3 receptor antagonist and includes acting as a histamine H3 receptor inverse agonist.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The histamine H3 receptor modulators of the invention are useful for treating, in particular, ADHD, obesity, anxiety disorders and respiratory diseases. Respiratory diseases that may be treated by the present invention include adult respiratory distress syndrome, acute respiratory distress syndrome, bronchitis, chronic bronchitis, chronic obstructive pulmonary disease, cystic fibrosis, asthma, emphysema, rhinitis and chronic sinusitis.

Anxiety disorders include, for example, generalized anxiety disorder, panic disorder, PTSD, and social anxiety disorder. Mood adjustment disorders include, for example, depressed mood, mixed anxiety and depressed mood, disturbance of conduct, and mixed disturbance of conduct and depressed mood. Attention adjustment disorders include, for example, in addition to ADHD, attention-deficit disorders or other cognitive disorders due to general medical conditions.

Psychotic disorders include, for example, schizoaffective disorders and schizophrenia; sleep disorders include, for example, narcolepsy and enuresis.

Examples of the disorders or conditions which may be treated by the compound, composition and method of this invention are also as follows: depression, including, for example, depression in cancer patients, depression in Parkinson's patients, Postmyocardial Infarction depression, depression in patients with human immunodeficiency virus (HIV), Subsyndromal Symptomatic depression, depression in infertile women, pediatric depression, major depression, single episode depression, recurrent depression, child abuse induced depression, post partum depression, DSM-IV major depression, treatment-refractory major depression, severe depression, psychotic depression, post-stroke depression, neuropathic pain, manic depressive illness, including manic depressive illness with mixed episodes and manic depressive illness with depressive episodes, seasonal affective disorder, bipolar depression BP I, bipolar depression BP II, or major depression with dysthymia; dysthymia; phobias, including, for example, agoraphobia, social phobia or simple phobias; eating disorders, including, for example, anorexia nervosa or bulimia nervosa; chemical dependencies, including, for example, addictions to alcohol, cocaine, amphetamine and other psychostimulants, morphine, heroin and other opioid agonists, phenobarbital and other barbiturates, nicotine, diazepam, benzodiazepines and other psychoactive substances; Parkinson's diseases, including, for example, dementia in Parkinson's disease, neuroleptic-induced parkinsonism or tardive dyskinesias; headache, including, for example, headache associated with vascular disorders; withdrawal syndrome; age-associated learning and mental disorders; apathy; bipolar disorder; chronic fatigue syndrome; chronic or acute stress; conduct disorder; cyclothymic disorder; somatoform disorders such as somatization disorder, conversion disorder, pain disorder, hypochondriasis, body disphormic disorder, undifferentiated disorder, and somatoform NOS; incontinence; inhalation disorders; intoxication disorders; mania; oppositional defiant disorder; peripheral neuropathy; post-traumatic stress disorder; late luteal phase dysphoric disorder; specific developmental disorders; SSRI "poop out" syndrome, or a patient's failure to maintain a satisfactory response to SSRI therapy after an initial period of satisfactory response; and tic disorders including Tourette's disease.

As used herein, "mammal" is any member of the class mammalia. As an example, the mammal, in need of the treatment or prevention may be a human. As another example, the mammal in need of the treatment or prevention may be a mammal other than a human.

A compound of formula I which is basic in nature is capable of forming a wide variety of different salts with various inorganic and organic acids. The acid addition salts are readily prepared by treating the base compounds with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid salts of the active compound used in formulating the pharmaceutical composition of this invention that are basic in nature are those which form non-toxic acid addition salts, i.e., salts containing pharmacologically acceptable anions. Non-limiting examples of the salts include the acetate, benzoate, .beta.-hydroxybutyrate, bisulfate, bisulfite, bromide, butyne-1,4-dioate, carpoate, chloride, chlorobenzoate, citrate, dihydrogenphosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methbxybenzoate, methylbenzoate, monohydrogenphosphate, naphthalene-1-sulfonate, naphthalene-2-sulfonate, oxalate, phenylbutyrate, phenylproionate, phosphate, phthalate, phylacetate, propanesulfonate, propiolate, propionate, pyrophosphate, pyrosulfate, sebacate, suberate, succinate, sulfate, sulfite, sulfonate, tartrate, xylenesulfonate, acid phosphate, acid citrate, bitartrate, succinate, gluconate, saccharate, nitrate, methanesulfonate and pamoate [i.e., 1,1'-methylene-bis-(2-hydroxy-3-naphthoate)] salts.

In a preferred embodiment of the composition of the invention comprising a compound of formula I, a histamine $H_1$ antagonist, and optionally a pharmaceutically acceptable carrier, the combined amounts of the compound of formula I and of the histamine $H_1$ antagonist are effective in the treatment of the condition selected from the group consisting of allergic rhinitis, nasal congestion, and allergic congestion. In exemplary embodiments of the composition, histamine $H_1$ antagonists include loratidine (Claritin™), desloratidine (Clarinex™), fexofenadin (Allegra™) and cetirizine (Zyrtec™).

In a preferred embodiment of the composition of the invention comprising a compound of formula I, a neurotransmitter re-uptake blocker and optionally a pharmaceutically acceptable carrier, the combined amounts of the compound of formula I and of the neurotransmitter re-uptake blocker are effective in the treatment of the condition selected from the group consisting of depression, mood disorders and schizophrenia. Exemplary neurotransmitter re-uptake blockers include selective serotonin re-uptake inhibitors (SSRIs) or non-selective serotonin, dopamine, or norepinephrine reuptake inhibitors, including fluoxetine (Prozac™); sertraline (Zoloft™), described in U.S. Pat. No. 4,536,518 assigned to Pfizer Inc., incorporated by reference herein; paroxetine (Paxil™); and ziprasidone (Geodon™), described in U.S. Pat. Nos. 4,831,031, 4,883,795, and 6,245,766, incorporated by reference herein.

Exemplary embodiments of the present invention include the compound of formula I in which
(A) $R^{10}$ is hydrogen, F or OH;
(B) $R^6$ is hydrogen;
(C) $R^7$ is hydrogen or $C_1$–$C_6$ alkyl, such as methyl;
(D) $R^8$ is $CHR^{7'}NR^{2'''}R^{3'''}$ preferably wherein $R^{7'}$ is hydrogen and $R^{3'''}$ and $R^{2'''}$ together with the nitrogen of the $CHR^{7'}NR^{2'''}R^{3'''}$ group form a second 5-, 6- or 7-membered aliphatic ring, wherein one of the carbons in the second 5-, 6-, or 7-membered aliphatic ring is optionally replaced by O, S, $NR^{11}$, or C=O and the second 5-, 6-, or 7-membered aliphatic ring is optionally substituted with one or two $C_1$–$C_4$ alkyl or optionally substituted with OH, wherein $R^{11}$ is hydrogen, $C_1$–$C_8$ alkyl optionally substituted with 1 to 4 halogens, $C_3$–$C_7$ cycloalkyl-$C_0$–$C_4$ alkyl, $C_6$–$C_{14}$ aryl-$C_0$–$C_4$ alkyl, 5–10-membered heteroaryl-$C_0$–$C_4$ alkyl, or $C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl; and most preferably wherein $R^{7'}$ is hydrogen and $R^{3'''}$ and $R^{2'''}$ together with the nitrogen of the $CHR^{7'}NR^{2'''}R^{3'''}$ group form a pyrrolidinyl, morpholinyl, 3-hydroxypyrrolidinyl, or piperidinyl group;
or wherein $R^{7'}$ is hydrogen and $R^{3'''}$ and $R^{2'''}$ are each the same or a different $C_1$–$C_4$ alkyl group, such as a methyl group for each of $R^{3'''}$ and $R^{2'''}$; or or wherein $R^{7'}$ is hydrogen or $C_1$–$C_6$ alkyl, such as methyl; and/or (E) $R^1$ is selected from the group consisting of a) $NR^2R^3$, wherein $R^2$ and $R^3$ are each independently selected from the group consisting of $C_1$–$C_4$ alkyl optionally substituted with a substituent selected from the group consisting of OH, $C_3$–$C_7$ cycloalkyl, $C_1$–$C_4$ dialkylamino, $C_6$–$C_{14}$ aryl optionally substituted with one or more halogens and optionally substituted with $C_6$–$C_{10}$ aryloxy optionally substituted with one to two halogens, and 5–10-membered heteroaryl optionally substituted with a $C_6$–$C_{10}$ aryl group and optionally substituted with one to three $C_1$–$C_4$ alkyl groups;

$C_3$–$C_7$ cycloalkyl;

3–8-membered heterocycloalkyl optionally substituted with one or more $C_1$–$C_4$ alkylcarbonyl groups; and $C_6$–$C_{10}$ arylsulfonyl optionally substituted with one or more $C_1$–$C_2$ alkyl;

or $R^3$ and $R^2$ together with the nitrogen of the $NR^2R^3$ group form a first 5, 6, or 7-membered aliphatic ring, wherein one of the carbons in the first 5, 6, or 7-membered aliphatic ring is optionally replaced by O, S, $NR^{2'}$, or CO, and the first 5, 6, or 7-membered aliphatic ring is optionally fused to a $C_6$–$C_{10}$ arylene and is optionally substituted at a ring carbon with a substituent selected from the group consisting of 5–10-membered heteroaryl optionally substituted with one or more halogens and optionally substituted with one or more $C_1$–$C_2$ alkyl, $C_1$–$C_4$ alkoxy optionally substituted with one or more $C_1$–$C_2$ alkoxy and optionally substituted with one or more $C_1$–$C_4$ dialkylaminocarbonyl, and one or two C1-C4 alkyl optionally and independently substituted with one or more $C_1$–$C_2$ alkoxy;

wherein $R^{2'}$ is

5–10-membered heteroaryl optionally substituted with a substituent selected from the group consisting of halogen, $C_1$–$C_4$ alkyl, $C_1$–$C_2$ alkoxy, $C_6$–$C_{10}$ aryl, $C_1$–$C_4$ alkylaminocarbonyl, and cyano;

$C_1$–$C_4$ alkyl optionally substituted with a substituent selected from the group consisting of $C_1$–$C_2$ alkoxycarbonyl and 5–10-membered heteroaryl optionally substituted with one or more $C_1$–$C_2$ alkyl;

$C_6$–$C_{10}$ aryl optionally substituted with one or two $C_1$–$C_2$ alkyl;

or $C_1$–$C_4$ alkylcarbonyl;

preferably wherein $R^2$ and $R^3$ are each independently $C_1$–$C_4$ alkyl, or $R^3$ and $R^2$ together with the nitrogen of the $NR^2R^3$ group form a first 5, 6, or 7-membered aliphatic ring, wherein one of the carbons in the first 5, 6, or 7-membered aliphatic ring is optionally replaced by O, S, $NR^{2'}$, or CO wherein $R^{2'}$ is $C_1$–$C_4$ alkyl; more preferably wherein $R^3$ and $R^2$ together with the nitrogen of the $NR^2R^3$ group form a pyrrolidinyl, morpholinyl, 3-hydroxypyrrolidinyl, or piperidinyl group;

b) $OR^4$, wherein $R^4$ is $C_1$–$C_4$ alkyl optionally substituted with $C_6$–$C_{14}$ aryl optionally substituted with a substituent selected from the group consisting of one, two or three halogens, cyano, one or two $C_1$–$C_2$ alkoxy, $C_1$–$C_2$ di- or tri-fluoroalkyl, and $C_1$–$C_4$ alkyl optionally substituted with $C_6$–$C_{10}$ arylsulfonyl, nitro, or 5–10-membered heteroaryl;

5–10-membered heteroaryl optionally fused to a $C_6$–$C_{10}$ arylene group that is optionally substituted with one or more halogens or one or more $C_1$–$C_2$ alkoxy, wherein the 5–10-membered heteroaryl is optionally substituted with a substituent selected from the group consisting of:

$C_6$–$C_{10}$ aryl optionally substituted with one or more halogens, one or more $C_1$–$C_2$ alkoxy, or one or more $C_1$–$C_2$ alkyl;

$C_6$–$C_{10}$ arylcarbonyl optionally substituted with one or more halogens;

one or more halogens;

one to three $C_1$–$C_4$ alkyl groups optionally substituted with one or more $C_6$–$C_{10}$ aryl optionally substituted with one or more halogens or one or more alkoxy;

$C_1$–$C_2$ di- or tri-fluoroalkyl;

one or two $C_1$–$C_2$ alkoxy groups;

3–8-membered heterocycloalkyl;

5–10-membered heteroaryl-amino;

$C_1$–$C_2$ alkylaminocarbonyl-$C_1$–$C_2$-alkylamino;

$C_6$–$C_{10}$ arylaminocarbonyl;

$C_6$–$C_{10}$ arylaminocarbonyl-$C_1$–$C_2$-alkylamino optionally substituted with one or more halogens at the $C_6$–$C_{10}$ aryl moiety of $C_6$–$C_{10}$ arylaminocarbonyl;

5–10-membered heteroaryl optionally substituted with one or more $C_6$–$C_{10}$ aryl or one or more $C_1$–$C_2$alkyl;

$C_6$–$C_{10}$ aryloxy optionally substituted with one or more $C_1$–$C_2$ alkoxy or one or more halogens; and $C_1$–$C_4$ dialkylamino; or $C_6$–$C_{10}$ arylsulfonyl optionally substituted with $C_1$–$C_2$ alkyl;

preferably wherein $R^1$ is $OR^4$, wherein $R^4$ is $C_1$–$C_4$ alkyl and c) $N_3$.

Exemplary embodiments of the present invention also include any combination of the foregoing embodiments (A)–(E).

Exemplary compounds of formula (I) according to the invention may be prepared by Scheme 1:

Scheme 1

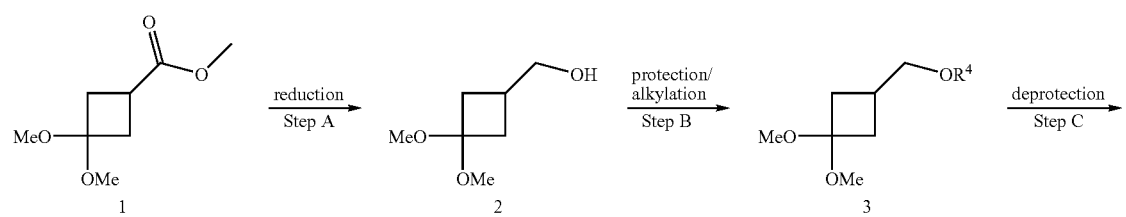

-continued

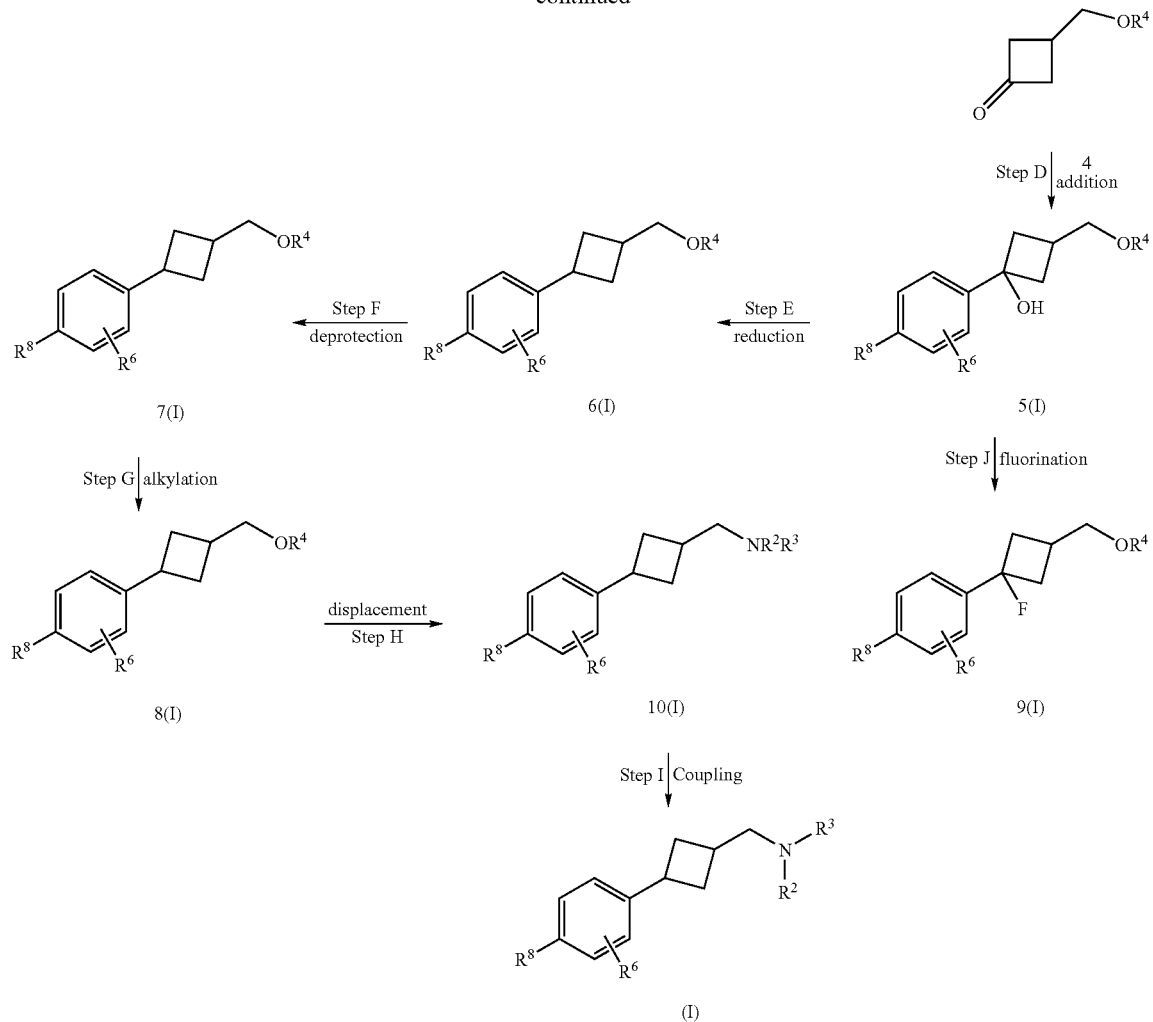

In Scheme 1, compounds of the formula (I) are prepared as follows.

Step A:

The compounds of the general formula (I) are synthesized from 3,3-dimethoxy-cyclobutanecarboxylic acid methyl ester, (1) (J. Org. Chem. 1988, 53, 3841 and J. Org. Chem. 1996, 61, 2174). The ester (1) is reduced with an appropiate reduction reagent such as e.g. lithium aluminum hydride, or sodium borohydride and aluminum trichloride in diglyme. The reaction is normally effected in an aprotic solvent, such as tetrahydrofuran, or diethyl ether at a reaction temperature below from about 0 C to the reflux temperature of the solvent employed, yielding the alcohol (2).

Step B:

The protecting group of alcohol (2) may be chosen from the protective groups known in the art and described in the literature (e.g. T. W Greene; P. G. Wuts, Protective Groups in Organic Synthesis, 3$^{rd}$ edition, John Wiley&Sons Inc. New York, 1999). For example protection/alkylation of alcohol (2) can be accomplished by reaction of (2) in a reaction inert solvent such as tetrahydrofuran, with a base, i.e. sodium hydride, potassium t-butoxide and with alkyl halide for example benzyl bromide, or sulfunyl chloride, for example p-toluenesulfonyl chloride to give an ether or tosylate, respectively (3).

Step C:

The ketal protection group of (3) is removed by methods known in the art (e.g. T. W Greene; P. G. Wuts, Protective Groups in Organic Synthesis, 3$^{rd}$ edition, John Wiley&Sons Inc. New York, 1999). The preferred method of ketal removal is by reaction of (3) in acetone, with an acid, such as hydrogen chloride, p-toluenesulfonic acid monohydrate, or pyridinium p-toluenesulfonate, at a temperature between about room temperature and about the relux temperature of the solvent employed to give ketone (4).

Step D:

The ketone (4) is reacted with an aryl bromide in the presence of an organometallic reagent, such as an organolithium, organomagnesium halide, organocerium, organotitanium, organozinc, organocopper, or organolaluminum reagent to form alcohol (5). An organomagnesium halide (Grignard reagent) or organolithium reagent is preferred. The reaction is typically effected in a reaction-inert-solvent, such as tetrahydrofuran, at a temperature between about −78° C. and about room temperature to yield (5) a compound of fomula (I).

Step E:

Reduction of the benzyl alcohol (5) is accomplished by reaction of (5) with an acid, preferable with trifluoroacetic acid, either neat or in a reaction-inert-solvent, such as methylene chloride or 1,2-dichloroethane and in the the presence of a reducing reagent such as a silane, preferable triethylsilane, triisopropylsilane, or triphenylsilane at a reaction temperature from about room temperature to the reflux temperature of the solvent employed, where about 65° C. is the preferred reaction temperature, yields (6) a compound of formula (I).

Step F:

When $R^4$ of (6) is a protection group this group is removed by methods known in the art (e.g. T. W Greene; P. G. Wuts, Protective Groups in Organic Synthesis, $3^{rd}$ edition, John Wiley&Sons Inc. New York, 1999). For example, when the protection group is a benzyl ether, the preferred method of removal is by reaction of (6) under standard hydrogenation conditions, preferable using palladium black in the presence of hydrogen, at a pressure of around 45 psi in ethyl alcohol or ethyl acetate yields (7) a compound of formula (I). In the case where the protection group is a tosylate, the preferred method of removal is by reaction of (6) in a protic solvent, preferable methanol with magnesium metal at room temperature to give (7) a compound of formula (I).

Step G:

The compound of the type (7) is treated with a base, i.e. sodium hydride, potassium t-butoxide, triethyl amine in a reaction-inert-solvent where preferred solvent is tetrahydrofuran and with an alkyl halide, heteroaryl halide, acid chloride, or sulfonyl chloride, such as, for example, benzyl bromide, 2-bromopyridine, acetyl chloride, or p-toluensulfonyl chloride, to yield a compound of the type (8), which is compound of formula (I).

Step H:

Reaction of a compound of the type (8), where $—OR^4$ is equal to a leaving group, such as a tosyl group, with an amide or an amine in a reaction-inert-solvent, where preferred solvent is dimethyl acetamide yields (10), a compound of formula (I).

Step I:

The compound of the type (10) where $R^2$ and/or $R^3$ is H is reacted in the presence of a trialkyl base, such as triethylamine or diisopropylethylamine, sodium hydride, with a carbonyl donor, such as an alkyl chloroformate, an acid chloride, an acid anhydride, a sulfonyl chloride, isocyanate, or an activated carboxylic derivative prepared from a carboxylic acid and an activating reagent such as a polymer-supported coupling agent, or, alternatively, dicylohexylcarbodiimide, 1,1carbonyldiimidazole, tripropylphosphonic anhydride, an alkyl chloroformate, bis-(2-oxo-3-oxazolidinyl)phosphinic chloride, or benzotriazol-1-yloxy-tris(dimethylamino)phosphonium hexafluorophosphate, in a reaction-inert-solvent, such as methylene chloride, ethyl acetate, pyridine, tetrahydrofuran or diethyl ether to give a compound of the formula (I).

Step: J

The compound of the type (5) is reacted with N-fluorobenzenesulfonimide in a reaction-inert-solvent, where preferred solvent is toluene at a reaction temperature from room temperature to the reflux temperature of the solvent employed, where 110° C. is an exemplary reaction temperature, to give (9), a compound of formula (I).

Exemplary compounds of formula (I) according to the invention may also be prepared by Scheme 2:

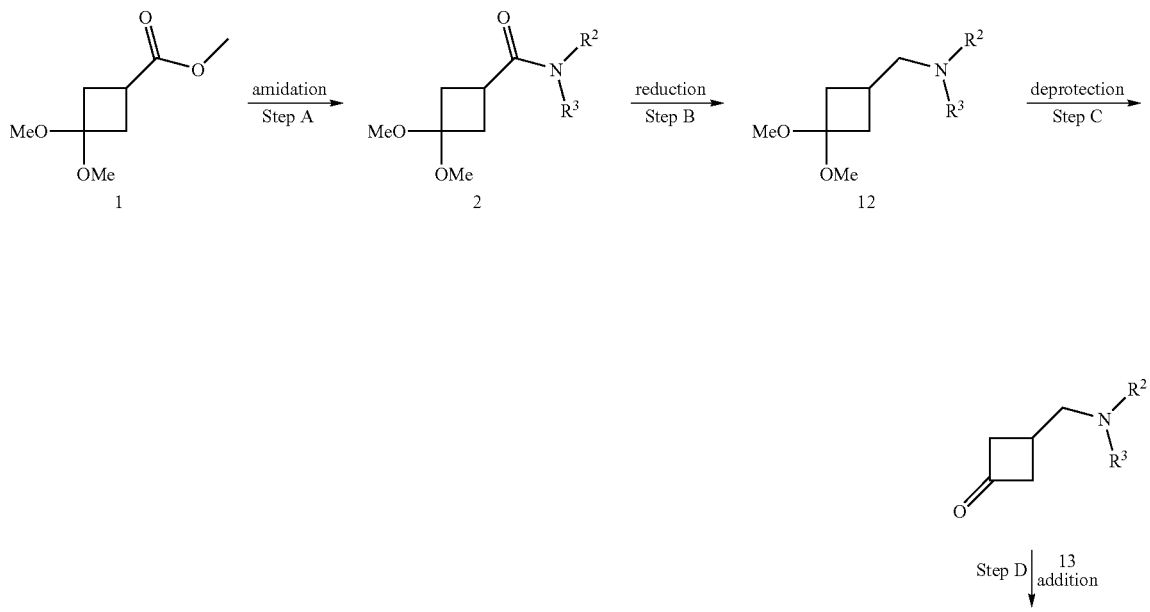

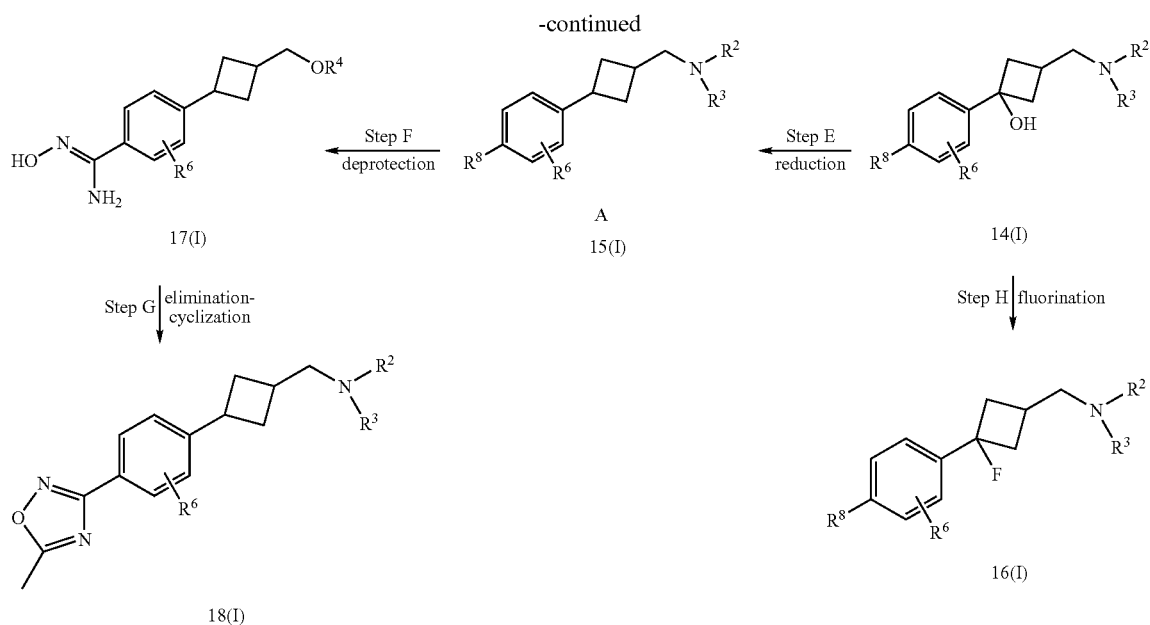

In Scheme 2, compounds of the formula (I) are prepared as follows.

Step A:

The compounds of the general formula (I) are synthesized from 3,3-dimethoxy-cyclobutanecarboxylic acid methyl ester, (1) (J. Org. Chem. 1988, 53, 3841 and J. Org. Chem. 1996, 61, 2174). The ester (1) is reacted with an amine, primary or secondary in the presence of magnesium bromide in a reaction-inert-solvent, where preferred solvent is acetonitrile, at a reaction temperature of about room temperature to the reflux temperature of the solvent employed, where the preferred temperature of the oil bath is 90° C. to yield amide (11).

Step B:

The amide (11) is reduced with an appropriate reduction reagent such as e.g. lithium aluminum hydride, or borane in tetrahydrofuran. The reaction is normally effected in an aprotic solvent, such as tetrahydrofuran, or diethyl ether at a reaction temperature from about 0° C. to the reflux temperature of the solvent employed, yielding the amine (12).

Step C:

The ketal protection group of (12) is removed by methods known in the art (e.g. T. W Greene; P. G. Wuts, Protective Groups in Organic Synthesis, 3$^{rd}$ edition, John Wiley&Sons Inc. New York, 1999). The preferred method of ketal removal is by reaction of (12) in acetone, with an acid, such as hydrogen chloride, p-toluenesulfonic acid monohydrate, or pyridinium p-toluenesulfonate, at a temperature between about room temperature and about the relux temperature of the solvent employed to give ketone (13).

Step D:

The ketone (13) is reacted with an aryl bromide in the presence of an organometallic reagent, such as an organo-lithium, organomagnesium halide, organocerium, organotitanium, organozinc, organocopper, or organolaluminum reagent to form alcohol (14). An organomagnesium halide (Grignard reagent) or organolithium reagent is preferred. The reaction is typically effected in a reaction-inert-solvent, such as tetrahydrofuran, at a temperature between about −78° C. and about room temperature to yield (14), a compound of fomula (I).

Step E:

Reduction of the benzyl alcohol (14) is accomplished by reaction of (14) with an acid, preferably with trifluoroacetic acid, either neat or in a reaction-inert-solvent, such as methylene chloride or 1,2-dichloroethane and in the the presence of a reducing reagent such as a silane, preferable triethylsilane, triisopropylsilane, or triphenylsilane at a reaction temperature from about room temperature to the reflux temperature of the solvent employed, where about 65° C. is the preferred reaction temperature, yields (15) a compound of formula (I). Alternatively, removal of the hydroxyl group of (14) is accomplished in a two step procedure: First, alcohol (14) is treated with an acid, where methane sulfonic acid is preferred in a reaction inert solvent, where 1,2-dichloroethane is preferred at a reaction temperature about 65° C. The resulting crude material is reduced using well-established conditions. Reaction of the crude olefin in 1,2-dichloroethane in the presence of palladium on carbon and in the presence of hydrogen, 45 psi, yields (15), a compound of the formula (I).

Step F:

Reaction of a compound of the type (15), where $R^8$=CN in a polar protic solvent, where lower alcohol solvents are preferred, i.e. methyl alcohol, in the presence of a base, preferably sodium bicarbonate, with hydroxylamine hydrochloride salt at a reaction temperature of about 70° C. gives (17), a compound of the formula (I).

Step G:

Reaction of (17) with acetic anyhydride in a reaction inert solvent, such as 1,2-dichlorethane at the reflux temperature of the solvent employed, yields (18), a compound of formula (I).

Step H:

The compound of the type (14) is reacted with N-fluorobenzenesulfonimide in a reaction-inert-solvent, where preferred solvent is toluene at a reaction temperature from room temperaturer to the reflux temperature of the solvent emploed, where 110° C. is preferred, gives (16), a compound of formula (I).

Exemplary compounds of formula I in accordance with the present invention are the following:

3-Benzyloxymethyl-1-(4-pyrrolidin-1-ylmethyl-phenyl)-cyclobutanol,
1-[4-(3-Benzyloxymethyl-cyclobutyl)-benzyl]-pyrrolidine,
1-[4-(3-Benzyloxymethyl-cyclobutyl)-benzyl]-pyrrolidine,
[3-(4-Pyrrolidin-1-ylmethyl-phenyl)-cyclobutyl]-methanol,
Toluene-4-sulfonic acid 3-(4-pyrrolidin-1-ylmethyl-phenyl)-cyclobutylmethyl ester,
3-[3-(4-Pyrrolidin-1-ylmethyl-phenyl)-cyclobutylmethoxymethyl]-benzonitrile,
2-[3-(4-Pyrrolidin-1-ylmethyl-phenyl)-cyclobutylmethoxymethyl]-benzonitrile,
4-[3-(4-Pyrrolidin-1-ylmethyl-phenyl)-cyclobutylmethoxymethyl]-benzonitrile,
1-{4-[3-(3-Methoxy-benzyloxymethyl)-cyclobutyl]-benzyl}-pyrrolidine,
1-{4-[3-(3-Fluoro-benzyloxymethyl)-cyclobutyl]-benzyl}-pyrrolidine,
1-{4-[3-(4-Trifluoromethoxy-benzyloxymethyl)-cyclobutyl]-benzyl}-pyrrolidine,
1-(4-{3-[(3-Chloro-2-fluoro-phenyl)methoxymethyl]-cyclobutyl-benzyl}-pyrrolidine,
1-{4-[3-(3-Methoxy-benzyloxymethyl)-cyclobutyl]-benzyl}-pyrrolidine,
1-(4-{3-[(3,4-Dichloro-phenyl)methoxymethyl]-cyclobutyl}-benzyl)-pyrrolidine,
1-(4-{3-[(3,5-Difluoro-phenyl)methoxymethyl]-cyclobutyl}-benzyl)-pyrrolidine,
1-{4-[3-(3-Methyl-benzyloxymethyl)-cyclobutyl]-benzyl}-pyrrolidine,
1-{4-[3-(3-Fluoro-benzyloxymethyl)-cyclobutyl]-benzyl}-pyrrolidine,
1-{4-[3-(4-Fluoro-benzyloxymethyl)-cyclobutyl]-benzyl}-pyrrolidine,
1-{4-[3-(4-Trifluoromethyl-benzyloxymethyl)-cyclobutyl]-benzyl}-pyrrolidine,
1-(4-{3-[(2,4-Difluoro-phenyl)methoxymethyl]-cyclobutyl}-benzyl)-pyrrolidine,
1-(4-{3-[(3,4-Difluoro-phenyl)methoxymethyl]-cyclobutyl}-benzyl)-pyrrolidine,
1-{4-[3-(3-Trifluoromethyl-benzyloxymethyl)-cyclobutyl]-benzyl}-pyrrolidine,
1-{4-[3-(4-tert-Butyl-benzyloxymethyl)-cyclobutyl]-benzyl}-pyrrolidine,
1-{4-[3-(2-Fluoro-benzyloxymethyl)-cyclobutyl]-benzyl}-pyrrolidine,
1-{4-[3-(3-Difluoromethoxy-benzyloxymethyl)-cyclobutyl]-benzyl}-pyrrolidine,
1-{4-[3-(2-Benzenesulfonylmethyl-benzyloxymethyl)-cyclobutyl]-benzyl}-pyrrolidine,
1-{4-[3-(1-Phenyl-ethoxymethyl)-cyclobutyl]-benzyl}-pyrrolidine,
1-{4-[3-(4-Methyl-benzyloxymethyl)-cyclobutyl]-benzyl}-pyrrolidine,
1-{4-[3-(3-Nitro-benzyloxymethyl)-cyclobutyl]-benzyl}-pyrrolidine,
1-(4-{3-[(2-Methoxy-5-nitro-phenyl)methoxymethyl]-cyclobutyl}-benzyl)-pyrrolidine,
1-{4-[3-(3-Trifluoromethoxy-benzyloxymethyl)-cyclobutyl]-benzyl}-pyrrolidine,
1-(4-{-3-[(3,5-Dimethoxy-phenyl)methoxymethyl]-cyclobutyl}-benzyl)-pyrrolidine,
2-[3-(4-Pyrrolidin-1-ylmethyl-phenyl)-cyclobutylmethoxymethyl]-pyridine,
1-(4-{-3-[(2,3,4-Trifluoro-phenyl)methoxymethyl]-cyclobutyl}-benzyl)-pyrrolidine,
1{-4-[3-(4-Pyrrolidin-1-ylmethyl-phenyl)-cyclobutylmethoxymethyl]-phenyl}-1H-pyrazole,
1-(4-{3-[(3,5-Dimethyl-phenyl)methoxymethyl]-cyclobutyl}-benzyl)-pyrrolidine,
2-[3-(4-Pyrrolidin-1-ylmethyl-phenyl)-cyclobutylmethoxy]-pyrimidine,
8-Methoxy-2-[3-(4-pyrrolidin-1-ylmethyl-phenyl)-cyclobutylmethoxy]-quinoline,
7-Fluoro-4-methyl-2-[3-(4-pyrrolidin-1-ylmethyl-phenyl)-cyclobutylmethoxy]-quinoline,
4,6-Dimethyl-2-[3-(4-pyrrolidin-1-ylmethyl-phenyl)-cyclobutylmethoxy]-pyrimidine,
2-[3-(4-Pyrrolidin-1-ylmethyl-phenyl)-cyclobutylmethoxy]-pyrazine,
2,5-Dimethyl-3-[3-(4-pyrrolidin-1-ylmethyl-phenyl)-cyclobutylmethoxy]-pyrazine,
2-[3-(4-Pyrrolidin-1-ylmethyl-phenyl)-cyclobutylmethoxy]-pyridine,
2-Methyl-6-[3-(4-pyrrolidin-1-ylmethyl-phenyl)-cyclobutylmethoxy]-pyridine,
3-Methoxy-6-[3-(4-pyrrolidin-1-ylmethyl-phenyl)-cyclobutylmethoxy]-pyridazine,
1-{4-[3-(2-Bromo-benzyloxymethyl)-cyclobutyl]-benzyl}-pyrrolidine,
2,4-Dimethoxy-6-[3-(4-pyrrolidin-1-ylmethyl-phenyl)-cyclobutylmethoxy]-pyrimidine,
cis-Toluene-4-sulfonic acid 3-(4-pyrrolidin-1-ylmethyl-phenyl)-cyclobutylmethyl ester,
trans-Toluene-4-sulfonic acid 3-(4-pyrrolidin-1-ylmethyl-phenyl)-cyclobutylmethyl ester,
trans-[3-(4-Pyrrolidin-1-ylmethyl-phenyl)-cyclobutyl]-methanol,
cis-[3-(4-Pyrrolidin-1-ylmethyl-phenyl)-cyclobutyl]-methanol,
cis4,6-Dimethyl-2-[3-(4-pyrrolidin-1-ylmethyl-phenyl)-cyclobutylmethoxy]-pyrimidine,
cis-2-[3-(4-Pyrrolidin-1-ylmethyl-phenyl)-cyclobutylmethoxy]-pyrimidine,
cis-5-Ethyl-2-[3-(4-pyrrolidin-1-ylmethyl-phenyl)-cyclobutylmethoxy]-pyrimidine,
cis-3-Methyl-6-[3-(4-pyrrolidin-1-ylmethyl-phenyl)-cyclobutylmethoxy]-pyridazine,
trans-4,6-Dimethyl-2-[3-(4-pyrrolidin-1-ylmethyl-phenyl)-cyclobutylmethoxy]-pyrimidine,
trans-2-[3-(4-Pyrrolidin-1-ylmethyl-phenyl)-cyclobutylmethoxy]-pyrimidine,
trans-5-Ethyl-2-[3-(4-pyrrolidin-1-ylmethyl-phenyl)-cyclobutylmethoxy]-pyrimidine,
trans-3-Methyl-6-[3-(4-pyrrolidin-1-ylmethyl-phenyl)-cyclobutylmethoxy]-pyridazine,
cis-5-Methyl-4-piperidin-3-yl-2-[3-(4-pyrrolidin-1-ylmethyl-phenyl)-cyclobutylmethoxy]-pyrimidine,
cis-Pyridin-4-yl-{6-[3-(4-pyrrolidin-1-ylmethyl-phenyl)-cyclobutylmethoxy]-pyridazin-3-yl}-amine,
cis-2-{[3-(4-Pyrrolidin-1-ylmethyl-phenyl)-cyclobutylmethyl]oxy}-4-trifluoromethyl-pyrimidine,
cis-5-Phenyl-2-[3-(4-pyrrolidin-1-ylmethyl-phenyl)-cyclobutylmethoxy]-pyrimidine,
cis-(4-Chloro-phenyl)-{6-[3-(4-pyrrolidin-1-ylmethyl-phenyl)-cyclobutylmethoxy]-pyridazin-3-yl}-methanone,
cis-1,3-Dimethyl-1-{6-[3-(4-pyrrolidin-1-ylmethyl-phenyl)-cyclobutylmethoxy]-pyridazin-3-yl}-urea, cis-4-Pyrrolidin-3-yl-2-[3-(4-pyrrolidin-1-ylmethyl-phenyl)-cyclobutylmethoxy]-pyrimidine,
cis-4-Methyl-6-pyrrolidin-3-yl-2-[3-(4-pyrrolidin-1-ylmethyl-phenyl)-cyclobutylmethoxy]-pyrimidine,
cis-4-(3-Chloro-phenyl)-2-[3-(4-pyrrolidin-1-ylmethyl-phenyl)-cyclobutylmethoxy]-quinazoline,
cis-3-(3-Chloro-phenyl)-1-methyl-1-{6-[3-(4-pyrrolidin-1-ylmethyl-phenyl)-cyclobutylmethoxy]-pyridazin-3-yl}-urea,
cis-5-(4-Methoxy-phenoxy)-2-[3-(4-pyrrolidin-1-ylmethyl-phenyl)-cyclobutylmethoxy]-pyrimidine,
cis-4-Pyridin-2-yl-2-[3-(4-pyrrolidin-1-ylmethyl-phenyl)-cyclobutylmethoxy]-quinazoline,
cis-5-(3-Chloro-phenoxy)-2-[3-(4-pyrrolidin-1-ylmethyl-phenyl)-cyclobutylmethoxy]-pyrimidine,
cis-4-Phenyl-6-piperidin-4-yl-2-[3-(4-pyrrolidin-1-ylmethyl-phenyl)-cyclobutylmethoxy]-pyrimidine,
cis-3-(3-Methyl-5-phenyl-pyrazol-1-yl)-6-{[3-(4-pyrrolidin-1-ylmethyl-phenyl)-cyclobutylmethyl]oxy}-pyridazine,
5-Fluoro-4-piperidin-4-yl-2-[3-(4-pyrrolidin-1-ylmethyl-phenyl)-cyclobutylmethoxy]-pyrimidine,
cis-3-piperazin-1-yl-6-[3-(4-pyrrolidin-1-ylmethyl-phenyl)-cyclobutylmethoxy]-pyridazine,
cis-4-Phenyl-2-{[3-(4-pyrrolidin-1-ylmethyl-phenyl)-cyclobutylmethyl]oxy}-6-trifluoromethyl-pyrimidine,
cis-4-Methyl-6-piperidin-4-yl-2-[3-(4-pyrrolidin-1-ylmethyl-phenyl)-cyclobutylmethoxy]-pyrimidine,
cis-1-Methyl-4-[3-(4-pyrrolidin-1-ylmethyl-phenyl)-cyclobutylmethoxy]-phthalazine,
cis-2-[3-(4-Pyrrolidin-1-ylmethyl-phenyl)-cyclobutylmethoxy]-4-o-tolyl-pyrimidine,
cis-5-(5-Iodo-2-methoxy-benzyl)-3-{[3-(4-pyrrolidin-1-ylmethyl-phenyl)-cyclobutyl]methoxy}-pyridazine,
cis-5-Methyl-4-piperidin-4-yl-2-[3-(4-pyrrolidin-1-ylmethyl-phenyl)-cyclobutylmethoxy]-pyrimidine,
cis-4-(2-Methyl-2H-pyrazol-3-yl)-2-[3-(4-pyrrolidin-1-ylmethyl-phenyl)-cyclobutylmethoxy]-quinazoline,
cis-6-Methyl-2-[3-(4-pyrrolidin-1-ylmethyl-phenyl)-cyclobutylmethoxy]-pyrimidine-4-carboxylic acid phenylamide,
cis-4-Phenyl-2-[3-(4-pyrrolidin-1-ylmethyl-phenyl)-cyclobutylmethoxy]-pyrimidine,
cis-3-(2-Methoxy-benzyl)-6-[3-(4-pyrrolidin-1-ylmethyl-phenyl)-cyclobutylmethoxy]-pyridazine,
cis-Dimethyl-{6-[3-(4-pyrrolidin-1-ylmethyl-phenyl)-cyclobutylmethoxy]-pyridazin-3-yl}-amine,
cis-4-Methyl-6-phenyl-2-[3-(4-pyrrolidin-1-ylmethyl-phenyl)-cyclobutylmethoxy]-pyrimidine,
cis-5-Methyl-4-pyrrolidin-3-yl-2-[3-(4-pyrrolidin-1-ylmethyl-phenyl)-cyclobutylmethoxy]-pyrimidine,
cis-3-(3,5-Dimethyl-pyrazol-1-yl)-6-{[3-(4-pyrrolidin-1-ylmethyl-phenyl)-cyclobutylmethyl]oxy}-pyridazine,
cis-3-(2,5-Dimethyl-pyrrol-1-yl)-6-{[3-(4-pyrrolidin-1-ylmethyl-phenyl)-cyclobutylmethyl]oxy}-pyridazine,
cis-5-(3-Chloro-phenyl)-2-[3-(4-pyrrolidin-1-ylmethyl-phenyl)-cyclobutylmethoxy]-pyrimidine,
cis-5-(4-Methoxy-phenyl)-2-[3-(4-pyrrolidin-1-ylmethyl-phenyl)-cyclobutylmethoxy]-pyrimidine,
cis-4-Phenyl-6-pyridin-2-yl-2-[3-(4-pyrrolidin-1-ylmethyl-phenyl)-cyclobutylmethoxy]-pyrimidine,
cis-4-Phenyl-6-piperidin-3-yl-2-[3-(4-pyrrolidin-1-ylmethyl-phenyl)-cyclobutylmethoxy]-pyrimidine,
2-{4-[3-(4-Pyrrolidin-1-ylmethyl-phenyl)-cyclobutylmethyl]-piperazin-1-yl}-pyrimidine,
Dimethyl-[3-(4-pyrrolidin-1-ylmethyl-phenyl)-cyclobutylmethyl]-amine,
1-{4-[3-(4-Pyrrolidin-1-ylmethyl-phenyl)-cyclobutylmethyl]-piperazin-1-yl}-ethanone,
4-[3-(4-Pyrrolidin-1-ylmethyl-phenyl)-cyclobutylmethyl]-morpholine,
5-Fluoro-2-{4-[3-(4-pyrrolidin-1-ylmethyl-phenyl)-cyclobutylmethyl]-piperazin-1-yl}-pyrimidine,
cis-4-[3-(4-Pyrrolidin-1-ylmethyl-phenyl)-cyclobutylmethyl]-morpholine,
cis-1-[3-(4-Pyrrolidin-1-ylmethyl-phenyl)-cyclobutylmethyl]-piperazine,
cis-5-Fluoro-2-{4-[3-(4-pyrrolidin-1-ylmethyl-phenyl)-cyclobutylmethyl]-piperazin-1-yl}-pyrimidine,
cis-1-[3-(4-Pyrrolidin-1-ylmethyl-phenyl)-cyclobutylmethyl]-pyrrolidine,
cis-1-[3-(4-Pyrrolidin-1-ylmethyl-phenyl)-cyclobutylmethyl]-piperidine,
cis-2-{1-[3-(4-Pyrrolidin-1-ylmethyl-phenyl)-cyclobutylmethyl]-pyrrolidin-2-yl}-pyridine,
cis-(2R,6S)-2,6-Dimethyl-4-[3-(4-pyrrolidin-1-ylmethyl-phenyl)-cyclobutylmethyl]-morpholine,
trans-1-[3-(4-Pyrrolidin-1-ylmethyl-phenyl)-cyclobutylmethyl]-pyrrolidine,
trans-1-[3-(4-Pyrrolidin-1-ylmethyl-phenyl)-cyclobutylmethyl]-piperidine,
trans-2-{1-[3-(4-Pyrrolidin-1-ylmethyl-phenyl)-cyclobutylmethyl]-pyrrolidin-2-yl}-pyridine,
trans-4-[3-(4-Pyrrolidin-1-ylmethyl-phenyl)-cyclobutylmethyl]-morpholine,
trans-1-[3-(4-Pyrrolidin-1-ylmethyl-phenyl)-cyclobutylmethyl]-piperazinyl para-toluenesulfonate,
trans-5-Fluoro-2-{4-[3-(4-pyrrolidin-1-ylmethyl-phenyl)-cyclobutylmethyl]-piperazin-1-yl}-pyrimidine,
trans-2-{Ethyl-[3-(4-pyrrolidin-1-ylmethyl-phenyl)-cyclobutylmethyl]-amino}-ethanol,
trans-3,5-Dimethyl-1-[3-(4-pyrrolidin-1-ylmethyl-phenyl)-cyclobutylmethyl]-piperidine,
trans-Cyclohexyl-methyl-[3-(4-pyrrolidin-1-ylmethyl-phenyl)-cyclobutylmethyl]-amine,
trans-Benzyl-methyl-[3-(4-pyrrolidin-1-ylmethyl-phenyl)-cyclobutylmethyl]-amine,
trans-2-Methyl-1-[3-(4-pyrrolidin-1-ylmethyl-phenyl)-cyclobutylmethyl]-piperidine,
trans-3-Methyl-1-[3-(4-pyrrolidin-1-ylmethyl-phenyl)-cyclobutylmethyl]-piperidine,
trans-4-Methyl-1-[3-(4-pyrrolidin-1-ylmethyl-phenyl)-cyclobutylmethyl]-piperidine,
trans-2-Methyl-1-[3-(4-pyrrolidin-1-ylmethyl-phenyl)-cyclobutylmethyl]-pyrrolidine,
trans-2,6-Dimethyl-1-[3-(4-pyrrolidin-1-ylmethyl-phenyl)-cyclobutylmethyl]-piperidine,
trans-Methyl-pyridin-3-ylmethyl-[3-(4-pyrrolidin-1-ylmethyl-phenyl)-cyclobutylmethyl]-amine,
trans-(2R,5R)-2,5-Dimethyl-1-[3-(4-pyrrolidin-1-ylmethyl-phenyl)-cyclobutylmethyl]-pyrrolidine,
trans-Cyclopropylmethyl-propyl-[3-(4-pyrrolidin-1-ylmethyl-phenyl)-cyclobutylmethyl]-amine,
trans-2-[3-(4-Pyrrolidin-1-ylmethyl-phenyl)-cyclobutylmethyl]-2,3-dihydro-1H-isoindole,
trans-(2R,6S)-2,6-Dimethyl-4-[3-(4-pyrrolidin-1-ylmethyl-phenyl)-cyclobutylmethyl]-morpholine,
trans-4-[3-(4-Pyrrolidin-1-ylmethyl-phenyl)-cyclobutylmethyl]-piperazin-2-one,
trans-(S)-2-Methoxymethyl-1-[3-(4-pyrrolidin-1-ylmethyl-phenyl)-cyclobutylmethyl]-pyrrolidine,
trans-(3,5-Bis-trifluoromethyl-benzyl)-{[3-(4-pyrrolidin-1-ylmethyl-phenyl)-cyclobutyl]methyl}-amine, trans-(5-Methyl-pyrazin-2-ylmethyl)-[3-(4-pyrrolidin-1-yl-methyl-phenyl)-cyclobutylmethyl]-amine,
trans-(2-Methyl-pyridin-3-ylmethyl)-[3-(4-pyrrolidin-1-yl-methyl-phenyl)-cyclobutylmethyl]-amine,
trans-Pyridin-2-ylmethyl-[3-(4-pyrrolidin-1-ylmethyl-phenyl)-cyclobutylmethyl]-amine,
trans-trans-2-{4-[3-(4-Pyrrolidin -1-ylmethyl-phenyl)-cyclobutylmethyl]-piperazin-1-yl}-isonicotinonitrile,
trans-Methyl-pyridin-2-ylmethyl-[3-(4-pyrrolidin-1-ylmethyl-phenyl)-cyclobutylmethyl]-amine,
trans-(3-Chloro-5-trifluoromethyl-pyridin-2-ylmethyl)-{[3-(4-pyrrolidin-1-ylmethyl-phenyl)-cyclobutyl]methyl}-amine,
trans-3-Ethyl-5-{(R)-1-[3-(4-pyrrolidin-1-ylmethyl-phenyl)-cyclobutylmethyl]-pyrrolidin-2-yl}-[1,2,4]oxadiazole,
trans-(6-Methyl-pyridin-2-ylmethyl)-[3-(4-pyrrolidin-1-ylmethyl-phenyl)-cyclobutylmethyl]-amine,
trans-(2-Chloro-6-fluoro-benzyl)-propyl-[3-(4-pyrrolidin-1-ylmethyl-phenyl)-cyclobutylmethyl]-amine,
trans-[3-(3,5-Dimethyl-pyrazol-1-yl)-benzyl]-methyl-[3-(4-pyrrolidin-1-ylmethyl-phenyl)-cyclobutylmethyl]-amine,
trans-1-(5-Chloro-2-methoxy-benzyl)-4-[3-(4-pyrrolidin-1-ylmethyl-phenyl)-cyclobutylmethyl]-piperazine,
trans-(3S,4aS,8aS)-2-[3-(4-Pyrrolidin-1-ylmethyl-phenyl)-cyclobutylmethyl]-decahydro-isoquinoline-3-carboxylic acid tert-butylamide,
trans-(1-Benzyl-piperidin-4-ylmethyl)-methyl-[3-(4-pyrrolidin-1-ylmethyl-phenyl)-cyclobutylmethyl]-amine,
trans-(S)-1-[3-(4-Pyrrolidin-1-ylmethyl-phenyl)-cyclobutylmethyl]-pyrrolidine-2-carboxylic acid amide,
trans-(8-Methoxy-quinolin-5-ylmethyl)-methyl-[3-(4-pyrrolidin-1-ylmethyl-phenyl)-cyclobutylmethyl]-amine,
trans-4-(4-Chloro-phenoxy)-1-[3-(4-pyrrolidin-1-ylmethyl-phenyl)-cyclobutylmethyl]-piperidine,
trans-4-(2-Methoxy-phenoxy)-1-[3-(4-pyrrolidin-1-ylmethyl-phenyl)-cyclobutylmethyl]-piperidine,
trans-4-(3-Chloro-phenoxy)-1-[3-(4-pyrrolidin-1-ylmethyl-phenyl)-cyclobutylmethyl]-piperidine,
trans-Methyl-(4-phenoxy-benzyl)-[3-(4-pyrrolidin-1-ylmethyl-phenyl)-cyclobutylmethyl]-amine,
trans-[1-(2-Methoxy-ethyl)-piperidin-4-ylmethyl]-methyl-[3-(4-pyrrolidin-1-ylmethyl-phenyl)-cyclobutylmethyl]-amine,
trans-1-[3-(4-Pyrrolidin-1-ylmethyl-phenyl)-cyclobutylmethyl]4-p-tolyloxy-piperidine,
trans-2-{Benzyl-[3-(4-pyrrolidin-1-ylmethyl-phenyl)-cyclobutylmethyl]-amino}-ethanol,
trans-[2-(3,4-Dimethoxy-phenyl)-ethyl]-methyl-[3-(4-pyrrolidin-1-ylmethyl-phenyl)-cyclobutylmethyl]-amine,
trans-Methyl-prop-2-ynyl-[3-(4-pyrrolidin-1-ylmethyl-phenyl)-cyclobutylmethyl]-amine,
trans-4-Pyrrolidin-1-yl-1-[3-(4-pyrrolidin-1-ylmethyl-phenyl)-cyclobutylmethyl]-piperidine,
trans-Isopropyl-(2-methoxy-ethyl)-[3-(4-pyrrolidin-1-ylmethyl-phenyl)-cyclobutylmethyl]-amine,
trans-1-Benzyl-4-[3-(4-pyrrolidin-1-ylmethyl-phenyl)-cyclobutylmethyl]-piperazine,
trans-1-Ethyl-4-[3-(4-pyrrolidin-1-ylmethyl-phenyl)-cyclobutylmethyl]-piperazine,
trans-2-{Isopropyl-[3-(4-pyrrolidin-1-ylmethyl-phenyl)-cyclobutylmethyl]-amino}-ethanol,
trans-(2-Methoxy-ethyl)-propyl-[3-(4-pyrrolidin-1-ylmethyl-phenyl)-cyclobutylmethyl]-amine,
trans-Methyl-((R)-1-phenyl-ethyl)-[3-(4-pyrrolidin-1-ylmethyl-phenyl)-cyclobutylmethyl]-amine,
trans-(4S,4aS)-4-Phenyl-1-[3-(4-pyrrolidin-1-ylmethyl-phenyl)-cyclobutylmethyl]-decahydro-quinolin-4-ol,
trans-1-{4-[3-(4-Pyrrolidin-1-ylmethyl-phenyl)-cyclobutylmethyl]-piperazin-1-yl}-ethanone,
trans-1-Methyl-4-[3-(4-pyrrolidin-1-ylmethyl-phenyl)-cyclobutylmethyl]-[1,4]diazepane,
trans-2-{4-[3-(4-Pyrrolidin-1-ylmethyl-phenyl)-cyclobutylmethyl]-piperazin-1-yl}-nicotinonitrile,
trans-Ethyl-(2-methoxy-ethyl)-[3-(4-pyrrolidin-1-ylmethyl-phenyl)-cyclobutylmethyl]-amine,
trans-Methyl-(3-methyl-pyridin-2-ylmethyl)-[3-(4-pyrrolidin-1-ylmethyl-phenyl)-cyclobutylmethyl]-amine,
trans-Diethyl-[3-(4-pyrrolidin-1-ylmethyl-phenyl)-cyclobutylmethyl]-amine,
trans-Benzyl-isopropyl-[3-(4-pyrrolidin-1-ylmethyl-phenyl)-cyclobutylmethyl]-amine,
trans-(S)-2-Pyrrolidin-1-ylmethyl-1-[3-(4-pyrrolidin-1-ylmethyl-phenyl)-cyclobutylmethyl]-pyrrolidine,
trans-((S)-1-Benzyl-pyrrolidin-3-yl)-ethyl-[3-(4-pyrrolidin-1-ylmethyl-phenyl)-cyclobutylmethyl]-amine,
trans-tert-Butyl-(2-methoxy-ethyl)-[3-(4-pyrrolidin-1-ylmethyl-phenyl)-cyclobutylmethyl]-amine,
trans-4-(2-Chloro-phenoxy)-1-[3-(4-pyrrolidin-1-ylmethyl-phenyl)-cyclobutylmethyl]-piperidine,
trans-N-Ethyl-N',N'-dimethyl-N-[3-(4-pyrrolidin-1-ylmethyl-phenyl)-cyclobutylmethyl]-ethane-1,2-diamine,
trans-Dicyclopropylmethyl-methyl-[3-(4-pyrrolidin-1-ylmethyl-phenyl)-cyclobutylmethyl]-amine,
trans-Butyl-methyl-[3-(4-pyrrolidin-1-ylmethyl-phenyl)-cyclobutylmethyl]-amine,
trans-N,N,N'-Trimethyl-N'-[3-(4-pyrrolidin-1-ylmethyl-phenyl)-cyclobutylmethyl]-ethane-1,2-diamine,
trans-1-(1-Methyl-1H-imidazol-2-ylmethyl)-4-[3-(4-pyrrolidin-1-ylmethyl-phenyl)-cyclobutylmethyl]-piperazine,
trans-2,5-Dimethyl-1-[3-(4-pyrrolidin-1-ylmethyl-phenyl)-cyclobutylmethyl]-2,5-dihydro-1H-pyrrole,
trans-((S)-1-Benzyl-pyrrolidin-3-yl)-methyl-[3-(4-pyrrolidin-1-ylmethyl-phenyl)-cyclobutylmethyl]-amine,
trans-(4-Fluoro-benzyl)-methyl-[3-(4-pyrrolidin-1-ylmethyl-phenyl)-cyclobutylmethyl]-amine,
trans-1-Phenyl-8-[3-(4-pyrrolidin-1-ylmethyl-phenyl)-cyclobutylmethyl]-1,3,8-triaza-spiro[4.5]decan-4-one,
trans-2-{-Methyl-[3-(4-pyrrolidin-1-ylmethyl-phenyl)-cyclobutylmethyl]-amino}-ethanol,
trans-3-Benzyl-7-[3-(4-pyrrolidin-1-ylmethyl-phenyl)-cyclobutylmethyl]-5,6,7,8-tetrahydro-[1,2,4]triazolo[4,3-a]pyrazine,
trans-3-{Benzyl-[3-(4-pyrrolidin-1-ylmethyl-phenyl)-cyclobutylmethyl]-amino}-propan-1-ol,
trans-Isobutyl-methyl-[3-(4-pyrrolidin-1-ylmethyl-phenyl)-cyclobutylmethyl]-amine,
trans-Ethyl-isopropyl-[3-(4-pyrrolidin-1-ylmethyl-phenyl)-cyclobutylmethyl]-amine,
trans-Dimethyl-{(R)-1-[3-(4-pyrrolidin-1-ylmethyl-phenyl)-cyclobutylmethyl]-pyrrolidin-3-yl}-amine,
trans-Isopropyl-methyl-[3-(4-pyrrolidin-1-ylmethyl-phenyl)-cyclobutylmethyl]-amine,
trans-Methyl-(5-propyl-1H-pyrazol-3-ylmethyl)-[3-(4-pyrrolidin-1-ylmethyl-phenyl)-cyclobutylmethyl]-amine,
trans-(1R,2S)-2-{Methyl-[3-(4-pyrrolidin-1-ylmethyl-phenyl)-cyclobutylmethyl]-amino}-1-phenyl-propan-1-ol,
trans-2-{1-[3-(4-Pyrrolidin-1-ylmethyl-phenyl)-cyclobutylmethyl]-piperidin-4-yl}-benzooxazole,
trans-3-Propyl-7-[3-(4-pyrrolidin-1-ylmethyl-phenyl)-cyclobutylmethyl]-5,6,7,8-tetrahydro-[1,2,4]triazolo[4,3-a]pyrazine, trans-Benzyl-((R)-1-phenyl-ethyl)-[3-(4-pyrrolidin-1-ylmethyl-phenyl)-cyclobutylmethyl]-amine,
trans-tert-Butyl-ethyl-[3-(4-pyrrolidin-1-ylmethyl-phenyl)-cyclobutylmethyl]-amine,
trans-1-Methyl-4-[3-(4-pyrrolidin-1-ylmethyl-phenyl)-cyclobutylmethyl]-piperazine,
trans-Isopropyl-[3-(4-pyrrolidin-1-ylmethyl-phenyl)-cyclobutylmethyl]-(1,3,5-trimethyl-1H-pyrazol-4-ylmethyl)-amine,
trans-4-{Benzyl-[3-(4-pyrrolidin-1-ylmethyl-phenyl)-cyclobutylmethyl]-amino}-butan-1-ol,
trans-(1R,2R)-2-{Methyl-[3-(4-pyrrolidin-1-ylmethyl-phenyl)-cyclobutylmethyl]-amino}-1-phenyl-propan-1-ol,
trans-Benzyl-ethyl-[3-(4-pyrrolidin-1-ylmethyl-phenyl)-cyclobutylmethyl]-amine,
trans-6-{4-[3-(4-Pyrrolidin-1-ylmethyl-phenyl)-cyclobutylmethyl]-piperazin-1-yl}-nicotinonitrile,
trans-Methyl-[3-(4-pyrrolidin-1-ylmethyl-phenyl)-cyclobutylmethyl]-(2-trifluoromethyl-benzyl)-amine,
trans-3-(3-Methoxy-phenyl)-6-[3-(4-pyrrolidin-1-ylmethyl-phenyl)-cyclobutylmethyl]-5,6,7,8-tetrahydro-4H-1,2,3a,6-tetraaza-azulene,
trans-Methyl-phenethyl-[3-(4-pyrrolidin-1-ylmethyl-phenyl)-cyclobutylmethyl]-amine,
trans-3-{Pyridin-2-ylmethyl-[3-(4-pyrrolidin-1-ylmethyl-phenyl)-cyclobutylmethyl]-amino}-propan-1-ol,
trans-Bis-pyridin-2-ylmethyl-[3-(4-pyrrolidin-1-ylmethyl-phenyl)-cyclobutylmethyl]-amine,
trans-Bis-(3-chloro-benzyl)-[3-(4-pyrrolidin-1-ylmethyl-phenyl)-cyclobutylmethyl]-amine,
trans-Cyclopropyl-[3-(4-pyrrolidin-1-ylmethyl-phenyl)-cyclobutylmethyl]-(1,3,5-trimethyl-1H-pyrazol-4-ylmethyl)-amine,
trans-Methyl-pyridin-4-ylmethyl-[3-(4-pyrrolidin-1-ylmethyl-phenyl)-cyclobutylmethyl]-amine,
trans-3-(3,4-Difluoro-phenyl)-6-[3-(4-pyrrolidin-1-ylmethyl-phenyl)-cyclobutylmethyl]-5,6,7,8-tetrahydro-4H-1,2,3a,6-tetraaza-azulene,
3-Pyrrolidin-1-ylmethyl-1-(4-pyrrolidin-1-ylmethyl-phenyl)-cyclobutanol,
1-(4-Piperidin-1-ylmethyl-phenyl)-3-pyrrolidin-1-ylmethyl-cyclobutanol,
1-(4-Benzyloxymethyl-phenyl)-3-pyrrolidin-1-ylmethyl-cyclobutanol,
4-(1-Hydroxy-3-pyrrolidin-1-ylmethyl-cyclobutyl)-benzonitrile,
1-(4-Morpholin-4-ylmethyl-phenyl)-3-piperidin-1-ylmethyl-cyclobutanol,
3-Morpholin-4-ylmethyl-1-(4-morpholin-4-ylmethyl-phenyl)-cyclobutanol,
1-(4-Dimethylaminomethyl-phenyl)-3-pyrrolidin-1-ylmethyl-cyclobutanol,
3-(4-Pyrimidin-2-yl-piperazin-1-ylmethyl)-1-(4-pyrrolidin-1-ylmethyl-phenyl)-cyclobutanol,
1-[4-(3-Pyrrolidin-1-ylmethyl-cyclobutyl)-benzyl]-pyrroline,
4-[4-(3-Piperidin-1-ylmethyl-cyclobutyl)-benzyl]-morpholine,
1-[4-(3-Pyrrolidin-1-ylmethyl-cyclobutyl)-benzyl]-piperidine,
Dimethyl-[4-(3-pyrrolidin-1-ylmethyl-cyclobutyl)-benzyl]-amine,
4-(3-Pyrrolidin-1-ylmethyl-cyclobutyl)-benzonitrile,
4-(3-Pyrrolidin-1-ylmethyl-cyclobutyl)-N-hydroxy-benzamidine,
5-Methyl-3-[4-(3-pyrrolidin-1-ylmethyl-cyclobutyl)-phenyl]-[1,2,4]oxadiazole,
4-(3-Pyrrolidin-1-ylmethyl-cyclobutyl)-benzylamine,
1-(3-p-Tolyl-cyclobutylmethyl)-pyrrolidine,
trans-1-[4-(3-Benzyloxymethyl-cyclobutyl)-benzyl]-pyrrolidine, and
trans-1-[4-(3-Azidomethyl-cyclobutyl)-benzyl]-pyrrolidine.

Preferred examples of compounds according to the present invention include:
trans-2-[3-(4-Pyrrolidin-1-ylmethyl-phenyl)-cyclobutylmethoxy]-pyrimidine;
trans-5-Ethyl-2-[3-(4-pyrrolidin-1-ylmethyl-phenyl)-cyclobutylmethoxy]-pyrimidine;
trans-3-Methyl-6-[3-(4-pyrrolidin-1-ylmethyl-phenyl)-cyclobutylmethoxy]-pyridazine;
cis-5-Methyl-4-piperidin-3-yl-2-[3-(4-pyrrolidin-1-ylmethyl-phenyl)-cyclobutylmethoxy]-pyrimidine;
cis-Pyridin-4-yl-{6-[3-(4-pyrrolidin-1-ylmethyl-phenyl)-cyclobutylmethoxy]-pyridazin-3-yl}-amine;
cis-2-{[3-(4-Pyrrolidin-1-ylmethyl-phenyl)-cyclobutylmethyl]oxy}-4-trifluoromethyl-pyrimidine;
cis-5-Phenyl-2-[3-(4-pyrrolidin-1-ylmethyl-phenyl)-cyclobutylmethoxy]-pyrimidine;
cis-(4-Chloro-phenyl)-{6-[3-(4-pyrrolidin-1-ylmethyl-phenyl)-cyclobutylmethoxy]-pyridazin-3-yl}-methanone;
cis-1,3-Dimethyl-1-{6-[3-(4-pyrrolidin-1-ylmethyl-phenyl)-cyclobutylmethoxy]-pyridazin-3-yl}-urea;
cis-4-Pyrrolidin-3-yl-2-[3-(4-pyrrolidin-1-ylmethyl-phenyl)-cyclobutylmethoxy]-pyrimidine;
cis-4-Methyl-6-pyrrolidin-3-yl-2-[3-(4-pyrrolidin-1-ylmethyl-phenyl)-cyclobutylmethoxy]-pyrimidine;
cis-4-(3-Chloro-phenyl)-2-[3-(4-pyrrolidin-1-ylmethyl-phenyl)-cyclobutylmethoxy]-quinazoline;
cis-3-(3-Chloro-phenyl)-1-methyl-1-{6-[3-(4-pyrrolidin-1-ylmethyl-phenyl)-cyclobutylmethoxy]-pyridazin-3-yl}-urea;
cis-5-(4-Methoxy-phenoxy)-2-[3-(4-pyrrolidin-1-ylmethyl-phenyl)-cyclobutylmethoxy]-pyrimidine;
cis-4-Pyridin-2-yl-2-[3-(4-pyrrolidin-1-ylmethyl-phenyl)-cyclobutylmethoxy]-quinazoline;
cis-5-(3-Chloro-phenoxy)-2-[3-(4-pyrrolidin-1-ylmethyl-phenyl)-cyclobutylmethoxy]-pyrimidine;
cis-4-Phenyl-6-piperidin-4-yl-2-[3-(4-pyrrolidin-1-ylmethyl-phenyl)-cyclobutylmethoxy]-pyrimidine;
cis-3-(3-Methyl-5-phenyl-pyrazol-1-yl)-6-{[3-(4-pyrrolidin-1-ylmethyl-phenyl)-cyclobutylmethyl]oxy}-pyridazine;
5-Fluoro-4-piperidin-4-yl-2-[3-(4-pyrrolidin-1-ylmethyl-phenyl)-cyclobutylmethoxy]-pyrimidine;
cis-3-piperazin-1-yl-6-[3-(4-pyrrolidin-1-ylmethyl-phenyl)-cyclobutylmethoxy]-pyridazine;
cis-4-Phenyl-2-{[3-(4-pyrrolidin-1-ylmethyl-phenyl)-cyclobutylmethyl]oxy}-6-trifluoromethyl-pyrimidine;
cis-4-Methyl-6-piperidin-4-yl-2-[3-(4-pyrrolidin-1-ylmethyl-phenyl)-cyclobutylmethoxy]-pyrimidine;
cis-1-Methyl-4-[3-(4-pyrrolidin-1-ylmethyl-phenyl)-cyclobutylmethoxy]-phthalazine;
cis-2-[3-(4-Pyrrolidin-1-ylmethyl-phenyl)-cyclobutylmethoxy]-4-o-tolyl-pyrimidine;
cis-5-(5-Iodo-2-methoxy-benzyl)-3-{[3-(4-pyrrolidin-1-ylmethyl-phenyl)-cyclobutyl]methoxy}-pyridazine;
cis-5-Methyl-4-piperidin-4-yl-2-[3-(4-pyrrolidin-1-ylmethyl-phenyl)-cyclobutylmethoxy]-pyrimidine;
cis-4-(2-Methyl-2H-pyrazol-3-yl)-2-[3-(4-pyrrolidin-1-ylmethyl-phenyl)-cyclobutylmethoxy]-quinazoline;
cis-6-Methyl-2[3-(4-pyrrolidin-1-ylmethyl-phenyl)-cyclobutylmethoxy]-pyrimidine-4-carboxylic acid phenylamide;

cis-4-Phenyl-2-[3-(4-pyrrolidin-1-ylmethyl-phenyl)-cyclobutylmethoxy]-pyrimidine;
cis-3-(2-Methoxy-benzyl)-6-[3-(4-pyrrolidin-1-ylmethyl-phenyl)-cyclobutylmethoxy]-pyridazine;
cis-Dimethyl-{6-[3-(4-pyrrolidin-1-ylmethyl-phenyl)-cyclobutylmethoxy]-pyridazin-3-yl}-amine;
cis-4-Methyl-6-phenyl-2-[3-(4-pyrrolidin-1-ylmethyl-phenyl)-cyclobutylmethoxy]-pyrimidine;
cis-5-Methyl-4-pyrrolidin-3-yl-2-[3-(4-pyrrolidin-1-ylmethyl-phenyl)-cyclobutylmethoxy]-pyrimidine;
cis-3-(3,5-Dimethyl-pyrazol-1-yl)-6-{[3-(4-pyrrolidin-1-ylmethyl-phenyl)-cyclobutylmethyl]oxy}-pyridazine;
cis-3-(2,5-Dimethyl-pyrrol-1-yl)-6-{[3-(4-pyrrolidin-1-ylmethyl-phenyl)-cyclobutylmethyl]oxy}-pyridazine;
cis-5-(3-Chloro-phenyl)-2-[3-(4-pyrrolidin-1-ylmethyl-phenyl)-cyclobutylmethoxy]-pyrimidine;
cis-5-(4-Methoxy-phenyl)-2-[3-(4-pyrrolidin-1-ylmethyl-phenyl)-cyclobutylmethoxy]-pyrimidine;
cis-4-Phenyl-6-pyridin-2-yl-2-[3-(4-pyrrolidin-1-ylmethyl-phenyl)-cyclobutylmethoxy]-pyrimidine;
cis-4-Phenyl-6-piperidin-3-yl-2-[3-(4-pyrrolidin-1-ylmethyl-phenyl)-cyclobutylmethoxy]-pyrimidine;
2-{4-[3-(4-Pyrrolidin-1-ylmethyl-phenyl)-cyclobutylmethyl]-piperazin-1-yl}-pyrimidine;
Dimethyl-[3-(4-pyrrolidin-1-ylmethyl-phenyl)-cyclobutylmethyl]-amine;
1-{4-[3-(4-Pyrrolidin-1-ylmethyl-phenyl)-cyclobutylmethyl]-piperazin-1-yl}-ethanone;
4-[3-(4-Pyrrolidin-1-ylmethyl-phenyl)-cyclobutylmethyl]-morpholine;
5-Fluoro-2-{4-[3-(4-pyrrolidin-1-ylmethyl-phenyl)-cyclobutylmethyl]-piperazin-1-yl}-pyrimidine;
cis-4-[3-(4-Pyrrolidin-1-ylmethyl-phenyl)-cyclobutylmethyl]-morpholine;
trans-4-[3-(4-Pyrrolidin-1-ylmethyl-phenyl)-cyclobutylmethyl]-thiomorpholine;
trans-6-{4-[3-(4-Pyrrolidin-1-ylmethyl-phenyl)-cyclobutylmethyl]-piperazin-1-yl}-nicotinonitrile;
trans-1-Methanesulfonyl-4-[3-(4-pyrrolidin-1-ylmethyl-phenyl)-cyclobutylmethyl]-piperazine;
trans-1-Ethanesulfonyl-4-[3-(4-pyrrolidin-1-ylmethyl-phenyl)-cyclobutylmethyl]-piperazine;
trans-1-(Propane-2-sulfonyl)-4-[3-(4-pyrrolidin-1-ylmethyl-phenyl)-cyclobutylmethyl]-piperazine;
trans-2-Methyl-1-{-4-[3-(4-pyrrolidin-1-ylmethyl-phenyl)-cyclobutylmethyl]-piperazin-1-yl}-propan-1-one;
trans-(1S,4S)-2-Methanesulfonyl-5-[3-(4-pyrrolidin-1-ylmethyl-phenyl)-cyclobutylmethyl]-2,5-diaza-bicyclo[2.2.1]heptane;
cis-1-{4-[3-(4-Pyrrolidin-1-ylmethyl-phenyl)-cyclobutylmethyl]-piperazin-1-yl}-ethanone; and
cis-4-[3-(4-Pyrrolidin-1-ylmethyl-phenyl)-cyclobutylmethyl]-thiomorpholine.

In the examples below the following terms are intended to have the following, general meaning:
DIPEA: diisopropylethylamine
DMF: dimethylformamide
$MgSO_4$: magnesium sulfate
DMA: dimethyl acetamide
LRMS: low resolution mass spectrometry
°C: degrees Celsius
calcd; calculated
d; day(s); doublet (spectral)
DCE: 1,2-dichloroethane
EtOAc: ethyl acetate
g: grams
hr; hours
Hz: hertz
J: coupling constant (in NMR)
L: liter(s)
LAH: lithium aluminum hydride
MHz: megahertz
Min: minute(s)
m/z mass to charge ratio (in mass spectrometry)
obsd: observed
PPTs: pyridinium p-toluenesulfonate:
TsO: p-toluenesulfonate
Rf: retention factor (in chromatography)
Rt: retention time (in chromatography)
rt: room temperature
s: singlet (NMR), second(s)
t: triplet
TFA: trifluoroacetic acid
TFAA: trifluoroacetic anhydride
THF: tetrahydrofuran
TLC: thin layer chromatography
Ts: tosyl, p-toluenesulfonyl
TsOH: p-toluenesulfonic acid Solvents were purchased and used without purification. Yields were calculated for material judged homogenous by thin layer chromatography and NMR. Thin layer chromatography was performed on Merck Kieselgel 60 F 254 plates eluting with the solvents indicated, visualized by a 254 nm UV lamp, and stained with either an aqueous $KMnO_4$ solution or an ethanolic solution of 12-molybdophosphoric acid. Flash column chromatography was performed with using either pre-packed Biotage® or ISCO® columns using the size indicated. Nuclear magnetic resonance (NMR) spectra were acquired on a Unity 400 or 500 at 400 MHz or 500 MHz for $^1H$, respectively, and 100 MHz or 125 MHz for $^{13}C$ NMR, respectively. Chemical shifts for proton $^1H$ NMR spectra are reported in parts per million relative to the singlet of $CDCl_3$ at 7.24 ppm. Chemical shifts for $^{13}C$ NMR spectra are reported in parts per million downfield relative to the center line of the triplet of CDCl at 77.0 ppm. Mass spectra analyses were performed on a APCI Gilson 215, micromass ZMD (50% Acetonitrile/50% water) spectrometer.

HPLC was performed according to the following methods:

Method A: Preparative conditions (Waters 600 & Waters 2767 Sample Manager); Column: Waters Symmetry $C_{18}$, 5 μm, 30×150 mm steel column, part # WAT248000, serial # M12921A01; solvent A—0.1% Triflouroacetic acid/water; solvent B—Acetonitrile; volume of injection: 850 μL; time 0.0, 100% solvent A, 0% solvent B, flow 20; time 2.0, 100% solvent A, 0% solvent B, flow 20; time 12.0, 0% solvent A, 100% solvent B, flow 20; time 15.0, 0% solvent A, 100% solvent B, flow 20; time 15.1, 100% solvent A, 0% solvent B, flow 20; time 20.0, 100% solvent A, 0% solvent B, flow 20.

Mass spectral (micromassZO) conditions; Capillary(kV): 3.0; Cone (V): 20; Extractor (V): 3.0; RF Lens (V): 0.5; Source temp. (° C.): 120; Desolvation temp. (° C.): 360; Desolvation gas flow (L/hr): 450; Cone gas flow (L/hr): 150; LM Resolution: 15; HM Resolution: 15; Ion Energy: 0.2; Multiplier: 550.

Splitter; Acurate by LC Packings, 1/10,000; Upchurch needle valve setting: 14; Make up pump (Waters 515) Flow (ml/min.): 1.

PDA (Waters 996) Settings; Start/End wavelength (nm): 200/600; Resolution: 1.2; Sample Rate: 1; Channels: TIC, 254 nm and 220 nm.

Method B: Preparative conditions (Waters 600 & Waters 2767 Sample Manager); Column: Waters Xterra PrepMS $C_{18}$ column, 5 µm, 30×150 mm steel column, part # 186001120, serial # T22881T 09; solvent A—0.1% Triflouroacetic acid/water; solvent B—Acetonitrile; volume of injection: 1050 µL; time 0.0, 100% solvent A, 0% solvent B, flow 20; time 2.0, 100% solvent A, 0% solvent B, flow 20; time 12.0, 0% solvent A, 100% solvent B, flow 20; time 14.0, 0% solvent A, 100% solvent B, flow 20; time 14.1, 100% solvent A, 0% solvent B, flow 20; time 19.1, 100% solvent A, 0% solvent B, flow 20.

Mass spectral (micromassZO) conditions; Capillary(kV): 3.0; Cone (V): 20; Extractor (V): 3.0; RF Lens (V): 0.5; Source temp. (° C.): 120; Desolvation temp. (° C.): 360; Desolvation gas flow (L/hr): 450; Cone gas flow (L/hr): 150; LM Resolution: 15; HM Resolution: 15; Ion Energy. 0.2; Multiplier: 550.

Splitter; Acurate by LC Packings, 1/10,000; Upchurch needle valve setting: 14; Make up pump (Waters 515) Flow (ml/min.): 1.

PDA (Waters 996) Settings; Start/End wavelength (nm): 200/600; Resolution: 1.2; Sample Rate: 1; Channels: TIC, 254 nm and 220 nm.

Method C: Preparative conditions (Waters 600 & Waters 2767 Sample Manager); Column: Waters Symmetry $C_{18}$, 5 µm, 30×150 mm steel column, part # WAT248000, serial # M12921A01; solvent A—0.1% Triflouroacetic acid/water; solvent B—Acetonitrile; volume of injection: 850 µL; time 0.0, 90% solvent A, 10% solvent B, flow 20; time 10.0, 0% solvent A, 100% solvent B, flow 20; time 12.0, 0% solvent A, 100% solvent B, flow 20.

Mass spectral (micromassZO) conditions; Capillary(kV): 3.0; Cone (V): 20; Extractor (V): 3.0; RF Lens (V): 0.5; Source temp. (° C.): 120; Desolvation temp. (° C.): 360; Desolvation gas flow (L/hr): 450; Cone gas flow (L/hr): 150; LM Resolution: 15; HM Resolution: 15; Ion Energy: 0.2; Multiplier: 550.

Splitter; Acurate by LC Packings, 1/10,000; Upchurch needle valve setting: 14; Make up pump (Waters 515) Flow (ml/min.): 1.

PDA (Waters 996) Settings; Start/End wavelength (nm): 200/600; Resolution: 1.2; Sample Rate: 1; Channels: TIC, 254 nm and 220 nm.

The following intermediates may be prepared by the procedures shown:

Intermediate 1—General Procedure A:—

Step A:

(3,3-Dimethoxy-cyclobutyl)-methanol. To a stirring solution of 3,3-dimethoxy-cyclobutanecarboxylic acid methyl ester, (J. Org. Chem. 1988, 53, 3841 and J. Org. Chem. 1996, 61, 2174) (15.0 g, 86.1 mmol) in 40 mL of tetrahydrofuran at 0° C. (ice/water bath) was added dropwise a solution of lithium aluminum hydride (103.3 mL, 1M tetrahydrofuran). After the addition was complete the reaction was warmed to room temperature and stirred 12 hours. The reaction was worked-up using the method of Feiser and Feiser, and then filtered through a plug of Celite and concentrated under reduced pressure to yield (3,3-dimethoxy-cyclobutyl)-methanol (12.4 g, 99% crude yield) as a colorless oil. This material was used without further purification.

500 MHz 1H NMR (CDCl3) δ 3.64 (d, J=5.7 Hz, 2H), 3.15 (s, 3H), 3.13 (s, 3H), 2.32–2.23 (m, 3H), 1.94 (bs, 1H), 1.92–1.84 (m, 2H); 125 MHz 13C NMR (CDCl3) δ 101.0, 66.9, 48.7, 48.4, 34.3, 27.0; C7H14O3, 146.185, MS Low res (M-OCH3)=115.1;

Intermediate 2—General Procedure A:

Step B:

[(3,3-Dimethoxy-cyclobutyl)methoxymethyl]-benzene. To a stirring solution of crude (3,3-dimethoxy-cyclobutyl)-methanol (11.9 g, 81.5 mmol) in 100 mL of tetrahydrofuran at room temperature was added a solution of potassium t-butoxide (163 mL, 1M tetrahydrofuran). The reaction was allowed to stir for 30 minutes and then benzyl bromide (10.2 mL, 85.6 mmol) was added. After 30 minutes TLC analysis indicated complete consumption of starting material. The reaction was quenched with water and diluted with methylene chloride. The organic layer was separated, dried over magnesium sulfate, filtered, and concentrated under reduced pressure. Purification of this material was accomplished by flash column chromatography using a Biotage Column 75 medium, eluting with a gradient of hexanes through 5% EtOAc/hexanes. The product containing fractions were collected and concentrated under reduced pressure to give the title compound (13.2 g, 69% yield), as a colorless oil.

Rf=0.75 (40% EtOAc/Hexanes); 500 MHz 1H NMR (CDCl3) δ 7.36–7.25 (m, 5H), 4.52 (s, 2H), 3.48 (d, J=7.0 Hz, 2H), 3.16 (s, 3H), 3.12 (s, 3H), 2.44–2.26 (m, 3H), 1.90–1.84 (m, 2H); 100 MHz 13C NMR (CDCl3) δ 138.8, 128.6, 127.9, 127.8, 101.1, 74.7, 73.2, 48.6, 48.4, 34.9, 24.9; C14H20O3, 236.309, MS Low res (M-OCH3)=205.3.

Intermediate 3—General Procedure A:

Step C

3-Benzyloxymethyl-cyclobutanone. To a stirring solution of [(3,3-dimethoxy-cyclobutyl)methoxymethyl]-benzene (13.0 g, 55.1 mmol) in 200 mL of a mixture of acetone:water (3:1) was added p-toluenesulfonic acid mono hydrate (2.1 g, 11.0 mmol). The reaction mixture was heated to 65 C for 45 minutes. Both TLC and GS/MS analysis indicated complete consumption of starting material. The reaction was cooled to room temperature and then the acetone was removed under reduced pressure. The resulting mixture was diluted with ethyl acetate and washed with an aqueous solution 5% NaOH. The layers were separated and the organic layer was dried over magnesium sulfate, filtered through a fritted funnel and then concentrated under reduced pressure. Purification of this material was accomplished by flash chromatography using a Biotage Column 75 small, eluting with a 10% EtOAc/hexanes. The product containing fractions were collected and concentrated under reduced pressure to yield the title compound (6.0 g, 58% yield) as a colorless oil.

Rf=0.35 (30% EtOAc/Hexanes); 500 MHz 1H NMR (CDCl3) δ 7.39–7.27 (m, 5H), 4.56 (s, 2H), 3.59 (d, J=6.3 Hz, 2H), 3.18–3.08 (m, 2H), 2.92–2.84 (m, 2H), 2.75–2.64 (m, 1H); 100 MHz 13C NMR (CDCl3) δ 207.6, 138.3, 128.7, 127.9, 127.8, 73.4, 73.1, 50.2, 23.9; C12H14O2, 190.241, GC/MS 190, Retention time=2.46 min (Stationary phase: HP-1, fused silica, description: 12 m×0.202 mm×0.33 um. temperature limits: −60 C to 325 C, ramp rate=30 C/min, solvent delay=0.4 min).

The following compounds may be prepared by the procedures below:

EXAMPLE 1

General Procedure A

Step D:

3-Benzyloxymethyl-1-(4-pyrrolidin-1-ylmethyl-phenyl)-cyclobutanol

To a stirring solution of 1-(4-bromo-benzyl)-pyrrolidine (1.9 g, 7.9 mmol) in 13 mL of tetrahydrofuran at −78 C(iPrOH/dry ice) was added slowly down the side of the flask a solution of n-butyl lithium (3.2 mL, 7.9 mmol, 2.5 M in THF). After 30 minutes a precooled −78 C (iPrOH/CO$_2$ ice) solution of 3-benzyloxymethyl-cyclobutanone (1.0 g, 5.3 mmol, in 1 mL of THF) was added via cannula down the side of the flask (wash 1 mL). The resulting solution was stirred at −78 C for 30 minutes, then quenched with a saturated solution of aqueous NH$_4$OH and diluted with EtOAc. The layers were separated and the organic layer was dried over magnesium sulfate, filtered through a fritted funnel and then concentrated under reduced pressure. Purification of this material was accomplished by flash column chromatography using a Biotage column, eluting with a gradient of 2% MeOH/CH$_2$Cl$_2$ w/0.1% NH$_4$OH through 30% MeOH/CH$_2$Cl$_2$ w/0.1% NH$_4$OH. The product containing fractions were collected and concentrated under reduced pressure to yield the title compound (1.3 g, 71% yield) as a colorless oil and a 3:1 mixture of cis:trans isomers.

Rf=0.45 (15% MeOH/CH2Cl2 w/0.1% NH4OH); 1H NMR; cis:trans isomers, diagnostic peaks 400 MHz 1H NMR (CDCl3) δ 7.36–7.25 (m), 7.22–7.06 (m), 6.57–6.54 (m), 4.59 (s), 4.50 (s), 3.64–3.58 (m), 3.53 (s), 2.56–2.50 (m), 2.42–2.21 (m), 1.82–1.77 (m); LRMS m/z Calcd for C23H29NO$_2$, 351.487; obsd LRMS (M+1) 352.4;

EXAMPLE 2

General Procedure A

Step E

1-[4-(3-Benzyloxymethyl-cyclobutyl)-benzyl]-pyrrolidine

To a stirring solution of 3-benzyloxymethyl-1-(4-pyrrolidin-1-ylmethyl-phenyl)-cyclobutanol (1.0 g, 2.8 mmol) in 10 mL of 1,2-dichlorethane was added triethyl silane (4.5 mL, 28.5 mmol) followed by the addition of trifluoroacetic acid (4.4 mL, 57.0 mmol). The reaction was then heated to 75 C (oil bath). After 1 hour the reaction was cooled to room temperature and then concentrated under reduced pressure. The crude material was taken up in EtOAc and washed with an aqueous solution of 1M NaOH. The layer were separated and the organic layer was dried over magnesium sulfate, filtered through a fritted funnel and concentrated under reduced pressure. Purification of this material was accomplished by flash column chromatography using a 45 g ISCO column, eluting with a gradient of 2% MeOH/CH$_2$Cl$_2$ w/0.1% NH$_4$OH, through 10% MeOH/CH$_2$Cl$_2$ w/0.1% NH$_4$OH. The product containing fractions were collected and concentrated to give the title compound (yield not determined due to presence of TFA) as a colorless oil and a 1:1 mixture of cis:trans isomers. Further purification of this material is not required.

Scale-up: To a stirring solution of 3-benzyloxymethyl-1-(4-pyrrolidin-1-ylmethyl-phenyl)-cyclobutanol (21.6 g, 61.5 mmol) in neat triethyl silane (49 mL, 307 mmol) was added trifluoroacetic acid (47 mL, 615 mmol). The reaction was then heated to 75 □C (oil bath). After 30 minutes the reaction was cooled to room temperature and then concentrated under reduced pressure and used without further purification.

Rf=0.3 (10% MeOH/CH2Cl2 w/0.1% NH4OH); cis:trans isomers, diagnostic peaks 400 MHz 1H NMR (CDCl3) δ 7.36–7.29 (m), 7.27–7.16 (m), 4.57 (s), 4.48 (s), 4.08 (s), 3.60 (d, J=7.5 Hz), 3.42 (d, J=5.8 Hz), 2.61–2.53 (m), 2.48–2.41 (m), 2.24–2.19 (m); cis:trans isomers, diagnostic peaks 100 MHz 13C NMR (CDCl3) δ 148, 138.8, 130.4, 128.6, 127.4, 74.3, 73.3, 58.2, 52.9, 36.6, 33.1, 31.5, 30.9, 23.1; LRMS m/z Calcd for C23H29N O, 335.488; obsd LRMS (M+1), 336.4.

EXAMPLE 3

General Procedure A

Step F:

[3-(4-Pyrrolidin-1-ylmethyl-phenyl)-cyclobutyl]-methanol

To a stirring solution of crude 1-[4-(3-benzyloxymethyl-cyclobutyl)-benzyl]-pyrrolidine TFA salt prepared above (61.5 mmol) in 250 mL of ethyl alcohol was added palladium black (4.0 g, 20% by wt). The Parr bottle was then pressurized with H$_2$ to 45 psi. After complete consumption of starting material as evident by LRMS the reaction vessel was evacuated (removal of H$_2$ gas), then the reaction was filtered through a plug of Celite, and concentrated under reduced pressure. The residual was diluted with CH$_2$Cl$_2$ and washed with a saturated solution of NaHCO$_3$. The aqueous layer was back extracted with 3:1 CHCl$_3$:iPrOH. The organic layers were dried over magnesium sulfate, filtered through a fritted funnel and concentrated under reduced pressure. Purification of this material was accomplished by flash chromatography, using a Biotage column 75 large, eluting with a gradient of 2% MeOH/CH$_2$Cl$_2$ w/0.2% NH$_4$OH, through 20% MeOH/CH$_2$Cl$_2$ w/0.2% NH$_4$OH. The product containing fractions were collected and concentrated, $^{13}$C NMR revealed the presence of TFA. The product was free based by reaction with aqueous K$_2$CO$_3$, and extracted with 3:1 CHCl$_3$:iPrOH to yield the title compound (11.9 g, 79% yield) as a colorless oil and a mixture of cis:trans isomers.

Rf=0.33 (10% MeOH/CH2Cl2 w/0.1% NH4OH); 1H NMR; cis:trans isomers, diagnostic peaks 400 MHz 1H NMR (CDCl3) δ 7.3 (m), 3.65–3.64 (m), 3.46–3.45 (m), 2.60–2.58 (m), 1.81–1.80 (m); cis:trans isomers, diagnostic peaks 100 MHz 13C NMR (CDCl3) δ 145.7, 145.2, 135.2, 129.5, 126.6, 67.3, 66.7, 60.3, 54.1, 36.6, 35.9, 33.5, 33.1, 31.2, 23.4; LRMS m/z Calcd for C16H23NO 245.364; obsd LRMS (M+1) 246.3.

EXAMPLE 4

General Procedure A

Step G:

Toluene-4-sulfonic acid 3-(4-pyrrolidin-1-ylmethyl-phenyl)-cyclobutylmethyl ester To a stirring solution of [3-(4-pyrrolidin-1-ylmethyl-phenyl)-cyclobutyl]-methanol (0.56 g, 2.3 mmol) prepared above in 5 mL of dichlormethane was added triethyl amine (1.6 mL, 2.7 mmol) followed by 4-(dimethyl amino)pyridine (2.8 mg, 0.23 mmol) and p-toluene sulfonyl chloride (0.52 g, 2.7 mmol). After 1 hr the reaction was quenched with a saturated aqueous solution of $NaHCO_3$. The reaction was diluted and extracted with dichloromethane. The organic layers were dried over magnesium sulfate, filtered through a fritted funnel, and concentrated under reduced pressure. Purification of this material was accomplished by flash column chromatography, using a 40 g ISCO column, eluting with a gradient of 4%, 6%, and 10% $MeOH/CH_2Cl_2$. The product containing fractions were collected and concentrate under reduced pressure to give the title compound (0.82 g, 93% yield) as a colorless oil and a mixture of cis:trans isomers.

Rf=0.29 (10% $MeOH/CH2Cl2$ w/0.1% $NH4OH$); $^1H$ NMR; cis:trans isomers, diagnostic peaks 400 MHz 1H NMR (CDCl3) δ 7.83–7.77 (m), 7.37–7.32 (m), 7.27–7.23 (m), 7.13–7.06 (m), 4.18 (s), 3.99 (s), 3.59 (bs), 3.53–3.49 (m), 2.64–2.55 (m), 2.52 (bs), 2.45 (d, J=3.7 Hz), 2.29–2.12 (m), 1.86–1.72 (m); cis:trans isomers, diagnostic peaks 100 MHz 13C NMR (CDCl3) δ 144.9, 133.4, 130.1, 129.2, 129.1, 128.1, 74.2, 73.8, 60.5, 54.4, 36.1, 35.9, 32.4, 30.9, 23.6, 21.9; LRMS m/z Calcd for C23H29NO3S 399.56; obsd LRMS (M+1) 400.3.

EXAMPLE 5

General Procedure A

Step G:

3-[3-(4-Pyrrolidin-1-ylmethyl-phenyl)-cyclobutyl-methoxymethyl]-benzonitrile

To a stirring solution of [3-(4-pyrrolidin-1-ylmethyl-phenyl)-cyclobutyl]-methanol (50.0 mg, 0.20 mmol) prepared above (Step F) in 3 mL of tetrahydrofuran was added a solution of KotBu (0.42 mL, 0.41 mmol, 1M THF). After 30 minutes 3-(bromomethyl)-benzonitrile (42.0 mg, 0.21 mmol), in 1 mL of THF was added and then the reaction was heated to 40° C. (oil bath). After 3 hours the reaction was quenched with water and diluted with EtOAc. The layers were separated and the organic layer was dried over $MgSO_4$, filtered through a fitted funnel and concentrated under reduced pressure. This material was purified by flash chromatography using a 4 g ISCO column, eluting with a gradient of 2%, 4%, 8% $MeOH/CH_2Cl_2$ w/0.1% $NH_4OH$. The product containing fractions were collected and concentrated to give the title compound (29.0 mg, 39% yield) as a colorless oil and a mixture of cis:trans isomers.

Rf=0.63 (10% MeOH/CH2Cl2 w/0.1% NH4OH); 1H NMR; cis:trans isomers, diagnostic peaks 400 MHz 1H NMR (CDCl3) δ 7.66–7.55 (m), 7.48–7.42 (m), 7.29–7.25 (m), 7.20–7.14 (m), 4.58 (s), 4.53 (s), 3.66 (d J=7.0 Hz), 3.62 (s), 2.62–2.47 (m), 2.32–2.20 (m), 1.94–1.86 (m), 1.81–1.78 (m); cis:trans isomers, diagnostic peaks 100 MHz 13C NMR (CDCl3) δ 140.5, 131.9, 131.8, 131.4, 131.3, 131.1, 129.4, 126.5, 119.1, 112.7, 75.6, 74.9, 72.1, 71.9, 60.5, 54.3, 36.7, 36.2, 33.2, 31.6, 23.6; LRMS m/z Calcd for C24H28N2O 360.498 obsd LRMS (M+1) 361.4.

EXAMPLE 6

2-[3-(4-Pyrrolidin-1-ylmethyl-phenyl)-cyclobutyl-methoxymethyl]-benzonitrile

Preparation as described for Example 5, General Procedure A, Step G.

Rf=0.54 (10% MeOH/CH2Cl2 w/0.1% NH4OH); cis:trans isomers, diagnostic peaks 400 MHz 1H NMR (CDCl3) δ 7.67–7.58 (m), 7.41–7.36 (m), 7.28–7.14 (m), 4.75 (s), 4.70 (s), 3.74 (d, J=7.0 Hz), 3.60 (s), 2.66–2.61 (m), 2.52–2.45 (m), 2.32–2.25 (m), 1.97–1.89 (m), 1.80–1.77 (m); cis:trans isomers, diagnostic peaks 100 MHz 13C NMR (CDCl3) δ 142.6, 133.1, 132.9, 129.2, 128.2, 126.5, 126.4, 111.7, 75.8, 75.3, 70.9, 70.7 60.6, 54.3, 36.7, 36.3, 31.6, 30.8, 23.6; LRMS m/z Calcd for C24H28N2O 360.498: obsd LRMS (M+1) 361.4.

EXAMPLE 7

4-[3-(4-Pyrrolidin-1-ylmethyl-phenyl)-cyclobutyl-methoxymethyl]-benzonitrile

Preparation as described for Example 5, General Procedure A, Step G.

Rf=0.29 (10% MeOH/CH2Cl2 w/0.1% NH4OH); cis:trans isomers, diagnostic peaks 400 MHz 1H NMR (CDCl3) δ 7.66–7.62 (m), 7.48–7.42 (m), 7.28–7.24 (m), 7.19–7.13 (m), 4.61 (s), 4.56 (s), 3.47 (d, J=6.2 Hz), 3.66 (d, J=7.5 Hz), 3.61 (s, 2H), 2.64–2.44 (m), 2.33–2.17 (m), 1.95–1.87 (m), 1.81–1.78 (m); cis:trans isomers, diagnostic peaks 100 MHz 13C NMR (CDCl3) δ 144.5, 132.4, 129.2, 127.9, 127.8, 126.5, 75.6, 75.0, 72.2, 60.5, 54.3, 36.7, 33.2, 30.9, 23.6; LRMS m/z Calcd for C24H28N2O 360.498; obsd LRMS (M+1) 361.4.

EXAMPLE 8

1-{4-[3-(3-Methoxy-benzyloxymethyl)-cyclobutyl]-benzyl}-pyrrolidine

Preparation as described for Example 5, General Procedure A, Step G.

Rf=0.40 10% MeOH/CH2Cl2 w/0.1% NH4OH); cis:trans isomers, diagnostic peaks 400 MHz 1H NMR (CDCl3) δ 7.35–7.16 (m), 6.95–6.80 (m), 4.55 (s), 4.49 (s), 3.81 (d, J=5.4 Hz), 3.75 (bs), 2.70–2.55 (m), 2.50–2.44 (m), 2.31–2.19 (m), 1.90–1.84 (m); cis:trans isomers, diagnostic peaks 100 MHz 13C NMR (CDCl3) δ 140.5, 129.6, 126.8, 120.1, LRMS m/z Calcd for C24H31NO2 365.514; obsd LRMS (M+1) 366.4.

EXAMPLE 9

1-{4-[3-(3-Fluoro-benzyloxymethyl)-cyclobutyl]-benzyl}-pyrrolidine

Preparation as described for Example 5, General Procedure A, Step G.

Rf=0.29 (10% MeOH/CH2Cl2 w/0.1% NH4OH); cis:trans isomers, diagnostic peaks 400 MHz 1H NMR (CDCl3)

δ7.32–7.24 (m), 7.19–7.08 (m), 6.97–6.95 (m), 4.55 (s), 4.50 (s), 3.63 (d, J=7.5 Hz), 3.59 (s), 2.60–2.59 (m), 2.51–2.44 (m), 2.31–2.21 (m), 1.91–1.88 (m), 1.79–1.76 (m); cis:trans isomers, diagnostic peaks 100 MHz 13C NMR (CDCl3) δ 130.1, 129.0, 126.5, 123.1, 114.6, 114.4, 75.3, 72.5, 60.6, 54.4, 36.7, 36.2, 33.3, 31.7, 23.6, LRMS m/z Calcd for C23H28FNO 353.478; obsd LRMS (M+1) 354.4.

EXAMPLE 10

General Procedure A

Step G

Alternative High Through-put Procedure:

Benzyl bromides (0.132 mmol, 1.05 equiv) were pre-weighed into 2-dram vials. A stock solution of [3-(4-pyrrolidin-1-ylmethyl-phenyl)-cyclobutyl]-methanol and KOtBu was made. Using the following amounts times the number or reactions run, (30.7 mg, 0.125 mmol, 1 equiv) dissolved in 0.75 ml of dry THF and a solution of KOtBu (1 N in THF, 0.25 ml, 0.25 mmol, 2 equiv) was added. This mixture was shaken at room temperature for ~15 minutes (yellow cloudy solution). After ~15 minutes 1 ml of this stock solution was added to each bromide starting material. The resulting reactions were heated and shaken at 45° C. for 20 hours. After 20 hours the reactions were quenched with 0.5 ml of MeOH and loaded by hand onto Silicycle SCX SPE cartridge and then rinsed with CH2Cl2. The vials were changed and eluted with 5 ml of MeOH then switched to a tared vials and eluted with 7.5 ml of 1 N TEA in MeOH. Stripped off solvent, weighed. Purification was accomplished using the HPLC reported method. The product containing fractions were compressed into tared vials.

1-{4-[3-(4-Trifluoromethoxy-benzyloxymethyl)-cyclobutyl]-benzyl}-pyrrolidine

Rt=4.48 min HPLC method A; LRMS m/z Calcd for C24H28F3NO2 419.491 obsd LRMS (M+1) 420.13.

EXAMPLE 11

1-(4-{-3-[(3-Chloro-2-fluoro-phenyl)methoxymethyl]-cyclobutyl}-benzyl)-pyrrolidine Preparation as described for Example 10, General Procedure A, Step G.
Rt=4.72 min HPLC method A; LRMS m/z Calcd for C23H27ClFNO 387.929; obsd LRMS (M+1) 388.13.

EXAMPLE 12

1-{4-[3-(3-Methoxy-benzyloxymethyl)-cyclobutyl]-benzyl}-pyrrolidine

Preparation as described for Example 10, General Procedure A, Step G.
Rt=4.63 min HPLC method A; LRMS m/z Calcd for C24H31NO2 365.52; obsd LRMS (M+1) 366.16.

EXAMPLE 13

1-(4-{3-[(3,4-Dichloro-phenyl)methoxymethyl]-cyclobutyl}-benzyl)-pyrrolidine

Preparation as described for Example 10, General Procedure A, Step G.
Rt=4.85 min HPLC method A; LRMS m/z Calcd for C23H27Cl2NO 403.00; obsd LRMS (M+1) 404.08.

EXAMPLE 14

1-(4-{-3-[(3,5-Difluoro-phenyl)methoxymethyl]-cyclobutyl}-benzyl)-pyrrolidine

Preparation as described for Example 10, General Procedure A, Step G.
Rt=4.7 min HPLC method A; LRMS m/z Calcd for C23H27F2NO 371.475; obsd LRMS (M+1) 372.15.

EXAMPLE 15

1-{4-[3-(3-Methyl-benzyloxymethyl)-cyclobutyl]-benzyl}-pyrrolidine

Preparation as described for Example 10, General Procedure A, Step G.
Rt=9.19 min HPLC method C; LRMS m/z Calcd for C24H31NO 349.521; obsd LRMS (M+1) 350.4.

EXAMPLE 16

1-{4-[3-(3-Fluoro-benzyloxymethyl)-cyclobutyl]-benzyl}-pyrrolidine

Preparation as described for Example 10, General Procedure A, Step G.
Rt=9.63 min HPLC method C; LRMS m/z Calcd for C23H28FNO 353.484; obsd LRMS (M+1) 354.4.

EXAMPLE 17

1-{4-[3-(4-Fluoro-benzyloxymethyl)-cyclobutyl]-benzyl}-pyrrolidine

Preparation as described for Example 10, General Procedure A, Step G.
Rt=8.91 min HPLC method C; LRMS m/z Calcd for C23H28FNO 353.484; obsd LRMS (M+1) 354.4.

EXAMPLE 18

1-{4-[3-(4-Trifluoromethyl-benzyloxymethyl)-cyclobutyl]-benzyl}-pyrrolidine

Preparation as described for Example 10, General Procedure A, Step G.
Rt=9.50 min HPLC method C; LRMS m/z Calcd for C24H28F3NO 403.492; obsd LRMS (M+1) 404.4.

EXAMPLE 19

1-(4-{3-[(2,4-Difluoro-phenyl)methoxymethyl]-cyclobutyl}-benzyl)-pyrrolidine

Preparation as described for Example 10, General Procedure A, Step G.

Rt=9.03 min HPLC method C; LRMS m/z Calcd for C23H27F2NO 371.475; obsd LRMS (M+1) 372.4.

EXAMPLE 20

1-(4-{3-[(3,4-Difluoro-phenyl)methoxymethyl]-cyclobutyl}-benzyl)-pyrrolidine

Preparation as described for Example 10, General Procedure A, Step G.
Rt=9.06 min HPLC method C; LRMS m/z Calcd for C23H27F2NO 371.475 obsd LRMS (M+1) 372.4.

EXAMPLE 21

1-{4-[3-(3-Trifuoromethyl-benzyloxymethyl)-cyclobutyl]-benzyl}-pyrrolidine

Preparation as described for Example 10, General Procedure A, Step G.
Rt=9.45 min HPLC method C; LRMS m/z Calcd for C24H28F3NO 403.492; obsd LRMS (M+1) 404.4.

EXAMPLE 22

1-{4-[3-(4-tert-Butyl-benzyloxymethyl)-cyclobutyl]-benzyl}-pyrrolidine

Preparation as described for Example 10, General Procedure A, Step G.
Rt=10.15 min HPLC method C; LRMS m/z Calcd for C27H37NO 391.602; obsd LRMS (M+1) 392.5.

EXAMPLE 23

1-{4-[3-(2-Fluoro-benzyloxymethyl)-cyclobutyl]-benzyl}-pyrrolidine

Preparation as described for Example 10, General Procedure A, Step G.
Rt=8.89 min HPLC method C; LRMS m/z Calcd for C23H28FNO 353.484; obsd LRMS (M+1) 354.4.

EXAMPLE 24

1-{4-[3-(3-Difluoromethoxy-benzyloxymethyl)-cyclobutyl]-benzyl}-pyrrolidine

Preparation as described for Example 10, General Procedure A, Step G.
Rt=9.09 min HPLC method C; LRMS m/z Calcd for C24H29F2NO2 401.501; obsd LRMS (M+1) 402.4.

EXAMPLE 25

1-{4-[3-(2-Benzenesulfonylmethyl-benzyloxymethyl)-cyclobutyl]-benzyl}-pyrrolidine Preparation as described for Example 10, General Procedure A, Step G.
Rt=8.95 min HPLC method C; LRMS m/z Calcd for C30H35NO3S 489.682; obsd LRMS (M+1) 490.5.

EXAMPLE 26

1-{4-[3-(1-Phenyl-ethoxymethyl)-cyclobutyl]-benzyl}-pyrrolidine

Preparation as described for Example 10, General Procedure A, Step G.
Rt=9.09 min HPLC method C;

EXAMPLE 27

1-{4-[3-(4-Methyl-benzyloxymethyl)-cyclobutyl]-benzyl}-pyrrolidine

Preparation as described for Example 10, General Procedure A, Step G.
Rt=9.19 min HPLC method C; LRMS m/z Calcd for C24H31NO 349.521; obsd LRMS (M+1) 350.4.

EXAMPLE 28

1-{4-[3-(3-Nitro-benzyloxymethyl)-cyclobutyl]-benzyl}-pyrrolidine

Preparation as described for Example 10, General Procedure A, Step G.
Rt=8.83 min HPLC method C;

EXAMPLE 29

1-(4-{-3-[(2-Methoxy-5-nitro-phenyl)methoxymethyl]-cyclobutyl}-benzyl)-pyrrolidine Preparation as described for Example 10, General Procedure A, Step G.
Rt=8.89 min HPLC method C; LRMS m/z Calcd for C24H30N2O4 410.518; obsd LRMS (M+1) 411.4.

EXAMPLE 30

1-{4-[3-(3-Trifluoromethoxy-benzyloxymethyl)-cyclobutyl]-benzyl}-pyrrolidine

Preparation as described for Example 10, General Procedure A, Step G.
Rt=9.09 min HPLC method C; LRMS m/z Calcd for C24H28F3NO2 419.491; obsd LRMS (M+1) 420.4.

EXAMPLE 31

1-(4-{3-[(3,5-Dimethoxy-phenyl)methoxymethyl]-cyclobutyl}-benzyl)-pyrrolidine

Preparation as described for Example 10, General Procedure A, Step G.
Rt=8.95 min HPLC method C; LRMS m/z Calcd for C25H33NO3 395.547; obsd LRMS (M+1) 396.4.

EXAMPLE 32

2-[3-(4-Pyrrolidin-1-ylmethyl-phenyl)-cyclobutyl-methoxymethyl]-pyridine

Preparation as described for Example 10, General Procedure A, Step G.
Rt=9.09 min HPLC method C; LRMS m/z Calcd for C22H28N2O 336.481; obsd LRMS (M+1) 337.4.

EXAMPLE 33

1-(4-{3-[(2,3,4-Trifluoro-phenyl)methoxymethyl]-cyclobutyl}-benzyl)-pyrrolidine

Preparation as described for Example 10, General Procedure A, Step G.
Rt=9.19 min HPLC method C; LRMS m/z Calcd for C23H26F3NO 389.465; obsd LRMS (M+1) 390.4.

EXAMPLE 34

1-{4-[3-(4-Pyrrolidin-1-ylmethyl-phenyl)-cyclobutylmethoxymethyl]-phenyl}-1-H-pyrazole Preparation as described for Example 10, General Procedure A, Step G.
Rt=8.83 min HPLC method C; LRMS m/z Calcd for C26H31N3O 401.556; obsd LRMS (M+1) 402.4.

EXAMPLE 35

1-(4-{3-[(3,5-Dimethyl-phenyl)methoxymethyl]-cyclobutyl}-benzyl)-pyrrolidine

Preparation as described for Example 10, General Procedure A, Step
Rt=9.56 min HPLC method C; LRMS m/z Calcd for C25H33NO 363.548 obsd LRMS (M+1) 364.4.

EXAMPLE 36

General Procedure A

Step G:

2-[3-(4-Pyrrolidin-1-ylmethyl-phenyl)-cyclobutylmethoxy]-pyrimidine

To a stirring solution of [3-(4-pyrrolidin-1-ylmethyl-phenyl)-cyclobutyl]-methanol (38.0 mg, 0.16 mmol) prepared above (Step F) in 1.5 mL of THF was added 2-chloropyrimidine (21.3 mg, 0.19 mmol) followed by a solution of KotBu (310 uL, 0.31 mmol, 1 M THF). The reaction immediately turned to a dark pink/milky solution. When mass spectral analysis indicated complete consumption of starting alcohol (15 minutes) the reaction was quenched with an aqueous solution of $NH_4Cl$. The reaction was diluted with a 3:1 mixture of chloroform/isopropyl alcohol. The layers were separated and the organic layer was dried over $MgSO_4$, filtered through a fritted glass filter, and concentrated under reduced pressure to yield the title compound as a mixture of cis:trans isomers. Conversion to the HCl salt was accomplished by dissolving the free base in EtOAc, and then adding 1 eq of a solution of HCl (1 M THF). The colorless solid was collected and dried under reduced pressure to yield 45 mg of a colorless solid, and as a mixture of isomers.
Rf=0.25 (25% MeOH/CH2Cl2 w/0.2% NH4OH); cis:trans isomers, diagnostic peaks 400 MHz 1H NMR (CDCl3) δ 8.46 (d, J=5.0 Hz), 8.44 (d, J=5.0 Hz), 7.43–7.39 (m), 7.21–7.14 (m), 6.90–6.86 (m), 4.46 (d, J=7.5 Hz), 4.28 (d, J=6.2 Hz), 3.95 (s), 3.67–3.58 (m), 3.42–3.35 (m), 2.80–2.71 (m), 2.52–2.46 (m), 2.34–2.25 (m), 1.99–1.91 (m); cis:trans isomers, diagnostic peaks 100 MHz 13C NMR (CDCl3) δ 165.6, 159.5, 147.1, 130.3, 127.1, 115.2, 71.5, 70.1, 58.9, 53.3, 36.5, 32.8, 31.3, 30.1, 23.4; LRMS m/z Calcd for C20H25N3O 323.438; obsd LRMS (M+1) 324.4.

EXAMPLE 37

8-Methoxy-2-[3-(4-pyrrolidin-1-ylmethyl-phenyl)-cyclobutylmethoxy]-quinoline

Preparation as described for Example 36, General Procedure A, Step G using the appropriate starting materials.
Rf=0.30 (10% MeOH/CH2Cl2 w/0.2% NH4OH); cis:trans isomers, diagnostic peaks 500 MHz 1H NMR (CDCl3) δ 7.92–7.88 (m), 7.52–7.42 (m), 7.27–7.19 (m), 7.0–6.95 (m), 6.90–6.87 (m), 4.62 (d, J=7.1 Hz, major isomer), 4.44 (d, J=5.8 Hz, minor isomer), 4.03 (s), 3.70–3.62 (m, major isomer), 3.43–3.34 (m, minor isomer), 3.04 (bs), 2.80–2.70 (m, major isomer), 2.52–2.44 (m, minor isomer), 2.37–2.24 (m), 2.02–1.92 (m); cis:trans isomers, diagnostic peaks 125 MHz 13C NMR (CDCl3) δ 162.1, 154.1, 147.7, 139.1, 130.5, 127.4, 124.1, 119.8, 113.7, 109.2, 69.3, 56.5, 53.1, 36.6, 32.9, 31.5, 30.4, 23.3; LRMS m/z Calcd for C26H30N2O2 402.535; obsd LRMS (M+1) 403.4.

EXAMPLE 38

7-Fluoro-4-methyl-2-[3-(4-pyrrolidin-1-ylmethyl-phenyl)-cyclobutylmethoxy]-quinoline Preparation as described for Example 36, General Procedure A, Step G using the appropriate starting materials.
Rf=0.25 (10% MeOH/CH2Cl2 w/0.2% NH4OH); cis:trans isomers, diagnostic peaks 400 MHz 1H NMR (CDCl3) δ 7.79–7.74 (m), 7.50–7.40 (m), 7.30–7.20 (m), 7.10–7.05 (m), 4.54 (d, J=7.4 Hz, major isomer), 4.36 (d, J=5.8 Hz, minor isomer), 4.04 (s), 3.72–3.62 (m, major isomer), 3.45–3.35 (m, minor isomer), 2.80–2.82 (m), 2.70–2.67 (m), 2.51 (s), 2.53–2.45 (m), 2.35–2.26 (m), 2.04–1.95 (m); cis:trans isomers, diagnostic peaks 100 MHz 13C NMR (CDCl3) δ 130.5, 130.4, 127.3, 127.2, 125.8, 125.7, 113.4, 113.2, 112.6, 112.1, 111.9, 69.5, 69.2, 58.6, 53.2, 36.6, 32.9, 31.4, 30.3, 23.3, 19.0; LRMS m/z Calcd for C26H29FN2O 404.526; obsd LRMS (M+1) 405.4.

EXAMPLE 39

4,6-Dimethyl-2-[3-(4-pyrrolidin-1-ylmethyl-phenyl)-cyclobutylmethoxy]-pyrimidine Preparation as described for Example 36, General Procedure A, Step G using the appropriate starting materials.
Rf=0.20 (10% MeOH/CH2Cl2 w/0.2% NH4OH); cis:trans isomers, diagnostic peaks 400 MHz 1H NMR (CDCl3) δ 7.43–7.34 (m), 7.23–7.11 (m), 6.61 (s, major isomer), 6.59 (s, minor isomer), 4.44 (d, J=7.0 Hz, major isomer), 4.25 (d, J=6.6 Hz, minor isomer), 3.90 (s), 3.66–3.57 (m, major isomer), 3.43–3.34 (m, minor isomer), 2.88 (bs), 2.77–2.69 (m), 2.52–2.46 (m), 2.35 (s), 2.33 (s), 1.97–1.88 (m); cis:trans isomers, diagnostic peaks 100 MHz 13C NMR (CDCl3) δ 169.3, 165.4, 130.1, 127.1, 114.1, 71.3, 70.6, 59.1, 53.4, 36.3, 31.4, 30.7, 30.3, 24.1, 23.4; LRMS m/z Calcd for C22H29N3O 351.491; obsd LRMS (M+1) 352.4.

EXAMPLE 40

2-[3-(4-Pyrrolidin-1-ylmethyl-phenyl)-cyclobutylmethoxy]-pyrazine

Preparation as described for Example 36, General Procedure A, Step G using the appropriate starting materials.

Rf=0.25 (10% MeOH/CH2Cl2 w/0.2% NH4OH); cis: trans isomers, diagnostic peaks 500 MHz 1H NMR (CDCl3) δ 8.16 (d, J=1.7 Hz, major isomer), 8.14 (d, J=1.3 Hz, minor isomer), 8.04–7.97 (m), 7.52–7.40 (m), 7.20–7.15 (m), 4.39 (d, J=7.1 Hz, major isomer), 4.21 (d, J=6.2 Hz, minor isomer), 4.04 (s, major isomer), 4.03 (s, minor isomer), 3.64–3.56 (m, major isomer), 3.42–3.32 (m, minor isomer), 3.04 (bs), 2.76–2.64 (m), 2.45 (dddd, J=2.9, 2.9, 2.9, 2.9 Hz), 2.31–2.21 (m), 2.02–1.94 (m), 1.92 (dddd, J=2.5, 2.5, 2.5, 2.5 Hz); cis:trans isomers, diagnostic peaks 100 MHz 13C NMR (CDCl3) δ 160.6, 160.5, 147.3, 146.9, 140.7, 136.6, 136.1, 130.5, 127.2, 70.1, 69.7, 58.5, 53.2, 36.5, 36.1, 32.7, 31.2, 30.1, 23.3; LRMS m/z Calcd for C20H25N3O 323.438; obsd LRMS (M+1) 324.3.

EXAMPLE 41

2,5-Dimethyl-3-[3-(4-pyrrolidin-1-ylmethyl-phenyl)-cyclobutylmethoxy]-pyrazine

Preparation as described for Example 36, General Procedure A, Step G using the appropriate starting materials.
Rf=0.28 (10% MeOH/CH2Cl2 w/0.2% NH4OH); cis:trans isomers, diagnostic peaks 500 MHz 1H NMR (CDCl3) δ 7.78 (s, major isomer), 7.76 (s, minor isomer), 7.44–7.35 (m), 7.22–7.15 (m), 4.40 (d, J=7.1 Hz, major isomer), 4.22 (d, J=5.8 Hz, minor isomer), 3.90 (s, major isomer), 3,88 (s, minor isomer), 3.68–3.59 (m, major isomer), 3.43–3.34 (m, minor isomer), 2.92–2.84 (bm), 2.76–2.65 (m), 2.45 (dddd, J=2.5, 2.5, 2.5, 2.5 Hz), 2.38–2.26 (m), 1.98 (dddd, J=2.5, 2.5, 2.5, 2.5 Hz), 1.95–1.87 (m); cis:trans isomers, diagnostic peaks 100 MHz 13C NMR (CDCl3) δ 158.1, 157.9, 147.7, 146.8, 141.1, 134.4, 130.2, 127.1, 69.3, 59.1, 53.5, 36.6, 36.2, 32.8, 31.4, 30.2, 23.4, 20.9, 19.0; LRMS m/z Calcd for C22H29N3O 351.491; obsd LRMS (M+1) 352.3.

EXAMPLE 42

2-[3-(4-Pyrrolidin-1-ylmethyl-phenyl)-cyclobutylmethoxy]-pyridine

Preparation as described for Example 36, General Procedure A, Step G using the appropriate starting materials.
Rf=0.25 (10% MeOH/CH2Cl2 w/0.2% NH4OH); cis:trans isomers, diagnostic peaks 500 MHz 1H NMR (CDCl3) δ 8.11 (dd, J=1.3, 1.3 Hz), 8.08 (dd, J=1.7, 1.7 Hz), 7.54–7.48 (m), 7.44–7.38 (m), 6.84–6.77 (m), 6.73–6.67 (m), 4.40 (d, J=6.5 Hz, major isomer), 4.21 (d, J=6.2 Hz, minor isomer), 3.91 (s), 3.68–3.58 (m, major isomer), 3.44–3.25 (m, minor isomer), 2.89 (bm), 2.77–2.65 (m), 2.47 (dddd, J=2.5, 2.5, 2.5, 2.5 Hz), 2.32–2.24 (m), 1.96 (dddd, J=2.9, 2.9, 2.9, 2.9 Hz), 1.98–1.87 (m); cis:trans isomers, diagnostic peaks 100 MHz 13C NMR (CDCl3) δ 164.3, 147.0, 138.7, 130.1, 127.1, 116.8, 111.3, 69.4, 59.1, 53.5, 36.6, 32.9, 31.4, 30.7, 23.4; LRMS m/z Calcd for C21H26N2O 322.449; obsd LRMS (M+1) 323.3.

EXAMPLE 43

2-Methyl-6-[3-(4-pyrrolidin-1-ylmethyl-phenyl)-cyclobutylmethoxy]-pyridine

Preparation as described for Example 36, General Procedure A, Step G using the appropriate starting materials.
Rf=0.25 (10% MeOH/CH2Cl2 w/0.2% NH4OH); cis:trans isomers, diagnostic peaks 500 MHz 1H NMR (CDCl3) δ 7.47–7.38 (m), 7.25–7.18 (m), 6.69–6.64 (m), 6.52–6.47 (m), 4.38 (d, J=7.5 Hz, major isomer), 4.20 (d, J=6.2 Hz, minor isomer), 3.98 (s), 3.69–3.59 (m, major isomer), 3.44–3.34 (m, minor isomer), 3.00 (bs), 2.77–2.66 (m), 2.48 (dddd, J=2.5, 2.5, 2.5, 2.5 Hz), 2.41 S, major isomer), 2.39 (s, minor isomer), 2.34–2.26 (m), 2.02–1.92 (m); cis:trans isomers, diagnostic peaks 100 MHz 13C NMR (CDCl3) δ 163.8, 156.5, 147.4, 139.0, 130.4, 127.2, 115.9, 107.3, 69.2, 58.8, 53.3, 36.6, 33.0, 31.4, 30.4, 23.4; LRMS m/z Calcd for C22H28N2O 336.476; obsd LRMS (M+1) 337.4.

EXAMPLE 44

3-Methoxy-6-[3-(4-pyrrolidin-1-ylmethyl-phenyl)-cyclobutylmethoxy]-pyridazine

Preparation as described for Example 36, General Procedure A, Step G using the appropriate starting materials.
Rf=0.25 (10% MeOH/CH2Cl2 w/0.2% NH4OH); cis:trans isomers, diagnostic peaks 500 MHz 1H NMR (CDCl3) δ 7.45–7.38 (m), 7.22–7.15 (m), 6.92–6.86 (m), 4.52 (d, J=8.0 Hz, major isomer), 4.33 (d, J=5.8 Hz, minor isomer), 3.99 (s, major isomer), 3.97 (s, minor isomer), 3.93 (s), 3.67–3.54 (m, major isomer), 3.44–3.33 (m, minor isomer), 2.82 (bm), 2.80–2.70 (m), 2.47 (dddd, J=2.5, 2.5, 2.5, 2.5 Hz), 2.33–2.23 (m), 1.99–1.88 (m); cis:trans isomers, diagnostic peaks 100 MHz 13C NMR (CDCl3) δ 162.1, 146.9, 131.0, 130.3, 129.0, 127.1, 121.7, 70.6, 59.1, 54.7, 53.7, 53.4, 36.5, 36.1, 32.7, 31.3, 30.5, 30.1, 28.5, 23.4; LRMS m/z Calcd for C21H27N3O2 353.463; obsd LRMS (M+1) 354.4.

EXAMPLE 45

1-{4-[3-(2-Bromo-benzyloxymethyl)-cyclobutyl]-benzyl}-pyrrolidine

Preparation as described for Example 10, General Procedure A, Step G.
Rt=4.75 min HPLC method A; LRMS m/z Calcd for C23H28BrNO 414.39; obsd LRMS (M+2) 416.04.

EXAMPLE 46

2,4-Dimethoxy-6-[3-(4-pyrrolidin-1-ylmethyl-phenyl)-cyclobutylmethoxy]-pyrimidine Preparation as described for Example 36, General Procedure A, Step G using the appropriate starting materials.
Rf=0.3 (10% MeOH/CH2Cl2 w/0.2% NH4OH); cis:trans isomers, diagnostic peaks 400 MHz 1H NMR (CDCl3) δ 7.49–7.43 (m), 7.25–7.18 (m), 4.02 (bs), 3.68–3.56 (m, major isomer), 3.44–3.34 (m, minor isomer), 3.07 (bs), 2.33–2.22 (m), 2.05–1.98 (m); cis:trans isomers, diagnostic peaks 100 MHz 13C NMR (CDCl3) δ 173.0, 147.5, 130.6, 127.3, 70.1, 58.6, 53.1, 36.5, 31.4, 31.2, 28.9, 23.3; LRMS m/z Calcd for C22H29N3O3 383.489; obsd LRMS (M+1) 384.4

EXAMPLE 47 AND EXAMPLE 48

Separation of the cis:trans isomers of Example 4 (General procedure A, Step G) was accomplished by preparative HPLC using a 10 cm×25 cm Chiralpak AD column, eluting with 85/15 heptane/EtOH at a flow rate of 275 mL/min. Sample information: load/injection 1.8 grams, solubility: 1.8 g/10 mL (4:1 MeOH/CH$_2$Cl$_2$).

EXAMPLE 47 cis-Toluene-4-sulfonic acid 3-(4-pyrrolidin-1-ylmethyl-phenyl)-cyclobutylmethyl ester Analytical Rt=8.5 min, UV max 250 (Chiralpak AD, 4.6×250 mm, 85/15 heptane/ethanol with 0.25% DEA, 1 mL/min); Rf=0.35 (10% MeOH/CH2Cl2 w/0.2% NH4OH); 400 MHz 1H NMR (CDCl3) δ 7.77 (d, J=8.3 Hz, 2H), 7.31 (d, J=9.9 Hz, 2H), 7.22 (d, J=7.9 Hz, 2H), 7.06 (d, J=7.9 Hz, 2H), 3.98 (d, J=6.2 Hz, 2H), 3.56 (s, 2H), 3.39–3.30 (m, 1H), 2.61–2.52 (m, 1H), 2.50–2.44 (m, 4H), 2.41 (s, 3H), 2.40–2.35 (m, 2H), 1.86–1.77 (m, 2H), 1.76–1.69 (m, 4H); 100 MHz 13C NMR (CDCl3) δ 145.0, 143.7, 137.4, 133.4, 130.1, 129.1, 128.1, 126.4, 74.2, 60.6, 54.4, 35.9, 32.5, 30.3, 23.7, 21.9; LRMS m/z Calcd for C23H29NO3S 399.552; obsd LRMS (M+1) 400.3.

EXAMPLE 48 trans-Toluene-4-sulfonic acid 3-(4-pyrrolidin-1-ylmethyl-phenyl)-cyclobutylmethyl ester Analytical Rt=12.9 min, UV max 250 ((Chiralpak AD, 4.6×250 mm, 85/15 heptane/ethanol with 0.25% DEA, 1 mL/min)); Rf=0.35 (10% MeOH/CH2Cl2 w/0.2% NH4OH); 400 MHz 1H NMR (CDCl3) δ 7.82 (d, J=8.1 Hz, 2H), 7.35 (d, J=7.8 Hz, 2H), 7.25 (d, J=8.2 Hz, 2H), 7.12 (d, J=8.2 Hz, 2H), 4.18 (d, J=7.4 Hz, 2H), 3.57 (s, 2H), 3.56–3.47 (m, 1H), 2.66–2.56 (m, 1H), 2.51–2.46 (m, 4H), 2.44 (s, 3H), 2.30–2.10 (m, 2H), 2.20–2.12 (m, 2H), 1.80–1.70 (m, 4H); 100 MHz 13C NMR (CDCl3) δ 145.0, 144.1, 137.4, 133.4, 130.1, 129.1, 128.1, 126.4, 73.9, 60.6, 54.4, 36.1, 32.1, 30.9, 23.7, 14.4; LRMS m/z Calcd for C23H29NO3S; 399.552 obsd LRMS (M+1) 400.3.

EXAMPLE 49

General Procedure A

Step F trans-[3-(4-Pyrrolidin-1-ylmethyl-phenyl)-cyclobutyl]-methanol

To a stirring solution of: trans-toluene-4-sulfonic acid 3-(4-pyrrolidin-1-ylmethyl-phenyl)-cyclobutylmethyl ester (example 48) (0.5 g, 1.2 mmol) in methyl alcohol (12.5 mL) was added magnesium turning. After 16 hours the reaction turned from a colorless solutions to a milky white solution. The reaction was quenched by the addtion of 1 mL of an aqueous solution of 15% NaOH and water. The solids were filtered off through a plug of celiteand the aqueous layer was extracted with 3:1 CH3Cl:isopropyl alcohol. The combined organic layer were dried over MgSO4, filtered through a fritted funnel and concentrated under reduced pressure to yield the title compound (242 mg, 79% yield) as a colorless oil. This material was processed without further purification.

Rf=0.26 (10% MeOH/CH2Cl2 w/0.1% NH4OH; mono HCl salt 500 MHz 1H NMR (CD3OD) δ 7.45 (d, 8.3 Hz, 2H), 7.37 (d, J=8.3 Hz, 2H), 4.34 (s, 2H), 3.71 (d, J=7.0 Hz, 2H0, 3.62 (dddd, J=8.3, 8.3, 8.3, 8.3 Hz, 1H), 3.48–3.44 (m, 2H), 3.21–3.14 (m, 2H), 2.47 (app sep. J=7.0 Hz, 1H), 2.26–2.22 (m, 4H), 2.19–2.15 (m, 2H), 2.05–1.94 (m, 2H); 100 MHz 13C NMR (CDCl3) δ 145.5, 135.9, 129.4, 126.5, 66.5, 60.5, 54.2, 36.6, 33.2, 31.3, 23.5; LRMS m/z Calcd for C16H23NO, 245.364; obsd LRMS (M+1) 246.4.

EXAMPLE 50 cis-[3-(4-Pyrrolidin-1-ylmethyl-phenyl)-cyclobutyl]-methanol

Preparation as described for Example 49, General Procedure A, Step F using Example 47 as the starting materials.

Rf=0.26 (10% MeOH/CH2Cl2 w/0.1% NH4OH); 400 MHz 1H NMR (CDCl3) δ 7.60 (d, J=7.9 Hz, 1H), 7.31 (d, J=7.9 Hz, 2H), 7.16 (d, J=7.9 Hz, 2H), 3.78 (s, 2H), 3.60 (d, J=5.8 Hz, 2H), 3.40 (dddd, J=8.3, 8.3, 8.3, 8.3 Hz, 1H), 2.76 (bs), 2.55–2.43 (m), 1.90–1.81 (m); LRMS m/z Calcd for C16H23NO 245.364; obsd LRMS (M+1) 246.4.

EXAMPLE 51 cis 4,6-Dimethyl-2-[3-(4-pyrrolidin-1-ylmethyl-phenyl)-cyclobutylmethoxy]-pyrimidin Preparation as described for Example 36, General Procedure A, Step G using the appropriate starting materials, and the alcohol Example 50 (cis-[3-(4-Pyrrolidin-1-ylmethyl-phenyl)-cyclobutyl]-methanol).

Rf=0.21 (10% MeOH/CH2Cl2 w/0.1% NH4OH); 500 MHz 1H NMR (CDCl3) δ 7.27 (d, J=7.9 Hz, 2H), 7.16 (d, J=7.9 Hz, 2H), 6.63 (s, 1H), 4.30 (d, J=6.6 Hz, 2H), 3.65 (s, 2H), 3.47–3.37 (m, 1H), 2.82–2.72 (m, 1H), 2.62–2.49 (m, 6H), 2.37 (s, 6H), 2.02–1.97 (m, 2H), 1.83–1.78 (m, 4H); 100 MHz 13C NMR (CDCl3) δ 169.3, 165.3, 145.0, 129.3, 126.6, 114.0, 71.6, 60.2, 54.1, 36.4, 33.2, 30.7, 24.0, 23.5; LRMS m/z Calcd for C22H29N3O 351.491; obsd LRMS (M+1) 352.4.

EXAMPLE 52 cis-2-[3-(4-Pyrrolidin-1-ylmethyl-phenyl)-cyclobutylmethoxy]-pyrimidine

Preparation as described for Example 36, General Procedure A, Step G using the appropriate starting materials, and the alcohol Example 50 (cis-[3-(4-Pyrrolidin-1-ylmethyl-phenyl)-cyclobutyl]-methanol).

Rf=0.39 (10% MeOH/CH2Cl2 w/0.1% NH4OH); 500 MHz 1H NMR (CDCl3) δ 8.48 (d, J=4.9 Hz, 2H), 7.25 (d, J=8.3 Hz, 2H), 7.15 (d, J=7.9 Hz, 2H), 6.90 (t, 1H), 4.33 (d, J=6.2 Hz, 2H), 3.60 (s, 2H), 3.48–3.38 (m, 1H), 2.85–2.72 (m, 1H), 2.60–2.47 (m, 6H), 2.05–1.95 (m, 2H), 1.81–1.72 (m, 4H); 100 MHz 13C NMR (CDCl3) δ 165.6, 159.4, 144.6, 136.4, 129.2, 126.5, 115.1, 71.8, 60.5, 54.2, 36.4, 33.1, 30.5, 23.6; LRMS m/z Calcd for C20H25N3O 323.438; obsd LRMS (M+1) 324.3.

EXAMPLE 53 cis-5-Ethyl-2-[3-(4-pyrrolidin-1-ylmethyl-phenyl)-cyclobutylmethoxy]-pyrimidine

Preparation as described for Example 36, General Procedure A, Step G using the appropriate starting materials, and the alcohol Example 50 (cis-[3-(4-Pyrrolidin-1-ylmethyl-phenyl)-cyclobutyl]-methanol).

Rf=0.24 (10% MeOH/CH2Cl2 w/0.1% NH4OH); 500 MHz 1H NMR (CDCl3) δ8.32 (s, 2H), 7.26 (d, J=8.3 Hz, 2H), 7.16 (d, J=7.9 Hz, 2H), 4.30 (d, J=6.2 Hz, 2H), 3.63 (s, 2H), 3.48–3.37 (m, 1H), 2.84–2.72 (m, 1H), 2.60–2.48 (m, 8H), 2.04–1.94 (m, 2H), 1.84–1.74 (m, 4H), 1.22 (t, 3H); 100 MHz 13C NMR (CDCl3) δ 169.4, 129.4, 126.7, 114.0, 70.7, 60.2, 54.1, 36.6, 31.5, 30.3, 24.1, 23.6; LRMS m/z Calcd for C22H29N3O 351.491; obsd LRMS (M+1) 352.3.

EXAMPLE 54 cis-3-Methyl-6-[3-(4-pyrrolidin-1-ylmethyl-phenyl)-cyclobutylmethoxy]-pyridazine Preparation as described for Example 36, General Procedure A, Step G using the appropriate starting materials, and the alcohol Example 50 (cis-[3-(4-Pyrrolidin-1-ylmethyl-phenyl)-cyclobutyl]-methanol).

Rf=0.46 (10% MeOH/CH2Cl2 w/0.1% NH4OH); 500 MHz 1H NMR (CDCl3) δ 7.32 (d, J=8.3 Hz, 2H), 7.21–7.15 (m, 3H), 6.86 (d, J=9.1 Hz, 1H), 4.43 (d, J=6.2 Hz, 2H)), 3.75 (s, 2H), 3.48–3.36 (m, 1H), 2.84–2.68 (m, 5H), 2.57 (s, 3H), 2.55–2.46 (m, 2H), 2.06–1.95 (m, 2H), 1.90–1.82 (m, 4H); 100 MHz 13C NMR (CDCl3) δ 164.0, 155.3, 145.5, 130.1, 129.6, 129.0, 126.8, 117.7, 70.9, 59.8, 53.9, 36.2, 32.9, 30.6, 23.5, 21.7; LRMS m/z Calcd for C21H27N3O 337.464; obsd LRMS (M+1) 338.4.

EXAMPLE 55 trans-4,6-Dimethyl-2-[3-(4-pyrrolidin-1-ylmethyl-phenyl)-cyclobutylmethoxy]-pyrimidine Preparation as described for Example 36, General Procedure A, Step G using the appropriate starting materials, and the alcohol Example 49 (trans-[3-(4-Pyrrolidin-1-ylmethyl-phenyl)-cyclobutyl]-methanol).

Rf=0.28 (10% MeOH/CH2Cl2 w/0.2% NH4OH); 500 MHz 1H NMR (CDCl3) δ 7.29 (d, J=8.3 Hz, 2H), 7.21 (d, J=7.9 Hz, 2H), 6.66 (s, 1H), 4.49 (d, J=7.5 Hz, 2H), 3.72–3.60 (m, 3H), 2.86–2.72 (m, 1H), 2.64–2.52 (m, 4H), 2.41 (s, 6H), 2.38–2.33 (m, 4H), 1.85–1.78 (m, 4H); 100 MHz 13C NMR (CDCl3) δ 169.4, 129.4, 126.7, 114.0, 70.7, 60.2, 54.1, 36.6, 31.5, 30.3, 24.1, 23.6; LRMS m/z Calcd for C22H29N3O 351.491; obsd LRMS (M+1) 352.4.

EXAMPLE 56 trans-2-[3-(4-Pyrrolidin-1-ylmethyl-phenyl)-cyclobutylmethoxy]-pyrimidine

Preparation as described for Example 36, General Procedure A, Step G using the appropriate starting materials, and the alcohol Example 49 (trans-[3-(4-Pyrrolidin-1-ylmethyl-phenyl)-cyclobutyl]-methanol).

Rf=0.32 (10% MeOH/CH2Cl2 w/0.2% NH4OH); 500 MHz 1H NMR (CDCl3) δ 8.51 (d, J=4.6 Hz, 2H), 7.30 (d, J=8.3 Hz, 2H), 7.20 (d, J=8.3 Hz, 2H), 6.93 (dd, J=2.1, 2.1 Hz, 1H), 4.51 (d, J=7.5 Hz, 2H), 3.72–3.60 (m, 3H), 2.87–2.76 (m, 1H), 2.64–2.56 (m, 4H), 2.38–2.30 (m, 4H), 1.86–1.76 (m, 4H); 100 MHz 13C NMR (CDCl3) δ 165.7, 159.5, 159.4, 145.4, 129.4, 126.7, 115.1, 71.2, 60.2, 54.1, 36.4, 30.1, 23.6; LRMS m/z Calcd for C20H25N3O 323.438; obsd LRMS (M+1) 324.4.

EXAMPLE 57 trans-5-Ethyl-2-[3-(4-pyrrolidin-1-ylmethyl-phenyl)-cyclobutylmethoxy]-pyrimidine Preparation as described for Example 36, General Procedure A, Step G using the appropriate starting materials, and the alcohol Example 49 (trans-[3-(4-Pyrrolidin-1-ylmethyl-phenyl)-cyclobutyl]-methanol).

Rf=0.35 (10% MeOH/CH2Cl2 w/0.2% NH4OH; 500 MHz 1H NMR (CDCl3) δ 8.34 (s, 2H), 7.29 (d, J=8.3 Hz, 2H), 7.19 (d, J=8.3 Hz, 2H), 4.48 (d, J=7.5 Hz, 2H), 3.70–3.62 (m, 3H), 2.86–2.74 (m, 1H), 2.66–2.54 (m, 6H), 2.36–2.32 (m, 4H), 1.86–1.78 (m, 4H), 1.23 (t, 3H); 100 MHz 13C NMR (CDCl3) δ 164.4, 158.7, 145.6, 129.9, 129.4, 126.6, 71.03, 60.2, 54.1, 36.5, 31.5, 30.2, 23.5, 22.9, 15.5; LRMS m/z Calcd for C22H29N3O 351.491; obsd LRMS (M+1) 352.4.

EXAMPLE 58 trans-3-Methyl-6-[3-(4-pyrrolidin-1-ylmethyl-phenyl)-cyclobutylmethoxy]-pyridazine Preparation as described for Example 36, General Procedure A, Step G using the appropriate starting materials, and the alcohol Example 49 (trans-[3-(4-Pyrrolidin-1-ylmethyl-phenyl)-cyclobutyl]-methanol).

Rf=0.35 (10% MeOH/CH2Cl2 w/0.2% NH4OH; 500 MHz 1H NMR (CDCl3) δ 7.24 (d, 7.9 Hz, 2H), 7.20–7.15 (m, 3H), 6.85 (d, J=9.1 Hz, 1H), 4.61 (d, J=7.5 Hz, 2H), 3.70–3.58 (m, 1H), 3.57 (s, 2H), 2.83–2.72 (m, 1H), 2.57 (s, 3H), 2.53–2.44 (m, 4H), 2.38–2.44 (m, 4H), 1.79–1.71 (m, 4H); 100 MHz 13C NMR (CDCl3) δ 164.1, 155.3, 144.9, 136.7, 130.1, 129.2, 126.5, 117.7, 70.7, 60.5, 54.3, 36.6, 31.5, 30.1, 23.6, 21.7; LRMS m/z Calcd for C21H27N3O 337.461; obsd LRMS (M+1) 338.2;

EXAMPLE 59

General Procedure A

Step G cis-5-Methyl-4-piperidin-3-yl-2-[3-(4-pyrrolidin-1-ylmethyl-phenyl)-cyclobutylmethoxy]-pyrimidine Alternative High Through-put Procedure is Described.

The appropriate starting herteroaryl chlorides (0.15 mmol, 3 equiv) were pre-weighed into 2-dram vials. A stock solution of alcohol (Example 50, cis-[3-(4-pyrrolidin-1-ylmethyl-phenyl)-cyclobutyl]-methanol) (0.5 mL, 12.3 mg, 0.05 mmol, 1 equiv) was added to the starting heteroaryl chlorides. To this solution was added a THF solution of KotBu (0.15 mL, 0.15 mmol, 1 N in THF, 3 equiv). The reaction was allowed to shake at room temperature overnight. The reactions were then quenched by the addition of 0.5 ml of MeOH and loaded onto Silicycle SCX SPE cartridge. The cartridge was rinsed with CH2Cl2. Changed vials and eluted with 5 ml of MeOH. Switched to tared vials and eluted with 7.5 ml of 1 N TEA in MeOH. The solvent was removed under reduced pressure. Starting herteroaryl-chlorides containing protecting groups were deprotected by adding 0.5 ml of 1:1 CH2Cl2/TFA and shaking at room temp for –1 hour. Prepared TFA salts of remaining samples. Purification was accomplished using the HPLC reported method. The product containing fractions were compressed into tared vials to yield the title compound.

Rt=6.83 min HPLC method B; LRMS m/z Calcd for C26H36N4O 420.597; obsd LRMS (M+1) 421.59;

EXAMPLE 60 cis-Pyridin-4-yl-{6-[3-(4-pyrrolidin-1-ylmethyl-phenyl)-cyclobutylmethoxy]-pyridazin-3-yl}-amine Preparation as described for Example 59, General Procedure A, Step G.

EXAMPLE 61 cis-2-{[3-(4-Pyrrolidin-1-ylmethyl-phenyl)-cyclobutylmethyl]oxy}-4-trifluoromethyl-pyrimidine Preparation as described for Example 59, General Procedure A, Step G.
Rt=8.69 min HPLC method B; LRMS m/z Calcd for C21H24F3N3O 391.435; obsd LRMS (M+1). 392.4;

EXAMPLE 62 cis-5-Phenyl-2-[3-(4-pyrrolidin-1-ylmethyl-phenyl)-cyclobutylmethoxy]-pyrimidine Preparation as described for Example 59, General Procedure A, Step G.
Rt=4.15 min HPLC method B; LRMS m/z Calcd for C26H29N3O 399.535; obsd LRMS (M+1). 400.25.

EXAMPLE 63 cis-(4-Chloro-phenyl)-{6-[3-(4-pyrrolidin-1-ylmethyl-phenyl)-cyclobutylmethoxy]-pyridazin-3-yl}-methanone Preparation as described for Example 59, General Procedure A, Step G.
Rt=9.49 min HPLC method B; LRMS m/z Calcd for C27H28 LRMS m/z Calcd for ClN3O2 461.99; obsd LRMS (M+1). 462.5;

EXAMPLE 64 cis-1,3-Dimethyl-1-{6-[3-(4-pyrrolidin-1-ylmethyl-phenyl)-cyclobutylmethoxy]-pyridazin-3-yl}-urea Preparation as described for Example 59, General Procedure A, Step G.

EXAMPLE 65 cis-4-Pyrrolidin-3-yl-2-[3-(4-pyrrolidin-1-ylmethyl-phenyl)-cyclobutylmethoxy]-pyrimidine Preparation as described for Example 59, General Procedure A, Step G.
Rt=3.68 min HPLC method B; LRMS m/z Calcd for C24H32N4O 392.544; obsd LRMS (M+1) 393.29.

EXAMPLE 66 cis-4-Methyl-6-pyrrolidin-3-yl-2-[3-(4-pyrrolidin-1-ylmethyl-phenyl)-cyclobutylmethoxy]-pyrimidine Preparation as described for Example 59, General Procedure A, Step G.
Rt=3.73 min HPLC method B; LRMS m/z Calcd for C25H34N4O 406.571;obsd LRMS: (M+1) 407.34.

EXAMPLE 67 cis-4-(3-Chloro-phenyl)-2-[3-(4-pyrrolidin-1-ylmethyl-phenyl)-cyclobutylmethoxy]-quinazoline Preparation as described for Example 59, General Procedure A, Step G.
Rt=4.44 min HPLC method B; LRMS m/z Calcd for C30H30ClN3O 483.00; obsd LRMS (M+1) 484.22.

EXAMPLE 68 cis-3-(3-Chloro-phenyl)-1-methyl-1-{6-[3-(4-pyrrolidin-1-ylmethyl-phenyl)-cyclobutylmethoxy]-pyridazin-3-yl}-urea Preparation as described for Example 59, General Procedure A, Step G.
Rt=4.13 min HPLC method B; LRMS m/z Calcd for $C_{28}H_{32}$ LRMS m/z Calcd for ClN5O2 505.00; obsd LRMS (M+1) 506.23.

EXAMPLE 69 cis-5-(4-Methoxy-phenoxy)-2-[3-(4-pyrrolidin-1-ylmethyl-phenyl)-cyclobutylmethoxy]-pyrimidine Preparation as described for Example 59, General Procedure A, Step G.
Rt=4.17 min HPLC method B; LRMS m/z Calcd for C27H31N3O3 445.56; obsd LRMS (M+1) 446.26.

EXAMPLE 70 cis-4-Pyridin-2-yl-2-[3-(4-pyrrolidin-1-ylmethyl-phenyl)-cyclobutylmethoxy]-quinazoline Preparation as described for Example 59, General Procedure A, Step G.
Rt=4.10 min HPLC method B; LRMS m/z Calcd for C29H30N4O 450.583; obsd LRMS (M+1) 451.26.

EXAMPLE 71 cis-5-(3-Chloro-phenoxy)-2-[3-(4-pyrrolidin-1-ylmethyl-phenyl)-cyclobutylmethoxy]-pyrimidine Preparation as described for Example 59, General Procedure A, Step G.
Rt=4.28 min HPLC method B; LRMS m/z Calcd for C26H28ClN3O2 449.979; obsd LRMS (M+1) 450.23.

EXAMPLE 72 cis-4-Phenyl-6-piperidin-4-yl-2-[3-(4-pyrrolidin-1-ylmethyl-phenyl)-cyclobutylmethoxy]-pyrimidine Preparation as described for Example 59, General Procedure A, Step G.
Rt=3.89 min HPLC method B; LRMS m/z Calcd for C31H38N4O 482.668; obsd LRMS (M+1) 483.33.

EXAMPLE 73 cis-3-(3-Methyl-5-phenyl-pyrazol-1-yl)-6-{[3-(4-pyrrolidin-1-ylmethyl-phenyl)-cyclobutylmethyl]oxy}-pyridazine Preparation as described for Example 59, General Procedure A, Step G.
Rt=4.19 min HPLC method B; LRMS m/z Calcd for C30H33N5O 479.625; obsd LRMS (M+1) 480.29.

EXAMPLE 74

5-Fluoro-4-piperidin-4-yl-2-[3-(4-pyrrolidin-1-ylmethyl-phenyl)-cyclobutylmethoxy]-pyrimidine Preparation as described for Example 59, General Procedure A, Step G.
Rt=3.74 min HPLC method B; LRMS m/z Calcd for C25H33FN4O 424.561; obsd LRMS (M+1) 425.31.

EXAMPLE 75 cis-3-piperazin-1-yl-6-[3-(4-pyrrolidin-1-ylmethyl-phenyl)-cyclobutylmethoxy]-pyridazine Preparation as described for Example 59, General Procedure A, Step G.
Rt=3.65 min HPLC method B; LRMS m/z Calcd for C24H33N5O 407.559; obsd LRMS (M+1) 408.32.

EXAMPLE 76 cis-4-Phenyl-2-{[3-(4-pyrrolidin-1-ylmethyl-phenyl)-cyclobutylmethyl]oxy}-6-trifluoromethyl-pyrimidine Preparation as described for Example 59, General Procedure A, Step G.
Rt=4.41 min HPLC method B; LRMS m/z Calcd for C27H28F3N3O 467.532; obsd LRMS (M+1). 468.24

EXAMPLE 77 cis-4-Methyl-6-piperidin-4-yl-2-[3-(4-pyrrolidin-1-ylmethyl-phenyl)-cyclobutylmethoxy]-pyrimidine Preparation as described for Example 59, General Procedure A, Step G.
Rt=3.72 min HPLC method B; LRMS m/z Calcd for C26H36N4O 420.597; obsd LRMS (M+1) 421.33.

EXAMPLE 78 cis-1-Methyl-4-[3-(4-pyrrolidin-1-ylmethyl-phenyl)-cyclobutylmethoxy]-phthalazine Preparation as described for Example 59, General Procedure A, Step G.
Rt=3.73 min HPLC method B; LRMS m/z Calcd for C25H29N3O 387.524; obsd LRMS (M+1) 388.26.

EXAMPLE 79 cis-2-[3-(4-Pyrrolidin-1-ylmethyl-phenyl)-cyclobutylmethoxy]-4-o-tolyl-pyrimidine Preparation as described for Example 59, General Procedure A, Step G.
Rt=4.17 min HPLC method B; LRMS m/z Calcd for C27H31N3O 413.562; obsd LRMS (M+1) 414.31.

EXAMPLE 80 cis-5-(5-Iodo-2-methoxy-benzyl)-3-{[3-(4-pyrrolidin-1-ylmethyl-phenyl)-cyclobutyl]methoxy}-pyridazine Preparation as described for Example 59, General Procedure A, Step G.
Rt=4.13 min HPLC method B; LRMS m/z Calcd for C28H32IN3O2 569.48; obsd LRMS (M+1) 570.21.

EXAMPLE 81 cis-5-Methyl-4-piperidin-4-yl-2-[3-(4-pyrrolidin-1-ylmethyl-phenyl)-cyclobutylmethoxy]-pyrimidine Preparation as described for Example 59, General Procedure A, Step G.
Rt=3.73 min HPLC method B; LRMS m/z Calcd for C26H36N4O 420.597; obsd LRMS (M+1) 421.35.

EXAMPLE 82 cis-4-(2-Methyl-2H-pyrazol-3-yl)-2-[3-(4-pyrrolidin-1-ylmethyl-phenyl)-cyclobutylmethoxy]-quinazoline Preparation as described for Example 59, General Procedure A, Step G.
Rt=4.08 min HPLC method B; LRMS m/z Calcd for C28H31N5O 453.587; obsd LRMS (M+1) 454.30.

EXAMPLE 83 cis-6-Methyl-2[3-(4-pyrrolidin-1-ylmethyl-phenyl)-cyclobutylmethoxy]-pyrimidine-4-carboxylic acid phenylamide Preparation as described for Example 59, General Procedure A, Step G.
Rt=4.18 min HPLC method B; LRMS m/z Calcd for C28H32N4O2 456.587; obsd LRMS (M+1) 457.27.

EXAMPLE 84 cis-4-Phenyl-2-[3-(4-pyrrolidin-1-ylmethyl-phenyl)-cyclobutylmethoxy]-pyrimidine Preparation as described for Example 59, General Procedure A, Step G.
Rt=4.13 min HPLC method B; LRMS m/z Calcd for C26H29N3O 399.535; obsd LRMS (M+1) 400.29.

EXAMPLE 85 cis-3-(2-Methoxy-benzyl)-6-[3-(4-pyrrolidin-1-ylmethyl-phenyl)-cyclobutylmethoxy]-pyridazine Preparation as described for Example 59, General Procedure A, Step G.
Rt=3.93 min HPLC method B; LRMS m/z Calcd for $C_{28}H_{33}N_3O_2$ 443.588; obsd LRMS (M+1) 444.29.

EXAMPLE 86 cis-Dimethyl-{6-[3-(4-pyrrolidin-1-ylmethyl-phenyl)-cyclobutylmethoxy]-pyridazin-3-yl}-amine Preparation as described for Example 59, General Procedure A, Step G.
Rt=3.67 min HPLC method B; LRMS m/z Calcd for $C_{22}H_{30}N_4O$ 366.506; obsd LRMS (M+1) 367.27.

EXAMPLE 87 cis-4-Methyl-6-phenyl-2-[3-(4-pyrrolidin-1-ylmethyl-phenyl)-cyclobutylmethoxy]-pyrimidine Preparation as described for Example 59, General Procedure A, Step G.
Rt=4.15 min HPLC method B; LRMS m/z Calcd for $C_{27}H_{31}N_3O$ 413.562; obsd LRMS (M+1) 414.30.

EXAMPLE 88 cis-5-Methyl-4-pyrrolidin-3-yl-2-[3-(4-pyrrolidin-1-ylmethyl-phenyl)-cyclobutylmethoxy]-pyrimidine Preparation as described for Example 59, General Procedure A, Step G.
Rt=3.72 min HPLC method B; LRMS m/z Calcd for $C_{25}H_{34}N_4O$ 406.571; obsd LRMS (M+1) 407.32.

EXAMPLE 89 cis-3-(3,5-Dimethyl-pyrazol-1-yl)-6-{[3-(4-pyrrolidin-1-ylmethyl-phenyl)-cyclobutylmethyl]oxy}-pyridazine Preparation as described for Example 59, General Procedure A, Step G.
Rt=4.06 min HPLC method B; LRMS m/z Calcd for $C_{25}H_{31}N_5O$ 417.554; obsd LRMS (M+1) 418.29.

EXAMPLE 90 cis-3-(2,5-Dimethyl-pyrrol-1-yl)-6-{[3-(4-pyrrolidin-1-ylmethyl-phenyl)-cyclobutylmethyl]oxy}-pyridazine Preparation as described for Example 59, General Procedure A, Step G.
Rt=4.13 min HPLC method B; LRMS m/z Calcd for $C_{26}H_{32}N_4O$ 416.566; obsd LRMS (M+1) 417.28.

EXAMPLE 91 cis-5-(3-Chloro-phenyl)-2-[3-(4-pyrrolidin-1-ylmethyl-phenyl)-cyclobutylmethoxy]-pyrimidine Preparation as described for Example 59, General Procedure A, Step G.
Rt=4.24 min HPLC method B; LRMS m/z Calcd for $C_{26}H_{28}ClN_3O$ 433.98; obsd LRMS (M+1) 434.23.

EXAMPLE 92 cis-5-(4-Methoxy-phenyl)-2-[3-(4-pyrrolidin-1-ylmethyl-phenyl)-cyclobutylmethoxy]-pyrimidine Preparation as described for Example 59, General Procedure A, Step G.
Rt=4.14 HPLC method B; LRMS m/z Calcd for $C_{27}H_{31}N_3O_2$ 429.561; obsd LRMS (M+1) 430.29.

EXAMPLE 93 cis-4-Phenyl-6-pyridin-2-yl-2-[3-(4-pyrrolidin-1-ylmethyl-phenyl)-cyclobutylmethoxy]-pyrimidine Preparation as described for Example 59, General Procedure A, Step G.
Rt=4.26 min HPLC method B; LRMS m/z Calcd for $C_{31}H_{32}N_4O$ 476.621; obsd LRMS (M+1) 477.29.

EXAMPLE 94 cis-4-Phenyl-6-piperidin-3-yl-2-[3-(4-pyrrolidin-1-ylmethyl-phenyl)-cyclobutylmethoxy]-pyrimidine Preparation as described for Example 59, General Procedure A, Step G.
Rt=3.89 min HPLC method B; LRMS m/z Calcd for $C_{31}H_{38}N_4O$ 482.668; obsd LRMS (M+1) 483.33.

EXAMPLE 95

General Procedure A

Step H:

2-{4-[3-(4-Pyrrolidin-1-ylmethyl-phenyl)-cyclobutylmethyl]-piperazin-1-yl}-pyrimidine To a stirring solution of toluene-4-sulfonic acid 3-(4-pyrrolidin-1-ylmethyl-phenyl)-cyclobutylmethyl ester (159.9 mg, 0.40 mmol) prepared above (Example 4, General Procedure A, Step G) in 2 mL of THF was added 1-(2-pyrimidyl)piperizine (136.2 mg, 0.8 mmol) followed by a solution of KOtBu (136 uL, 0.8 mmol, 1M THF). The reaction was heated to 70 □C (oil bath). After 1 hour DMF (1 mL) was added along with $K_2CO_3$ (2 eq). The reaction was then heated to 100 □C. After 3 hours the reaction was cooled to rt and concentrated under reduced pressure. The resulting mixture was diluted with $CH_2Cl_2$, quenched with a saturated aqueous solution of $NaHCO_3$. The two layers were separated and the aqueous layer was back extracted with 3:1 chloroform:isopropyl alcohol. The combined organic layers were dried over $MgSO_4$, filtered through a fritted funnel and concentrated under reduced pressure. Purification of this material was accomplished by flash column chromatography using a 10 g ISCO column, eluting with a gradient of 5%, 10%, 20% MeOH/CH$_2$Cl$_2$ w/0.1% NH$_4$OH. The product containing fractions were collected and concentrated under reduced pressure to give the title compound (70.0 mg, 44%) as a colorless oil, and a mixture of cis:trans isomers. The bis-HCl salt was generated by dissolving the title compound in EtOAc and then a solution of HCl (2 eq, 1M HCl, THF) was added. The colorless solid was collected and dried under reduced pressure.

Rf=0.44 (20% MeOH/CH$_2$Cl$_2$ w/0.1% NH4OH; diagnostic peaks, cis:trans isomers400 MHz 1H NMR (CDCl3) δ 8.28 (d, J=5.0 Hz), 6.45 (dd, J=5.0, 5.0 Hz), 3.60–3.51 (m), 3.35–3.40 (m); diagnostic peaks; cis:trans isomers 13C NMR 125 MHz (CDCl3) δ 157.9, 129.3, 109.9, 65.6, 43.8, 23.5; LRMS m/z Calcd for C24H33N5 391.56; obsd LRMS (M+1) 392.5.

EXAMPLE 96

Dimethyl-[3-(4-pyrrolidin-1-ylmethyl-phenyl)-cyclobutylmethyl]-amine

Preparation as described for Example 95, General Procedure A, Step H.

Rf=0.43 (20% MeOH/CH2Cl2 w/0.1% NH4OH); LRMS m/z Calcd for C18H28N2 272.433; obsd LRMS (M+1) 273.4.

EXAMPLE 97

1-{4-[3-(4-Pyrrolidin-1-ylmethyl-phenyl)-cyclobutylmethyl]-piperazin-1-yl}-ethanone Preparation as described for Example 95, General Procedure A, Step H.

Rf=0.11 (20% MeOH/CH2Cl2 w/0.1% NH4OH); LRMS m/z Calcd for C22H33N3O 355.523; obsd LRMS (M+1) 356.4.

EXAMPLE 98

4-[3-(4-Pyrrolidin-1-ylmethyl-phenyl)-cyclobutylmethyl]-morpholine

Preparation as described for Example 95, General Procedure A, Step H.

Rf=0.25 (15% MeOH/CH2Cl2 w/0.1% NH4OH); LRMS m/z Calcd for C20H30N2O 314.47; obsd LRMS (M+1) 315.4.

EXAMPLE 99

5-Fluoro-2-{4-[3-(4-pyrrolidin-1-ylmethyl-phenyl)-cyclobutylmethyl]-piperazin-1-yl}-pyrimidine Preparation as described for Example 95, General Procedure A, Step H.

Rf=0.11 (10% MeOH/CH2Cl2 w/0.1% NH4OH; 3:1 (cis:trans) 400 MHz 1H NMR (CDCl3) δ diagnostic peaks 8.17 (s), 3.60–3.51 (m), 3.42–3.35 (m); 3:1 (cis:trans) 125 Mz 13C NMR (CDCl3) δ diagnostic peaks 159.1, 153.0, 150.5, 145.4, 126.6, 64.6, 23.6; LRMS m/z Calcd for C24H32FN5 409.55; obsd LRMS (M+1) 410.4;

EXAMPLE 100

General Procedure A

Step H cis-4-[3-(4-Pyrrolidin-1-ylmethyl-phenyl)-cyclobutylmethyl]-morpholine

To a stirring cis-toluene-4-sulfonic acid 3-(4-pyrrolidin-1-ylmethyl-phenyl)-cyclobutylmethyl ester (example 47) (0.41 g, 1.0 mmol) in DMA (5 mL) was added an amine for example morpholine (0.18 g, 2 mmo). The reaction was then heated to 100° C. (oil bath). After 4 hr the reaction was cooled to rt and concentrated under reduced pressure. Purification of this material was accomplished by flash column chromatography, using a 45 g ISCO column, eluting with a gradient of 5%, 10%, 20%, 60% MeOH/CH$_2$Cl$_2$ with 0.1% NH$_4$OH. The product containing fractions were collected and concentrated to yield the title compound (214 mg) as the TsOH salt. This material was free based by stirring in solid K$_2$CO$_3$ and MeOH for 2 hours. After 2 hr the methanolic solution was concentrated, diluted with CH$_2$Cl$_2$, filtered, and concentrated under reduced pressure to give the free base. The HCl salt was made by taken the freebase up in EtOAc and then adding a solution of HCl (2 eq, 1 M HCl, THF) to give a colorless solid.

Rf=0.48 (10% MeOH/CH2Cl2 w/0.1% NH4OH); 400 MHz 1H NMR (CDCl3) δ 7.23 (d, J=7.9 Hz, 2H), 7.11 (d, J=7.9 Hz, 2H), 3.70–3.65 (m, 4H), 3.56 (s, 2H), 3.41–3.34 (m, 1H), 2.53–2.36 (m, 13H), 1.81–0.174 (m, 6H); 100 MHz 13C NMR (CDCl3) δ 144.4, 137.0 129.0, 126.3, 67.2, 65.9, 60.7, 54.4, 54.1, 36.7, 35.9, 29.8, 23.6; LRMS m/z Calcd for C20H30N2O 314.47; obsd LRMS (M+1) 315.3.

EXAMPLE 101 cis-1-[3-(4-Pyrrolidin-1-ylmethyl-phenyl)-cyclobutylmethyl]-piperazine

Preparation as described for Example 100, General Procedure A, Step H.

Rf=0.14 (20% MeOH/CH2Cl2 w/0.1% NH4OH; 400 MHz 1H NMR (CDCl3) δ 7.21 (d, J=8.3 Hz, 2H), 7.08 (d, J=8.9 Hz, 2H), 4.57 (bs, 1H) 3.56 (s, 2H), 3.39–3.29 (m, 1H), 2.94–2.92 (m 4H), 2.49–2.40 (m, 13H), 1.79–1.70 (m, 6H); LRMS m/z Calcd for C20H31N3, 313.486; obsd LRMS (M+1) 314.3.

EXAMPLE 102 cis-5-Fluoro-2-{4-[3-(4-pyrrolidin-1-ylmethyl-phenyl)-cyclobutylmethyl]-piperazin-1-yl}-pyrimidine Preparation as described for Example 100, General Procedure A, Step H.

Rf=0.27 (10% MeOH/CH2Cl2); 400 MHz 1H NMR (CDCl3) s 8.17 (s, 2H), 7.24 (d, J=7.9 Hz, 2H), 7.12 (d, J=7.9 Hz, 2H), 3.77–3.74 (m, 4H), 3.59 (s, 2H), 3.42–3.33 (m, 1H), 2.54–2.46 (m, 13H), 1.81–1.75 (m, 6H); 100 MHz 13C NMR (CDCl3) δ 159.1, 153.0, 150.5, 145.4, 145.2, 144.6, 136.7, 129.1, 126.4, 65.6, 60.6, 54.3, 53.3, 44.5, 35.9, 30.0, 23.6; LRMS m/z Calcd for C24H32FN5 409.55; obsd LRMS (M+1) 410.4.

EXAMPLE 103 cis-1-[3-(4-Pyrrolidin-1-ylmethyl-phenyl)-cyclobutylmethyl]-pyrrolidine

Preparation as described for Example 100, General Procedure A, Step H.

Rf=0.2 (15% MeOH/CH2Cl2 w/0.1% NH4OH); 400 MHz 1H NMR (CDCl3) δ 7.22 (d, J=7.9 Hz, 2H), 7.11 (d, J=7.9 Hz, 2H), 3.56 (s, 2H), 3.39–3.30 (m, 1H), 2.52–2.48 (bm, 13H), 1.81–1.71 (bm, 10H); 100 MHz 13C NMR (CDCl3) δ 144.7, 136.8, 129.0, 126.4, 63.2, 60.6, 54.7, 54.3, 36.5, 35.7, 31.5, 23.6; LRMS m/z Calcd for C20H30N2 298.471; obsd LRMS (M+1) 299.4.

EXAMPLE 104 cis-1-[3-(4-Pyrrolidin-1-ylmethyl-phenyl)-cyclobutylmethyl]-piperidine

Preparation as described for Example 100, General Procedure A, Step H.

Rf=0.28 (15% MeOH/CH2Cl2 w/0.1% NH4OH); 400 MHz 1H NMR (CDCl3) δ 7.22 (d, J=7.9 Hz, 2H), 7.10 (d, J=7.9 Hz, 2H), 3.56 (s, 2H), 3.38–3.29 (m, 1H), 2.53–2.30 (m, 13H), 1.80–1.71 (m, 6H), 1.59–1.54 (m, 4H), 1.42–1.40 (m, 2H); 100 MHz 13C NMR (CDCl3) δ 144.7, 136.8, 129.0, 126.4, 66.3, 60.6, 54.9, 54.3, 36.7, 36.2, 30.2, 26.0, 24.5, 23.6; LRMS m/z Calcd for C21H32N2 312.498; obsd LRMS (M+1) 313.4.

EXAMPLE 105 cis-2-{1-[3-(4-Pyrrolidin-1-ylmethyl-phenyl)-cyclobutylmethyl]-pyrrolidin-2-yl}-pyridine Preparation as described for Example 100, General Procedure A, Step H.

Rf=0.25 (15% MeOH/CH2Cl2 w/0.1% NH4OH); LRMS m/z Calcd for C25H33N3 375.557; obsd LRMS (M+1) 376.4.

EXAMPLE 106 cis-(2R,6S)-2,6-Dimethyl-4-[3-(4-pyrrolidin-1-ylmethyl-phenyl)-cyclobutylmethyl]-morpholine Preparation as described for Example 100, General Procedure A, Step H.

Rf=0.29 (10% MeOH/CH2Cl2 w/0.1% NH4OH; 400 MHz 1H NMR (CDCl3) δ 7.25 (d, J=7.9 Hz, 2H), 7.11 (d, J=7.9 Hz, 2H), 3.70–3.62 (m, 2H), 3.57 (s, 2H), 3.34 (dddd, J=7.9, 7.9, 7.9, 7.9 Hz, 1H), 2.70–2.66 (m, 2H), 2.53–2.48 (m, 7H), 2.39–2.35 (m, 2H), 1.80–1.67 (m, 8H), 1.13 (d, J=6.2 Hz, 6H); 100 MHz 13C NMR (CDCl3) δ 144.6, 136.7, 129.1, 126.4, 71.8, 65.5, 60.6, 59.9, 54.3, 36.7, 35.9, 29.8, 23.6, 19.5; LRMS m/z Calcd for C22H34N2O 342.524; obsd LRMS (M+1) 343.4:

EXAMPLE 107 trans-1-[3-(4-Pyrrolidin-1-ylmethyl-phenyl)-cyclobutylmethyl]-pyrrolidine

To a stirring solution of Example 48 (trans-toluene-4-sulfonic acid 3-(4-pyrrolidin-1-ylmethyl-phenyl)-cyclobutylmethyl ester) (200 mg, 0.5 mmol) in DMA (1.5 mL) was added the appropriate amine, for example pyrollidine (84 uL, 1.0 mmol). The reaction was then heated to 110 □C (oil bath). After 12 hr the reaction was cooled to rt and concentrated under reduced pressure. This material was free based by stirring in solid $K_2CO_3$ and MeOH for 2 hours. After 2 hr of stirring silica gel was added to the vessel (dry pack) and the methanolic slurry was concentrated. Purfication of this material was accomplished by flash column chromatography using a 12 g ISCO column, eluting with a gradient of 5%–10% MeOH/$CH_2Cl_2$ with 0.2% $NH_4OH$. The product containing fractions were collected and concentrated to give the title compound as a colorless oil. The HCl salt was made by taken the freebase up in EtOAc and then adding a solution of HCl (2 eq, 1 M HCl, THF) to give a colorless solid.

Rf=0.2 (15% MeOH/CH2Cl2 w/0.1% NH4OH); 500 MHz 1H NMR (CDCl3) δ 7.25 (d, J=7.9 Hz, 2H), 7.18 (d, J=7.9 Hz, 2H), 3.57 (s, 2H), 3.52 (dddd, J=7.9, 7.9, 7.9, 7.9 Hz, 1), 2.66 (d, J=7.5 Hz, 2H), 2.56–2.47 (m, 9H), 2.33–2.25 (m, 2H), 2.21–2.14 (m, 2H), 1.80–1.72 (m, 8H); 100 MHz 13C NMR (CDCl3) δ 145.3, 136.8, 129.1, 126.5, 62.5, 60.6, 54.8, 54.4, 36.5, 33.5, 30.9, 23.6; LRMS m/z Calcd for C20H30N2 298.471; obsd LRMS (M+1) 299.4.

EXAMPLE 108 trans-1-[3-(4-Pyrrolidin-1-ylmethyl-phenyl)-cyclobutylmethyl]-piperidine

Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.25 (15% MeOH/CH2Cl2 w/0.1% NH4OH); 500 MHz 1H NMR (CDCl3) δ 7.25 (d, J=7.9 Hz, 2H), 7.19 (d, J=7.9 Hz, 2H), 3.57 (s, 2H), 3.52 (dddd, J=7.9, 7.9, 7.9, 7.9 Hz, 1H), 2.61–2.13 (m, 15H), 1.80–1.72 (m, 4H), 1.59–1.55 (m, 4H), 1.44–1.41 (m, 2H); 100 MHz 13 C. NMR (CDCl3) δ 145.3, 136.9, 129.1, 126.5, 65.7, 60.7, 55.1, 54.4, 36.5, 34.0, 29.5, 26.1, 24.6, 23.6; LRMS m/z Calcd for C21H32N2 312.498; obsd LRMS (M+1) 313.3.

EXAMPLE 109 trans-2-{1-[3-(4-Pyrrolidin-1-ylmethyl-phenyl)-cyclobutylmethyl]-pyrrolidin-2-yl}-pyridine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.3 (15% MeOH/CH2Cl2 w/0.1% NH4OH); 100 MHz 13C NMR (CDCl3) d 164.9, 149.1, 145.3, 136.8, 129.0, 126.4, 122.0, 121.6, 121.3, 71.6, 60.9, 60.6, 54.6, 54.4, 36.3, 34.0, 33.5, 32.9, 30.7, 23.6, 23.4; LRMS m/z Calcd for C25H33N3 375.557; obsd LRMS (M+1) 376.4.

EXAMPLE 110 trans-4-[3-(4-Pyrrolidin-1-ylmethyl-phenyl)-cyclobutylmethyl]-morpholine

Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf 0.25 (15% MeOH/CH2Cl2 w/0.1% NH4OH); 400 MHz 1H NMR (CDCl3) δ 7.25 (d, J=7.9 Hz, 2H), 7.17 (d, J=7.1 Hz, 2H), 3.71–3.66 (m, 4H), 3.57 (bs, 2H), 3.57–3.49 (m, 1H), 2.58–2.38 (m, 11H), 2.30–2.21 (m, 2H), 2.20–2.12 (m, 2H), 1.81–1.69 (bm, 4H); 100 MHz 13C NMR (CDCl3) δ 145.1, 136.9, 129.1, 126.4, 67.2, 64.9, 60.6, 54.4, 54.1, 36.5, 33.5, 28.9, 23.6; LRMS m/z Calcd for C20H30N2O 314.47; obsd LRMS (M+1) 315.2

EXAMPLE 111 trans-1-[3-(4-Pyrrolidin-1-ylmethyl-phenyl)-cyclobutylmethyl]-piperazine-TsOH

Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.15 (20% MeOH/CH2Cl2 w/0.1% NH4OH); 400 MHz 1H NMR (CDCl3) δ 7.70 (d, J=7.9 Hz, 2H), 7.26 (d, J=8.2 Hz, 2H), 7.12–7.09 (m, 4H), 4.60 (bs, 1H), 3.78 (s, 2H), 3.43 (dddd, J=7.9, 7.9, 7.9, 7.9 Hz, 1H), 3.13–3.06 (m, 4H), 2.88–2.68 (m, 4H), 2.56–2.35 (m, 7H) 2.26 (s, 3H), 2.15–2.00 (m, 4H), 1.84–1.78 (m, 4H); mono TsOH salt 100 MHz 13C NMR δ 146.1, 142.0, 140.6, 133.2, 129.8, 129.2, 126.8, 126.1, 63.7, 59.5, 53.9, 50.4, 44.1, 36.3, 33.0, 28.5, 23.3, 21.5; LRMS m/z Calcd for C20H31N3 313.486; obsd LRMS (M+1) 314.4.

EXAMPLE 112 trans-5-Fluoro-2-{4-[3-(4-pyrrolidin-1-ylmethyl-phenyl)-cyclobutylmethyl]-piperazin-1-yl}-pyrimidine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.35 (10% MeOH/CH2Cl2 w/0.1% NH4OH); 500 MHz 1H NMR (CDCl3) δ 8.17 (s, 2H), 7.26 (d, J=8.3 Hz, 2H), 7.19 (d, J=7.9 Hz, 2H), 3.76 (dd, J=5.0, 5.0 Hz, 4H), 3.58 (s, 2H), 3.58–3.51 (m, 1H), 2.61–2.56 (m, 3H), 2.48–2.43 (m, 8H), 2.32–2.15 (m, 4H), 1.78–1.72 (m, 4H); 100 MHz 13C NMR (CDCl3) δ 159.1, (153.0, 150.5), 145.4, 145.2, 136.8, 129.1, 126.5, 64.6, 60.6, 54.4, 53.4, 44.5, 36.5, 33.6, 29.1, 23.6; LRMS m/z Calcd for C24H32FN5 409.55; obsd LRMS (M+1) 410.4.

EXAMPLE 113 trans-2-{Ethyl-[3-(4-pyrrolidin-1-ylmethyl-phenyl)-cyclobutylmethyl]-amino}-ethanol Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.12 (10% MeOH/CH2Cl2 w/0.1% NH4OH); 500 MHz 1H NMR (CDCl3) δ 7.27 (d, J=7.9 Hz, 2H), 7.18 (d, J=8.3 Hz, 2H), 3.58 (s, 2H), 3.58–3.50 (m, 1H), 3.54 (t, J=5.4 Hz, 2H), 3.10 (bs, 1H), 2.65–2.48 (m, 11H), 2.29–2.22 (m, 2H), 2.15–2.09 (m, 2H), 1.79–1.73 (m, 4H), 1.03 (t, J=7.0 Hz, 3H); 100 MHz 13C NMR (CDCl3) δ 145.1, 136.8, 129.1, 126.5, 60.6, 59.1, 58.5, 55.1, 54.4, 47.8, 36.5, 32.8, 29.3, 23.6, 11.9; LRMS m/z Calcd for C20H32N2O 316.486; obsd LRMS (M+1) 317.4.

EXAMPLE 114 trans-3,5-Dimethyl-1-[3-(4-pyrrolidin-1-ylmethyl-phenyl)-cyclobutylmethyl]-piperidine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.15 (10% MeOH/CH2Cl2 w/0.1% NH4OH); LRMS m/z Calcd for C23H36N2 340.551; obsd LRMS (M+1) 341.5.

EXAMPLE 115 trans-Cyclohexyl-methyl-[3-(4-pyrrolidin-1-ylmethyl-phenyl)-cyclobutylmethyl]-amine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.15 (10% MeOH/CH2Cl2 w/0.1% NH4OH); 100 MHz 13C NMR (CDCl3) δ 145.4, 136.9, 129.1, 126.5, 63.4, 60.7, 59.1, 54.4, 38.8, 36.6, 33.3, 29.9, 28.8, 26.7, 26.4, 23.6; LRMS m/z Calcd for C23H36N2 340.551; obsd LRMS (M+1) 341.5.

EXAMPLE 116 trans-Benzyl-methyl-[3-(4-pyrrolidin-1-ylmethyl-phenyl)-cyclobutylmethyl]-amine

Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.5 (10% MeOH/CH2Cl2 w/0.1% NH4OH); 100 MHz 13C NMR (CDCl3) δ 145.2, 139.6, 136.7, 129.3, 129.2, 128.4, 127.1, 126.5, 63.2, 62.9, 60.6, 54.4, 42.8, 36.5, 33.2, 29.5, 23.6; LRMS m/z Calcd for C24H32N2 348.531; obsd LRMS (M+1) 349.4.

EXAMPLE 117 trans-2-Methyl-1-[3-(4-pyrrolidin-1-ylmethyl-phenyl)-cyclobutylmethyl]-piperidine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.15 (10% MeOH/CH2Cl2 w/0.1% NH4OH); LRMS m/z Calcd for C22H34N2 326.525; obsd LRMS (M+1) 327.5.

EXAMPLE 118 trans-3-Methyl-1-[3-(4-pyrrolidin-1-ylmethyl-phenyl)-cyclobutylmethyl]-piperidine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.15 (10% MeOH/CH2Cl2 w/0.1% NH4OH); 100 MHz 13C NMR (CDCl3) δ 145.3, 136.8, 129.1, 126.5, 65.4, 62.6, 60.7, 54.4, 36.4, 33.9, 33.3, 31.3, 29.5, 25.8, 23.6, 20.1; LRMS m/z Calcd for C22H34N2 326.525; obsd LRMS (M+1) 327.5.

EXAMPLE 119 trans-4-Methyl-1-[3-(4-pyrrolidin-1-ylmethyl-phenyl)-cyclobutylmethyl]-piperidine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.15 (10% MeOH/CH2Cl2 w/0.1% NH4OH); 100 MHz 13C NMR (CDCl3) δ 145.3, 136.8, 129.1, 126.5, 65.3, 60.7, 54.3, 36.5, 34.5, 34.0, 31.0, 29.6, 23.6, 22.2; LRMS m/z Calcd for C22H34N2 326.525; obsd LRMS (M+1) 327.5.

EXAMPLE 120 trans-2-Methyl-1-[3-(4-pyrrolidin-1-ylmethyl-phenyl)-cyclobutylmethyl]-pyrrolidine Preparation as described for Example 107, using the appropriate amine and the tosylate Example 48 (trans-toluene-4-sulfonic acid 3-(4-pyrroidin-1-ylmethyl-phenyl)-cyclobutylmethyl ester).

Rf=0.14 (10% MeOH/CH2Cl2 w/0.1% NH4OH); 100 MHz 13C NMR (CDCl3) δ 145.4, 136.8, 129.1, 126.5, 60.7, 54.8, 54.4, 36.5, 33.9, 33.5, 32.2, 30.8, 23.6, 22.0, 19.5; LRMS m/z Calcd for C21H32N2 312.498; obsd LRMS (M+1) 313.5.

EXAMPLE 121 trans-2,6-Dimethyl-1-[3-(4-pyrrolidin-1-ylmethyl-phenyl)-cyclobutylmethyl]-piperidine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.15 (10% MeOH/CH2Cl2 w/0.1% NH4OH); LRMS m/z Calcd for C23H36N2 340.551; obsd LRMS (M+1) 341.5.

EXAMPLE 122 trans-Methyl-pyridin-3-ylmethyl-[3-(4-pyrrolidin-1-ylmethyl-phenyl)-cyclobutylmethyl]-amine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.2 (10% MeOH/CH2Cl2 w/0.1% NH4OH); LRMS m/z Calcd for C23H31N3 349.519; obsd LRMS (M+1) 350.4.

EXAMPLE 123 trans-(2R,5R)-2,5-Dimethyl-1-[3-(4-pyrrolidin-1-ylmethyl-phenyl)-cyclobutylmethyl]-pyrrolidine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.25 (15% MeOH/CH2Cl2 w/0.1% NH4OH); LRMS m/z Calcd for C22H34N2 326.525; obsd LRMS (M+1) 327.5.

EXAMPLE 124 trans-Cyclopropylmethyl-propyl-3-(4-pyrrolidin-1-ylmethyl-phenyl)-cyclobutylmethyl]-amine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.15 (10% MeOH/CH2Cl2 w/0.1% NH4OH); 400 MHz 1H NMR (CDCl3) δ 7.26 (d, J=7.9 Hz, 2H), 7.18 (d, 7.9 Hz, 2H), 3.59 (s, 2H), 3.51 (dddd, J=7.9, 7.9, 7.9, 7.9 Hz, 1H), 2.70 (d, J=7.5 Hz, 2H), 2.58–2.46 (m, 7H), 2.29 (d, J=6.2 Hz, 2H), 2.28–2.13 (m, 4H), 1.80–1.76 (m, 4H), 1.52–1.43 (m, 2H), 0.89–0.83 (m, 4H), 0.51–0.46 (m, 2H), 0.11–0.07 (m, 2H); 100 MHz 13C NMR (CDCl3) δ 145.5, 136.8, 129.1, 126.5, 60.7, 59.9, 59.5, 56.6, 54.4, 36.5, 33.4, 29.5, 23.6, 20.1, 12.2, 8.8, 4.1; LRMS m/z Calcd for C23H36N2 340.551; obsd LRMS (M+1) 341.5.

EXAMPLE 125 trans-2-[3-(4-Pyrrolidin-1-ylmethyl-phenyl)-cyclobutylmethyl]-2,3-dihydro-1H-isoindole Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.35 (10% MeOH/CH2Cl2 w/0.1% NH4OH); 500 MHz 1H NMR (CDCl3) δ 7.31–7.17 (m, 8H), 3.96 (s, 4H), 3.66–3.58 (m, 1H), 3.61 (s, 2H), 2.95 (d, J=7.5 Hz, 2H), 2.66–2.58 (m, 1H), 2.56–2.48 (m, 4H), 2.38–2.24 (m, 4H), 1.84–1.76 (m, 4H); 100 MHz 13C NMR (CDCl3) δ 145.3, 140.4, 136.9, 129.1, 126.9, 126.5, 122.5, 61.9, 60.7, 59.6, 54.4, 36.6, 33.2, 30.8, 23.7; LRMS m/z Calcd for C24H30N2 346.515; obsd LRMS (M+1) 347.5.

EXAMPLE 126 trans-(2R,6S)-2,6-Dimethyl-4-[3-(4-pyrrolidin-1-ylmethyl-phenyl)-cyclobutylmethyl]-morpholine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.35 (10% MeOH/CH2Cl2 w/0.1% NH4OH); 500 MHz 1H NMR (CDCl3) δ 7.26 (d, J=8.3 Hz, 2H), 7.17 (d, J=8.3 Hz, 2H), 3.70–3.64 (m, 2H), 3.57 (s, 2H), 3.53 (dddd, J=7.9, 7.9, 7.9, 7.9 Hz, 1H), 2.70–2.67 (m, 2H), 2.59–2.47 (m, 7H), 2.30–2.12 (m, 4H), 1.79–1.68 (m, 6H), 1.13 (d, J=6.2 Hz, 6H); 100 MHz 13C NMR (CDCl3) δ 145.2, 136.8, 129.1, 126.5, 71.8, 64.6, 60.6, 60.0, 54.3, 36.4, 33.5, 28.9, 23.6, 19.4; LRMS m/z Calcd for C22H34N2O 342.524; obsd LRMS (M+1) 343.5.

EXAMPLE 127 trans-4-[3-(4-Pyrrolidin-1-ylmethyl-phenyl)-cyclobutylmethyl]-piperazin-2-one

Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).
Rf=0.15 (10% MeOH/CH2Cl2 w/0.1% NH4OH); 100 MHz 13C NMR (CDCl3) δ 170.3, 144.9, 136.9, 129.1, 126.4, 63.2, 60.6, 57.2, 54.3, 49.9, 49.5, 43.0, 42.5, 41.4, 36.5, 33.1, 28.8, 23.6; LRMS m/z Calcd for C20H29N3O 327.469; obsd LRMS (M+1) 328.5.

EXAMPLE 128 trans-(S)-2-Methoxymethyl-1-[3-(4-pyrrolidin-1-ylmethyl-phenyl)-cyclobutylmethyl]-pyrrolidine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).
Rf=0.15 (10% MeOH/CH2Cl2 w/0.1% NH4OH); 500 MHz 1H NMR (CDCl3) δ 7.25 (d, J=8.3 Hz, 2H), 7.19 (d, J=8.3 Hz, 2H), 3.58 (s, 2H), 3.51 (dddd, J=7.9, 7.9, 7.9, 7.9 Hz, 1H), 3.42 (dd, J=9.5, 5.0 Hz, 1H), 3.36 (s, 3H), 3.27 (dd, J=9.1, 6.6 Hz, 1H), 3.12–3.02 (m, 2H), 2.61–2.44 (m, 7H), 2.30–2.09 (m, 6H), 1.93–1.84 (m, 1H), 1.80–1.58 (m, 6H); 100 MHz 13C NMR (CDCl3) δ 145.4, 136.8, 129.1, 126.5, 63.9, 61.9, 60.7, 59.4, 55.32, 54.4, 36.5, 33.6, 33.3, 30.9, 28.6, 23.6, 23.3; LRMS m/z Calcd for C22H34N2O 342.524; obsd LRMS (M+1) 343.3.

EXAMPLE 129 trans-(3,5-Bis-trifluoromethyl-benzyl)-{[3-(4-pyrrolidin-1-ylmethyl-phenyl)-cyclobutyl]methyl}-amine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).
Rf=0.72 (20% MeOH/CH2Cl2 w/0.1% NH4OH); 500 MHz 1H NMR (CDCl3) δ 7.84 (bs, 2H), 7.77 (bs, 1H), 7.27 (d, J=8.3 Hz, 2H), 7.18 (d, J=7.9 Hz, 2H), 3.96 (s, 2H), 3.60 (s, 2H), 3.59–3.52 (m, 1H), 2.84 (d, J=7.5 Hz, 2H), 2.55–2.43 (m, 5H), 2.34–2.26 (m, 2H), 2.19–2.11 (m, 2H), 1.83–1.74 (m, 4H); LRMS m/z Calcd for C25H28F6N2 470.498; obsd LRMS (M+1) 471.4.

EXAMPLE 130 trans-(5-Methyl-pyrazin-2-ylmethyl)-[3-(4-pyrrolidin-1-ylmethyl-phenyl)-cyclobutylmethyl]-amine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).
Rf=0.58 (20% MeOH/CH2Cl2 w/0.1% NH4OH); 500 MHz 1H NMR (CDCl3) δ 8.48 (d, J=1.2 Hz, 1H), 8.39 (d, 0.8 Hz, 1H), 7.24 (d, J=8.3 Hz, 2H), 7.16 (d, J=7.9 Hz, 2H), 3.93 (s, 2H), 3.57 (s, 2H), 3.60–3.50 (m, 1H), 2.84 (d, J=7.5 Hz, 2H), 2.54 (s, 3H), 2.52–2.45 (m, 5H), 2.33–2.24 (m 2H), 2.28–2.20 (m, 2H), 1.80–1.72 (m, 2H); LRMS m/z Calcd for C22H30N4 350.507; obsd LRMS (M+1) 351.5;

EXAMPLE 131 trans-(2-Methyl-pyridin-3-ylmethyl)-[3-(4-pyrrolidin-1-ylmethyl-phenyl)-cyclobutylmethyl]-amine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).
Rf=0.13 (20% MeOH/CH2Cl2 w/0.1% NH4OH); 500 MHz 1H NMR (CDCl3) δ 8.39 (dd, J=1.7, 1.7 Hz, 1H), 7.63 (dd, J=1.7, 1.7 Hz, 1H), 7.26 (d, J=7.9 Hz, 2H), 7.18 (d, J=7.9 Hz, 2H), 7.15–7.08 (m, 1H), 3.81 (s, 2H), 3.60 (s, 2H), 3.62–3.52 (m, 1H), 2.86 (d, J=7.5 Hz, 2H), 2.58 (s, 3H), 2.56–2.44 (m, 5H), 2.36–2.25 (m, 2H), 2.19–2.11 (m, 2H), 1.82–1.74 (m, 4H); LRMS m/z Calcd for C23H31N3 349.519; obsd LRMS (M+1) 350.5;

EXAMPLE 132 trans-Pyridin-2-ylmethyl-[3-(4-pyrrolidin-1-ylmethyl-phenyl)-cyclobutylmethyl]-amine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).
Rf=0.28 (20% MeOH/CH2Cl2 w/0.1% NH4OH); 500 MHz 1H NMR (CDCl3) δ 8.56 (dd J=0.8, 0.8 Hz, 1H), 7.65 (ddd, J=2.1, 2.1, 2.1 Hz, 1H), 7.32 (d, J=7.5 Hz, 1H), 7.26 (d, J=7.9 Hz, 2H), 7.17 (d, J=7.9 Hz, 2H), 7.20–7.12 (m, 1H), 3.94 (s, 2H), 3.58 (s, 2H), 3.52–3.50 (m, 1H), 2.86 (d, J=7.5 Hz, 2H), 2.51–2.42 (m, 5H), 2.32–2.24 (m, 2H), 2.20–2.10 (m, 2H), 1.88 (bs, 1H), 1.80–1.72 (m, 4H); LRMS m/z Calcd for C22H29N3 335.492; obsd LRMS (M+1) 336.4;

EXAMPLE 133 trans-2-{4-[3-(4-Pyrrolidin-1-ylmethyl-phenyl)-cyclobutylmethyl]-piperazin-1-yl}-isonicotinonitrile Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).
Rf=0.97 (20% MeOH/CH2Cl2 w/0.1% NH4OH); 500 MHz 1H NMR (CDCl3) δ 8.26 (d, J=5.8 Hz, 1H), 7.28 (d, J=8.3 Hz, 2H), 7.20 (d, J=7.9 Hz, 2H), 6.79 (s, 1H), 6.73 (d, J=6.2 Hz, 1H), 3.62 (s, 2H), 3.60–3.50 (m, 6H), 2.60 (s, 3H), 2.60–2.45 (m, 7H), 2.34–2.15 (m, 4H), 1.85–1.72 (m, 4H); LRMS m/z Calcd for C26H33N5 415.582; obsd LRMS (M+1) 416.5;

EXAMPLE 134 trans-Methyl-pyridin-2-ylmethyl-[3-(4-pyrrolidin-1-ylmethyl-phenyl)-cyclobutylmethyl]-amine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.15 (10% MeOH/CH2Cl2 w/0.1% NH4OH); 500 MHz 1H NMR (CDCl3) δ 8.55–8.52 (m, 1H), 7.67–7.62 (m, 1H), 7.45 (d, J=7.9 Hz, 1H), 7.25 (d, J=7.9 Hz, 2H), 7.17 (d, J=7.9 Hz, 2H), 7.17–7.12 (m, 1H), 3.66 (s, 2H), 3.60 (s, 2H), 3.48 (dddd, J=8.7, 8.7, 8.7, 8.7 Hz, 1H), 2.65–2.46 (m, 7H), 2.26 (s, 3H), 2.25–2.08 (m, 4H), 1.82–1.70 (m, 4H); LRMS m/z Calcd for C23H31N3 349.519; obsd LRMS (M+1) 350.4;

EXAMPLE 135 trans-(3-Chloro-5-trifluoromethyl-pyridin-2-ylmethyl)-{[3-(4-pyrrolidin-1-ylmethyl-phenyl)-cyclobutyl]methyl}-amine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.34 (10% MeOH/CH2Cl2 w/0.1% NH4OH); 500 MHz 1H NMR (CDCl3) δ 8.75 (d, J=0.8 Hz, 1H), 7.89 (d, J=1.7 Hz, 1H), 7.28 (d, J=7.9 Hz, 2H), 7.19 (d, J=8.3 Hz, 2H), 4.13 (s, 2H), 3.63 (s, 2H), 3.53–3.51 (m, 1H), 2.90 (d, J=7.5 Hz, 2H), 2.60–2.48 (m, 5H), 2.36–2.25 (m, 2H), 2.22–2.15 (m, 2H), 1.85–1.75 (m, 4H); LRMS m/z Calcd for C23H27 LRMS m/z Calcd for ClF3N3 437.934; obsd LRMS (M+1) 438.3;

EXAMPLE 136 trans-3-Ethyl-5-{(R)-1-[3-(4-pyrrolidin-1-ylmethyl-phenyl)-cyclobutylmethyl]-pyrrolidin-2-yl}-[1,2,4]oxadiazole Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.55 (10% MeOH/CH2Cl2 w/0.1% NH4OH; 500 MHz 1H NMR (CDCl3) δ 7.26 (d, J=7.9 Hz, 2H), 7.15 (d, J=7.9 Hz, 2H), 3.88 (dd, J=5.8, 5.8 Hz, 1H), 3.60 (s, 2H), 3.53–3.43 (m, 1H), 3.25–3.18 (m, 1H), 2.83–2.77 (m, 2H), 2.75–2.62 (m, 1H), 2.53–2.40 (m, 6H), 2.35–2.00 (m, 8H), 1.95–1.85 (m, 1H), 1.84–1.75 (m, 4H), 1.33 (t, 3H); LRMS m/z Calcd for C24H34N4O 394.56; obsd LRMS (M+1) 395.5.

EXAMPLE 137 trans-(6-Methyl-pyridin-2-ylmethyl)-[3-(4-pyrrolidin-1-ylmethyl-phenyl)-cyclobutylmethyl]-amine Preparation as described for Example 107, using the appropriate amine and the tosylate Example 48 (trans-toluene-4-sulfonic acid 3-(4-pyrrolidin-1-ylmethyl-phenyl)-cyclobutylmethyl ester).

Rf=0.27 (10% MeOH/CH2Cl2 w/0.1% NH4OH); 500 MHz 1H NMR (CDCl3) δ 7.50 (dd, J=7.5, 7.5 Hz, 1H), 7.25 (d, J=7.9 Hz, 2H), 7.17 (d, J=7.9 Hz, 2H), 7.12 (d, J=7.9 Hz, 1H), 7.00 (d, J=7.5 Hz, 1H), 3.89 (s, 2H), 3.58 (s, 2H), 3.60–3.50 (m, 1H), 2.86 (d, J=7.5 Hz, 2H), 2.53 (s, 3H), 2.52–2.45 (m, 5H), 2.32–2.23 (m, 2H), 2.20–2.10 (m, 2H), 1.87 (bs, 1H), 1.80–1.73 (m, 4H); LRMS m/z Calcd for C23H31N3 349.519; obsd LRMS (M+1) 350.2.

EXAMPLE 138

General Procedure A

Step H (Alternative High Speed Synthetic Procedure).

trans-(2-Chloro-6-fluoro-benzyl)-propyl-[3-(4-pyrrolidin-1-ylmethyl-phenyl)-cyclobutylmethyl]-amine To preweighed amines (0.2 mmol, 2 equiv) in a 2-dram vial was added a solution of tosylate of example 48 (trans-toluene-4-sulfonic acid 3-(4-pyrrolidin-1-ylmethyl-phenyl)-cyclobutylmethyl ester) (39.9 mg, 0.1 mmol, 1 equiv) dissolved in 0.4 ml of DMA and then a solution of TEA (0.014 ml, 0.1 mmol, 1 equiv, in 0.1 mL of DMA) was added. The reaction was then heated to 100° C. while being shaken. After heating over night the reactions were concentrated by blowing a stream of nitrogen over vials. The resulting gums were then dissolved in 1 mL of MeOH and K2CO3 (15.2 mg, 0.11 mmol) was added. The resulting slurries were shaken for 30 minutes and then the solvent was removed under reduced pressure. The residual was slurried in CH2Cl2, filtered through an empty SPE cartridge, washed with 2.5 mL of CH2Cl2 and then loaded onto a SCX SPE cartridge. The cartridge was washed with 1.5 mL of CH2Cl2 (discarded), 5 mL of MeOH (discarded) and then the cartridge was washed with 1 N TEA in MeOH into a tared vail. The solvent was removed under reduced pressure and then TFA salts were prepared by dissolving samples in 0.25 mL of CH2Cl2 and adding 0.015 mL TFA/0.5 mL CH2Cl2. The solutions were shaken at room temperature for 15 minutes and then the solvent was removed by blowing a stream of nitrogen over the samples. Purification of the resulting samples was accomplished using the indicated method, the product containing fraction were collected and then concentrating tunder reduced pressure to yield the title compound as the TFA salt.

Rt=4.18 min HPLC method B; LRMS m/z Calcd for C26H34 LRMS m/z Calcd for ClFN2 428.00; obsd LRMS (M+1) 429.25.

EXAMPLE 139 trans-[3-(3,5-Dimethyl-pyrazol-1-yl)-benzyl]-methyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=4.15 min HPLC method B; LRMS m/z Calcd for C29H38N4 442.647; obsd LRMS (M+1) 443.32.

EXAMPLE 140 trans-1-5-Chloro-2-methoxy-benzyl)-4-[3-(4-pyrrolidin-1-ylmethyl-phenyl)-cyclobutylmethyl]-piperazine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=4.10 min HPLC method B; TFA salt 125 MHz 13C NMR (CD3OD) δ 161.6 (q, J (C-F)=35.3 Hz, TFA), 157.3, 147.4, 131.7, 130.7, 130.4, 128.7, 127.2, 125.5, 120.8, 116.8

(q, J (C-F)=291.6 Hz, TFA), 112.6, 61.3, 57.7, 55.3, 54.3, 53.5, 50.1, 49.0, 35.7, 32.2, 26.7, 22.5; LRMS m/z Calcd for C28H38 LRMS m/z Calcd for ClN3O 467.00; obsd LRMS (M+1) 468.26.

EXAMPLE 141 trans-(3S,4aS,8aS)-2-[3-(4-Pyrrolidin-1-ylmethyl-phenyl)-cyclobutylmethyl]-decahydro-isoquinoline-3-carboxylic acid tert-butylamide Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=4.25 min HPLC method B; LRMS m/z Calcd for C30H47N3O 465.721; obsd LRMS (M+1) 466.40.

EXAMPLE 142 trans-(1-Benzyl-piperidin-4-ylmethyl)-methyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.98 min HPLC method B; TFA salt 100 MHz 13C NMR (CD3OD) δ 161.6 (q, J (C-F)=35.3 Hz, TFA), 147.3, 131.2, 130.5, 130.1, 129.2, 129.0, 128.7, 127.2, 116.8 (q, J (C-F)=291.6 Hz, TFA), 61.4, 60.6, 57.7, 53.5, 51.4, 40.1, 35.6, 32.4, 29.4, 27.1, 26.8, 22.6; LRMS m/z Calcd for C30H43N3 445.691; obsd LRMS (M+1) 446.35.

EXAMPLE 143 trans-(S)-1-[3-(4-Pyrrolidin-1-ylmethyl-phenyl)-cyclobutylmethyl]-pyrrolidine-2-carboxylic acid amide Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.80 min HPLC method B; TFA salt 125 MHz 13C NMR (CD3OD) δ 169.8, 161.6 (q, J (C-F)=35.3 Hz, TFA), 147.3, 130.4, 128.7, 127.2, 116.8 (q, J (C-F)=291.6 Hz, TFA), 67.5, 59.9, 57.7, 55.2, 53.5, 35.6, 31.8, 29.5, 28.0, 22.8, 22.6; LRMS m/z Calcd for C21H31N3O 341.496; obsd LRMS (M+1) 342.27.

EXAMPLE 144 trans-(8-Methoxy-quinolin-5-ylmethyl)-methyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.90 min HPLC method B; LRMS m/z Calcd for C28H35N3O 429.604; obsd LRMS (M+1) 430.27.

EXAMPLE 145 trans-4-(4-Chloro-phenoxy)-1-[3-(4-pyrrolidin-1-ylmethyl-phenyl)-cyclobutylmethyl]-piperidine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=4.28 min HPLC method B; LRMS m/z Calcd for C27H35 LRMS m/z Calcd for ClN2O 438.00; obsd LRMS (M+1) 439.24.

EXAMPLE 146 trans-4-(2-Methoxy-phenoxy)-1-[3-(4-pyrrolidin-1-ylmethyl-phenyl)-cyclobutylmethyl]-piperidine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=4.18 min HPLC method B; LRMS m/z Calcd for C28H38N2O2 434.62; obsd LRMS (M+1) 435.30.

EXAMPLE 147 trans-4-(3-Chloro-phenoxy)-1-[3-(4-pyrrolidin-1-ylmethyl-phenyl)-cyclobutylmethyl]-piperidine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=4.32 min HPLC method B; LRMS m/z Calcd for C27H35ClN2O 438.00; obsd LRMS (M+1) 439.26.

EXAMPLE 148 trans-Methyl-(4-phenoxy-benzyl)-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=4.32 min HPLC method B; LRMS m/z Calcd for C30H36N2O 440.627; obsd LRMS (M+1) 441.29.

EXAMPLE 149 trans-[1-(2-Methoxy-ethyl)-piperidin-4-ylmethyl]-methyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.83 min HPLC method B; TFA salt 100 MHz 13C NMR (CD3OD) δ 161.6 (q, J (C-F)=35.3 Hz, TFA), 147.3, 130.5, 128.7, 127.3, 116.8 (q, J (C-F)=291.6 Hz, TFA), 65.6, 61.4, 60.6, 57.7, 56.6, 53.5, 52.2, 40.1, 35.6, 32.3, 29.3, 27.1, 26.8, 22.5; LRMS m/z Calcd for C26H43N3O 413.646; obsd LRMS (M+1) 414.33.

EXAMPLE 150 trans-1-[3-(4-Pyrrolidin-1-ylmethyl-phenyl)-cyclobutylmethyl]-4-#p!-tolyloxy-piperidine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=4.30 min HPLC method B; LRMS m/z Calcd for $C_{28}H_{38}N_2O$ 418.621; obsd LRMS (M+1) 419.31.

EXAMPLE 151 trans-2-{Benzyl-[3-(4-pyrrolidin-1-ylmethyl-phenyl)-cyclobutylmethyl]-amino}-ethanol Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.70 min HPLC method B; LRMS m/z Calcd for $C_{25}H_{34}N_2O$ 378.557; obsd LRMS (M+1) 379.30.

EXAMPLE 152 trans-[2-(3,4-Dimethoxy-phenyl)-ethyl]-methyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.76 min HPLC method B; TFA salt 100 MHz 13C NMR (CD3OD) δ 161.6 (q, J (C-F)=35.3 Hz, TFA), 149.7, 148.6, 147.3, 130.5, 128.9, 128.7, 127.2, 121.1, 116.8 (q, J (C-F)=291.6 Hz, TFA), 112.5, 112.2, 60.7, 57.7, 57.6, 55.3, 53.5, 39.6, 35.7, 32.2, 31.9, 29.7, 26.8, 22.6; LRMS m/z Calcd for $C_{27}H_{38}N_2O_2$ 422.609; obsd LRMS (M+1) 423.28.

EXAMPLE 153 trans-Methyl-prop-2-ynyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.60 min HPLC method B; TFA salt 125 MHz 13C NMR (CD3OD) δ 161.6 (q, J (C-F)=35.3 Hz, TFA), 147.3, 130.5, 128.8, 127.2, 116.8 (q, J (C-F)=291.6 Hz, TFA), 80.3, 71.7, 59.8, 57.7, 53.5, 45.0, 39.6, 35.6, 31.9, 26.8, 22.6; LRMS m/z Calcd for $C_{20}H_{28}N_2$ 296.455; obsd LRMS (M+1) 297.20.

EXAMPLE 154 trans-4-Pyrrolidin-1-yl-1-[3-(4-pyrrolidin-1-ylmethyl-phenyl)-cyclobutylmethyl]-piperidine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.50 min HPLC method B; TFA salt 125 MHz 13C NMR (CD3OD) δ 161.6 (q, J (C-F)=35.3 Hz, TFA), 147.3, 130.5, 128.7, 127.2, 116.8 (q, J (C-F)=291.6 Hz, TFA), 61.5, 58.9, 57.7, 53.5, 52.0, 50.7, 35.6, 32.3, 26.8, 26.2, 22.7, 22.5; LRMS m/z Calcd for $C_{25}H_{39}N_3$ 381.604; obsd LRMS (M+1) 382.34.

EXAMPLE 155 trans-Isopropyl-(2-methoxy-ethyl)-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.62 min HPLC method B; LRMS m/z Calcd for $C_{22}H_{36}N_2O$ 344.539; obsd LRMS (M+1) 345.20.

EXAMPLE 156 trans-1-Benzyl-4-[3-(4-pyrrolidin-1-ylmethyl-phenyl)-cyclobutylmethyl]-piperazine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.63 min HPLC method B; TFA salt 400 MHz 1H NMR (CD3OD) δ7.52–7.35 (m, 9H), 4.33 (s, 2H), 4.19 (s, 2H), 3.72–3.60 (m, 1H), 3.58–3.11 (m, 14H), 2.91–2.79 (m, 1H), 2.46–2.30 (m, 4H), 2.22–2.10 (m, 2H), 2.05–1.92 (m, 2H); TFA salt 125 MHz 13C NMR (CD3OD) δ 161.6 (q, J (C-F)=35.3 Hz, TFA), 147.4, 131.1, 130.6, 130.4, 129.5, 128.9, 128.7, 127.2, 116.8 (q, J (C-F)=291.6 Hz, TFA), 61.2, 60.5, 57.7, 53.5, 49.8, 35.7, 32.2, 26.7, 22.5; LRMS m/z Calcd for $C_{27}H_{37}N_3$ 403.61; obsd LRMS (M+1) 404.33.

EXAMPLE 157 trans-1-Ethyl-4-[3-(4-pyrrolidin-1-ylmethyl-phenyl)-cyclobutylmethyl]-piperazine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.47 min HPLC method B; LRMS m/z Calcd for $C_{22}H_{35}N_3$ 341.539; obsd LRMS (M+1) 342.28.

EXAMPLE 158 trans-2-{Isopropyl-[3-(4-pyrrolidin-1-ylmethyl-phenyl)-cyclobutylmethyl]-amino}-ethanol Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.64 min HPLC method B; LRMS m/z Calcd for $C_{21}H_{34}N_2O$ 330.513; obsd LRMS (M+1) 331.30.

EXAMPLE 159 trans-(2-Methoxy-ethyl)-propyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.63 min HPLC method B; LRMS m/z Calcd for C22H36N2O 344.539; obsd LRMS (M+1) 345.26.

EXAMPLE 160 trans-Methyl-((R)-1-phenyl-ethyl)-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.70 min HPLC method B; LRMS m/z Calcd for C25H34N2 362.558; obsd LRMS (M+1) 363.30.

EXAMPLE 161 trans-(4S,4aS)-4-Phenyl-1-[3-(4-pyrrolidin-1-ylmethyl-phenyl)-cyclobutylmethyl]-decahydro-quinolin-4-ol Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.80 min HPLC method B; LRMS m/z Calcd for C31H42N2O 458.686; obsd LRMS (M+1) 459.33.

EXAMPLE 162 trans-1-{4-[3-(4-Pyrrolidin-1-ylmethyl-phenyl)-cyclobutylmethyl]-piperazin-1-yl}-ethanone Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.57 min HPLC method B; TFA salt 125 MHz 13C NMR (CD3OD) δ 170.6, 161.6 (q, J (C-F)=35.3 Hz, TFA), 147.3, 130.5, 128.7, 127.2, 116.8 (q, J (C-F)=291.6 Hz, TFA), 61.4, 57.7, 53.5, 51.5, 43.0, 38.2, 35.6, 32.2, 26.6, 22.6, 19.7; LRMS m/z Calcd for C22H33N3O 355.523; obsd LRMS (M+1) 356.28.

EXAMPLE 163 trans-1-Methyl-4-[3-(4-pyrrolidin-1-ylmethyl-phenyl)-cyclobutylmethyl]-[1,4]diazepane Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.46 min HPLC method B; TFA salt 125 MHz 13C NMR (CD3OD) δ 161.6 (q, J (C-F)=35.3 Hz, TFA), 147.3, 130.5, 128.7, 116.8 (q, J (C-F)=291.6 Hz, TFA), 62.0, 57.7, 55.5, 53.5, 53.3, 50.4, 43.4, 35.6, 32.0, 26.9, 22.5, 20.6; LRMS m/z Calcd for C22H35N3 341.539; obsd LRMS (M+1) 342.28.

EXAMPLE 164 trans-2-{4-[3-(4-Pyrrolidin-1-ylmethyl-phenyl)-cyclobutylmethyl]-piperazin-1-yl}-nicotinonitrile Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.65 min HPLC method B; LRMS m/z Calcd for C26H33N5 415.582 obsd LRMS (M+1) 416.24.

EXAMPLE 165 trans-Ethyl-(2-methoxy-ethyl)-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.56 min HPLC method B; LRMS m/z Calcd for C21H34N2O 330.513; obsd LRMS (M+1) 331.25.

EXAMPLE 166 trans-Methyl-(3-methyl-pyridin-2-ylmethyl)-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.64 min HPLC method B; TFA salt 100 MHz 13C NMR (CD3OD) δ 161.6 (q, J (C-F)=35.3 Hz, TFA), 148.4, 147.3, 146.4, 138.0, 132.1, 130.5, 128.7, 127.2, 123.8, 116.8 (q, J (C-F)=291.6 Hz, TFA), 61.4, 57.7, 57.5, 53.5, 41.3, 35.7, 32.0, 27.1, 22.6; LRMS m/z Calcd for C24H33N3 363.546; obsd LRMS (M+1) 364.27.

EXAMPLE 167 trans-Diethyl-[3-(4-pyrrolidin-1-ylmethyl-phenyl)-cyclobutylmethyl]-amine

Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.57 min HPLC method B; LRMS m/z Calcd for C20H32N2 300.487; obsd LRMS (M+1) 301.23.

EXAMPLE 168 trans-Benzyl-isopropyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

EXAMPLE 169 trans-(S)-2-Pyrrolidin-1-ylmethyl-1-[3-(4-pyrrolidin-1-ylmethyl-phenyl)-cyclobutylmethyl]-pyrrolidine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.48 min HPLC method B; TFA salt 125 MHz 13C NMR (CD3OD) δ 161.6 (q, J (C-F)=35.3 Hz, TFA), 147.3, 130.5, 128.7, 127.2, 116.8 (q, J (C-F)=291.6 Hz, TFA), 64.2, 58.9, 57.8, 57.7, 55.0, 53.5, 35.6, 32.3, 31.7, 28.7, 28.1, 22.8, 22.5, 21.8; LRMS m/z Calcd for C25H39N3 381.604; obsd LRMS (M+1) 382.30.

EXAMPLE 170 trans-((S)-1-Benzyl-pyrrolidin-3-yl)-ethyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.63 min HPLC method B; LRMS m/z Calcd for C29H41N3 431.664; obsd LRMS (M+1) 432.30.

EXAMPLE 171 trans-tert-Butyl-(2-methoxy-ethyl)-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.60 min HPLC method B; LRMS m/z Calcd for C23H38N2O 358.566; obsd LRMS (M+1) 359.30.

EXAMPLE 172 trans-4-(2-Chloro-phenoxy)-1-[3-(4-pyrrolidin-1-ylmethyl-phenyl)-cyclobutylmethyl]-piperidine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.80 min HPLC method B; TFA salt 125 MHz 13C NMR (CD3OD) δ 161.6 (q, J (C-F)=35.3 Hz, TFA), 152.3, 147.4, 130.5, 128.2, 128.1, 127.2, 124.1, 122.8, 122.6, 116.8 (q, J (C-F)=291.6 Hz, TFA), 116.4, 69.8, 68.3, 61.9, 57.7, 53.5, 40.3, 35.7, 32.2, 26.9, 22.6; LRMS m/z Calcd for C27H35ClN2O 438.00; obsd LRMS (M+1) 439.20.

EXAMPLE 173 trans-N-Ethyl-N,N'-dimethyl-N-[3-(4-pyrrolidin-1-ylmethyl-phenyl)-cyclobutylmethyl]-ethane-1,2-diamine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.51 min HPLC method B; LRMS m/z Calcd for C22H37N3 343.555; obsd LRMS (M+1) 344.28.

EXAMPLE 174 trans-Dicyclopropylmethyl-methyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.68 min HPLC method B; LRMS m/z Calcd for C24H36N2 352.562; obsd LRMS (M+1) 353.28.

EXAMPLE 175 trans-Butyl-methyl-[3-(4-pyrrolidin-1-ylmethyl-phenyl)-cyclobutylmethyl]-amine

Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.62 min HPLC method B; LRMS m/z Calcd for C21H34N2 314.514; obsd LRMS (M+1) 315.26.

EXAMPLE 176 trans-N,N,N'-Trimethyl-N'-[3-(4-pyrrolidin-1-ylmethyl-phenyl)-cyclobutylmethyl]-ethane-1,2-diamine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.56 min HPLC method B; TFA salt 125 MHz 13C NMR (CD3OD) δ 161.6 (q, J (C-F)=35.3 Hz, TFA), 147.3, 130.5, 128.7, 127.2, 116.8 (q, J (C-F)=291.6 Hz, TFA), 61.5, 57.7, 53.5, 51.2, 50.4, 42.8, 39.8, 35.6, 32.0, 26.8, 22.5; LRMS m/z Calcd for C21H35N3 329.528; obsd LRMS (M+1) 330.29.

EXAMPLE 177 trans-1-(1-Methyl-1H-imidazol-2-ylmethyl)-4-[3-(4-pyrrolidin-1-ylmethyl-phenyl)-cyclobutylmethyl]-piperazine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.50 min HPLC method B; TFA salt 125 MHz 13C NMR (CD3OD) δ 161.6 (q, J (C-F)=35.3 Hz, TFA), 147.3, 143.7, 130.5, 128.7, 127.2, 124.5, 118.5 116.8 (q, J (C-F)=291.6 Hz, TFA), 61.3, 57.7, 53.5, 51.8, 50.0, 49.5, 35.6, 33.8, 32.3, 26.6, 22.6; LRMS m/z Calcd for C25H37N5 407.602; obsd LRMS (M+1) 408.32.

EXAMPLE 178 trans-2,5-Dimethyl-1-[3-(4-pyrrolidin-1-ylmethyl-phenyl)-cyclobutylmethyl]-2,5-dihydro-1H-pyrrole Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.59 min HPLC method B; LRMS m/z Calcd for C22H32N2 324.509; obsd LRMS (M+1) 325.26.

EXAMPLE 179 trans-((S)-1-Benzyl-pyrrolidin-3-yl)-methyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.59 min HPLC method B; TFA salt 125 MHz 13C NMR (CD3OD) δ 161.6 (q, J (C-F)=35.3 Hz, TFA), 147.3, 130.5, 130.2, 130.1, 129.2, 128.7, 127.2, 116.8 (q, J (C-F) =291.6 Hz, TFA), 62.8, 59.9, 58.4, 57.7, 53.5, 52.7, 52.2, 37.8, 35.5, 32.0, 26.9, 25.9, 22.5; LRMS m/z Calcd for C28H39N3 417.637; obsd LRMS (M+1) 418.31.

EXAMPLE 180 trans-(4-Fluoro-benzyl)-methyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.67 min HPLC method B; LRMS m/z Calcd for C24H31FN2 366.521; obsd LRMS (M+1) 367.23.

EXAMPLE 181 trans-1-Phenyl-8-[3-(4-pyrrolidin-1-ylmethyl-phenyl)-cyclobutylmethyl]-1,3,8-triaza-spiro[4.5]decan-4-one Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.70 min HPLC method B; LRMS m/z Calcd for C29H38N4O 458.646; obsd LRMS (M+1) 459.26.

EXAMPLE 182 trans-2-{Methyl-[3-(4-pyrrolidin-1-ylmethyl-phenyl)-cyclobutylmethyl]-amino}-ethanol Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.55 min HPLC method B; TFA salt 125 MHz 13C NMR (CD3OD) δ 161.6 (q, J (C-F)=35.3 Hz, TFA), 147.4, 130.5, 128.7, 127.2, 116.8 (q, J (C-F)=291.6 Hz, TFA), 60.7, 57.7, 57.6, 55.1, 53.5, 40.2, 35.7, 32.1, 26.8, 22.6; LRMS m/z Calcd for C19H30N2O 302.459; obsd LRMS (M+1) 303.23.

EXAMPLE 183 trans-3-Benzyl-7-[3-(4-pyrrolidin-1-ylmethyl-phenyl)-cyclobutylmethyl]-5,6,7,8-tetrahydro-[1,2,4]triazolo[4,3-a]pyrazine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.66 min HPLC method C; LRMS m/z Calcd for C28H35N5 441.619; obsd LRMS (M+1) 442.25.

EXAMPLE 184 trans-3-{Benzyl-[3-(4-pyrrolidin-1-ylmethyl-phenyl)-cyclobutylmethyl]-amino}-propan-1-ol Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.65 min HPLC method B; LRMS m/z Calcd for C26H36N2O 392.583; obsd LRMS (M+1) 393.29.

EXAMPLE 185 trans-Isobutyl-methyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.61 min HPLC method B; LRMS m/z Calcd for C21H34N2 314.514; obsd LRMS (M+1) 315.26.

EXAMPLE 186 trans-Ethyl-isopropyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.56 min HPLC method B; LRMS m/z Calcd for C21H34N2 314.514; obsd LRMS (M+1) 315.26.

EXAMPLE 187 trans-Dimethyl-{(R)-1-[3-(4-pyrrolidin-1-ylmethyl-phenyl)-cyclobutylmethyl]-pyrrolidin-3-yl}-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.47 min HPLC method B; LRMS m/z Calcd for C22H35N3 341.539; obsd LRMS (M+1) 342.28.

EXAMPLE 188 trans-Isopropyl-methyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.56 min HPLC method B; LRMS m/z Calcd for C20H32N2 300.487; obsd LRMS (M+1) 301.22.

EXAMPLE 189 trans-Methyl-(5-propyl-1H-pyrazol-3-ylmethyl)-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.65 min HPLC method B; LRMS m/z Calcd for C24H36N4 380.576; obsd LRMS (M+1) 381.30.

EXAMPLE 190

PF-00580378:

trans-(1R,2S)-2-{Methyl-[3-(4-pyrrolidin-1-ylmethyl-phenyl)-cyclobutylmethyl]-amino}-1-phenyl-propan-1-ol Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.70 min HPLC method B; LRMS m/z Calcd for C26H36N2O 392.583; obsd LRMS (M+1) 393.29.

EXAMPLE 191 trans-2-{1-[3-(4-Pyrrolidin-1-ylmethyl-phenyl)-cyclobutylmethyl]-piperidin-4-yl}-benzooxazole Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.70 min HPLC method C; LRMS m/z Calcd for C28H35N3O 429.604; obsd LRMS (M+1) 430.24.

EXAMPLE 192 trans-3-Propyl-7-[3-(4-pyrrolidin-1-ylmethyl-phenyl)-cyclobutylmethyl]-5,6,7,8-tetrahydro-[1,2,4]triazolo[4,3-a]pyrazine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.57 min HPLC method C; LRMS m/z Calcd for C24H35N5 393.575; obsd LRMS (M+1) 394.25.

EXAMPLE 193 trans-Benzyl-((R)-1-phenyl-ethyl)-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.82 min HPLC method B; LRMS m/z Calcd for C31H38N2 438.655; obsd LRMS (M+1) 439.27.

EXAMPLE 194 trans-tert-Butyl-ethyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.61 min HPLC method B; LRMS m/z Calcd for C22H36N2 328.54; obsd LRMS (M+1) 329.25.

EXAMPLE 195 trans-1-Methyl-4-[3-(4-pyrrolidin-1-ylmethyl-phenyl)-cyclobutylmethyl]-piperazine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.55 min HPLC method B; TFA salt 125 MHz 13C NMR (CD3OD) δ 161.6 (q, J (C-F)=35.3 Hz, TFA), 147.6, 130.4, 128.6, 127.2, 116.8 (q, J (C-F)=291.6 Hz, TFA), 61.4, 57.8, 53.5, 51.1, 49.3, 42.4, 35.8, 32.2, 27.0, 22.5 LRMS m/z Calcd for C21H33N3 327.513; obsd LRMS (M+1) 328.29.

EXAMPLE 196 trans-Isopropyl-[3-(4-pyrrolidin-1-ylmethyl-phenyl)-cyclobutylmethyl]-(1,3,5-trimethyl-1H-pyrazol-4-ylmethyl)-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.62 min HPLC method B; LRMS m/z Calcd for C26H40N4 408.63; obsd LRMS (M+1) 409.32.

EXAMPLE 197 trans-4-{Benzyl-[3-(4-pyrrolidin-1-ylmethyl-phenyl)-cyclobutylmethyl]-amino}-butan-1-ol Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.66 min HPLC method B; LRMS m/z Calcd for C27H38N2O 406.61; obsd LRMS (M+1) 407.28.

EXAMPLE 198 trans-(1R,2R)-2-{Methyl-[3-(4-pyrrolidin-1-ylmethyl-phenyl)-cyclobutylmethyl]-amino}-1-phenyl-propan-1-ol Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.69 min HPLC method B; LRMS m/z Calcd for C26H36N2O 392.583; obsd LRMS (M+1) 393.29.

EXAMPLE 199 trans-Benzyl-ethyl-[3-(4-pyrrolidin-1-ylmethyl-phenyl)-cyclobutylmethyl]-amine

Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.68 min HPLC method B; LRMS m/z Calcd for C25H34N2 362.558; obsd LRMS (M+1) 363.31.

EXAMPLE 200 trans-6-{4-[3-(4-Pyrrolidin-1-ylmethyl-phenyl)-cyclobutylmethyl]-piperazin-1-yl}-nicotinonitrile Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.66 min HPLC method B; TFA salt 100 MHz 13C NMR (CD3OD) δ 161.6 (q, J (C-F)=35.3 Hz, TFA), 159.0, 152.4, 147.3, 140.6, 130.5, 128.7, 127.2, 117.8, 116.8 (q, J (C-F)=291.6 Hz, TFA), 106.9, 98.1, 61.4, 57.7, 53.5, 51.4, 41.5, 35.7, 32.2, 26.6, 22.6; LRMS m/z Calcd for C26H33N5 415.582; obsd LRMS (M+1) 416.25.

EXAMPLE 201 trans-Methyl-[3-(4-pyrrolidin-1-ylmethyl-phenyl)-cyclobutylmethyl]-(2-trifluoromethyl-benzyl)-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.73 min HPLC method C; LRMS m/z Calcd for C25H31F3N2 416.528; obsd LRMS (M+1) 417.20.

EXAMPLE 202 trans-3-(3-Methoxy-phenyl)-6-[3-(4-pyrrolidin-1-ylmethyl-phenyl)-cyclobutylmethyl]-5,6,7,8-tetrahydro-4H-1,2,3a,6-tetraaza-azulene Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.64 min HPLC method C; LRMS m/z Calcd for C29H37N5O 471.645; obsd LRMS (M+1) 472.28.

EXAMPLE 203 trans-Methyl-phenethyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.51 min HPLC method B; TFA salt 125 MHz 13C NMR (CD3OD) δ 161.6 (q, J (C-F)=35.3 Hz, TFA), 147.3, 136.3, 130.5, 128.9, 128.7, 128.6, 127.2, 127.1, 116.8 (q, J (C-F)=291.6 Hz, TFA), 60.7, 57.7, 57.5, 53.5, 39.6, 35.6, 32.1, 31.9, 30.1, 26.9, 22.6; LRMS m/z Calcd for C25H34N2 362.558; obsd LRMS (M+1) 363.24.

EXAMPLE 204 trans-3-{Pyridin-2-ylmethyl-[3-(4-pyrrolidin-1-ylmethyl-phenyl)-cyclobutylmethyl]-amino}-propan-1-ol Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.59 min HPLC method B; TFA salt 125 MHz 13C NMR (CD3OD) δ 161.6 (q, J (C-F)=35.3 Hz, TFA), 150.5, 149.5, 147.3, 138.0, 130.3, 128.7, 127.2, 124.2, 123.7, 116.8 (q, J (C-F)=291.6 Hz, TFA), 59.8, 59.1, 57.7, 57.1, 54.3, 53.5, 35.6, 31.8, 30.8, 26.9, 25.7, 22.6; LRMS m/z Calcd for C25H35N3O 393.571; obsd LRMS (M+1) 394.25.

EXAMPLE 205 trans-Bis-pyridin-2-ylmethyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.60 min HPLC method B; LRMS m/z Calcd for C28H34N4 426.605; obsd LRMS (M+1) 427.27.

EXAMPLE 206 trans-Bis-(3-chloro-benzyl)-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).
Rt=3.87 min HPLC method B; LRMS m/z Calcd for C30H34Cl2N2 492.00; obsd LRMS (M+1) 493.16.

EXAMPLE 207 trans-Cyclopropyl-[3-(4-pyrrolidin-1-ylmethyl-phenyl)-cyclobutylmethyl]-(1,3,5-trimethyl-1H-pyrazol-4-ylmethyl)-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.62 min HPLC method B; LRMS m/z Calcd for C26H38N4 406.614; obsd LRMS (M+1) 407.29.

EXAMPLE 208 trans-Methyl-pyridin-4-ylmethyl-[3-(4-pyrrolidin-1-ylmethyl-phenyl)-cyclobutylmethyl]-amine Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.49 min HPLC method C; LRMS m/z Calcd for C23H31N3 349.519; obsd LRMS (M+1) 350.25

EXAMPLE 209 trans-3-(3,4-Difluoro-phenyl)-6-[3-(4-pyrrolidin-1-ylmethyl-phenyl)-cyclobutylmethyl]-5,6,7,8-tetrahydro-4H-1,2,3a,6-tetraaza-azulene Preparation as described for Example 138, using the appropriate amine and the tosylate of example 48 (trans-toluene-4-sulfonic acid 3-(4-pyrrolidin-1-ylmethyl-phenyl)-cyclobutylmethyl ester).

Rt=3.67 min HPLC method C; LRMS m/z Calcd for C28H33F2N5 477.6; obsd LRMS (M+1) 478.23

Intermediate 4—General Procedure B
Step A:

(3,3-Dimethoxy-cyclobutyl)-pyrrolidin-1-yl-methanone

To a stirring solution of 3,3-dimethoxy-cyclobutanecarboxylic acid methyl ester, (J. Org. Chem. 1988, 53, 3841 and J. Org. Chem. 1996, 61, 2174) (1.0 g, 5.7 mmol) in acetonitrile (200 mL) was added pyrrolidine (951 uL, 11.5 mmol), followed by magnesium bromide (0.53 g, 2.9 mmol). The reaction was then heated to 60 □C (oil bath) for 18 hours. After 18 hours a second portion of pyrrolidine (1.9 mL, 23 mmol) and magnesium bromide (0.8 g, 4.3 mmol were added. The reaction was then heated to 80 □C (oil bath) for 48 hours. TLC and MS analysis indicated complete consumption of starting material. The reaction was cooled to room temperature and quenched with a saturated solution of NaHCO$_3$, and diluted with CH$_2$Cl$_2$. The layers were separated and the organic layer was dried over magnesium sulfate, filtered through a fritted funnel and concentrated under reduced pressure. Purification of this material was accomplished by flash column chromatography using a 40M Biotage column, eluting with 70% EtOAc/toluene. The product containing fractions were collected and concentrated under reduced pressure to give the title compound (1.0 g, 86% yield) as a colorless oil.

Rf=0.25 (30% Toluene/EtOAc); 400 MHz 1H NMR (CDCl3) δ 3.40 (dd, J=6.6, 7.1 Hz, 2H), 3.30 (dd, J=6.6, 7.1 Hz, 2H), 3.12 (s, 3H), 3.08 (s, 3H), 2.83 (dddd, J=8.7, 8.7, 8.7, 8.7 Hz, 1H), 2.40–2.26 (m, 4H), 1.87 (dddd, J=7.1, 7.1, 7.1, 7.1 Hz, 2H), 1.78 (dddd, J=6.6, 6.6, 6.6, 6.6 Hz, 2H); 125 MHz 13C NMR (CDCl3) δ 172.2, 99.8, 48.9, 48.6, 46.2, 46.1, 34.9, 29.0, 26.3, 24.7; C11H19NO3 213.275 GC/MS 213, Retention time=3.42 min (Stationary phase: HP-1, fused silica, description: 12 m×0.202 mm×0.33 um. temperature limits: −60 C to 325 C, ramp rate=30 C/min, solvent delay=0.4 min).

Intermediate 5—General Procedure B
Step B:

1-[(3,3-Dimethoxy-cyclobutyl)methyl]-pyrrolidine

To a stirring solution of (3,3-dimethoxy-cyclobutyl)-pyrrolidin-1-yl-methanone (Intermediate 4, General procedure B, Step A) (1.7 g, 8.0 mmol) in THF (50 mL) was added slowly a solution of lithium aluminum hydride (12 mL, 12 mmol, 1M THF). After 30 minutes the reaction was quenched by the dropwise addtion of H$_2$O: 15% NaOH: H$_2$O Fieser and Fieser method). The resulting solids were filtered off using a fritted funnel and celite, and the filter pad was washed with EtOAc. The organic layer was concentrated under reduced pressure to give the title compound (1.6 g, quantitative yield) as a colorless oil. This material was processed without further purification.

400 MHz 1H NMR (CDCl3) δ 3.07 (s, 3H), 3.03 (s, 3H), 2.45–2.35 (m, 6H), 2.29–2.22 (m, 2H), 2.17 (dddd, J=7.1, 7.1, 7.1, 7.1 Hz, 1H), 1.72–1.64 (m ,6H); 100 MHz 13C NMR (CDCl3) δ 100.9, 63.0, 54.6, 48.6, 48.3, 36.9, 24.7, 23.5; C$_{11}$H$_{21}$NO$_2$ $_{199.292}$; GC/MS 199, Retention time=2.05 min (Stationary phase: HP-1, fused silica, description: 12 m×0.202 mm×0.33 um. temperature limits: −60 C to 325 C, ramp rate=30 C/min, solvent delay=0.4 min).

Intermediate 6—General Procedure B
Step C:

3-Pyrrolidin-1-ylmethyl-cyclobutanone

To a stirring solution of 1-[(3,3-dimethoxy-cyclobutyl)methyl]-pyrrolidine (intermediate 5, general prcedure B, step B) (1.6 g, 8.0 mmol) in 3:1 acetone:H$_2$O (100 mL) was added p-toluenesulfonic acid mono hydrate (1.5 g, 8.0 mmol). The reaction mixture was heated to 65 C for 1 hour. Both TLC and GS/MS analysis indicated complete consumption of starting material. The reaction was cooled to room temperature and then the acetone was removed under reduced pressure. The resulting mixture was diluted with CH$_2$Cl$_2$ and washed with an aqueous solution of NaHCO$_3$. The aqueous layer was back extracted with 3:1 CHCl$_3$:isopropyl alcohol. The combined organic layers were dried over magnesium sulfate, filtered through a fritted funnel and then concentrated under reduced pressure to yield the title compound (0.94 g, 76% yield) as a colorless oil. This material was processed without further purification.

400 MHz 1H NMR (CDCl3) δ 3.19–3.10 (m, 2H), 2.85–2.77 (m, 2H), 2.74 (d, 2H), 2.66–2.56 (m, 5H), 1.90–1.77 (m, 4H); 100 MHz 13C NMR (CD3OD) δ 207.9, 61.4, 54.0, 51.2, 29.8, 23.0; C9H15NO 153.223 GC/MS 153, Retention time=1.60 min (Stationary phase: HP-1, fused silica, description: 12 m×0.202 mm×0.33 um. temperature limits: −60 C to 325 C, ramp rate=30 C/min, solvent delay=0.4 min).

Intermediate 7 (General Procedure B)
Step C

3-Piperidin-1-ylmethyl-cyclobutanone

Preparation as described for Intermediate 6 (General procedure B, Steps A–C) using the appropriate starting materials.

Rf=0.30 (10% MeOH/CH2Cl2, 0.1% NH4OH); 500 MHz 1H NMR (CDCl3) δ 3.14–3.04 (m, 2H), 2.76–2.66 (m, 2H), 2.62–2.51 (m, 1H), 2.50–2.44 (m, 2H), 2.43–2.28 (m, 4H), 1.58–1.48 (m, 4H), 1.44–1.34 (m, 2H); 100 MHz 13C NMR (CDCl3) δ 208.4, 65.0, 54.9, 52.2, 26.1, 24.5, 21.9;

C10H17NO 167.25; GC/MS 167, Retention time=1.57 min (Stationary phase: HP-1, fused silica, description: 12 m×0.202 mm×0.33 um. temperature limits: −60 C to 325 C, ramp rate=30 C/min, solvent delay=1.0 min)

EXAMPLE 210

General Procedure B

Step D:

3-Pyrrolidin-1-ylmethyl-1-(4-pyrrolidin-1-ylmethyl-phenyl)-cyclobutanol

To a stirring solution of 1-(4-Bromo-benzyl)-pyrrolidine (Lednicer, Daniel; Lyster, Stanley C.; Duncan, Gordon W. Mammalian antifertility agents. IV. Basic 3,4-dihydronaphthalenes and 1,2,3,4-tetrahydro-1-naphthols. Journal of Medicinal Chemistry (1967), 10(1), 78–84, J. Org. Chem; EN; 46; 17; 1981; 3571–3574) (0.71 g, 2.96 mmol) in THF (13 mL) at −78° C. (isopropanol/$CO_2$) was added a solution of n-butyl lithium (1.6 mL, 3.93 mmol, 2.5 M hexanes). After 15 minutes a pre-cooled (−78 □C) solution of 3-pyrrolidin-1-ylmethyl-cyclobutanone (Intermediate 6, General procedure B Step C) (0.2 g, 1.3 mmol, in 3 mL THF) was added down the side of the flask. After TLC analysis indicated complete consumption of starting material the reaction was quenched cold by the addition of a saturated solution of $NH_4Cl$. The reaction was then warmed to room temperature and diluted with $CH_2Cl_2$. The layers were separated and the aqueous layer was extracted with $CH_2Cl_2$. The combined organic layers were discarded. The aqueous layer was then extracted with 3:1 (CHCl3:isopropyl alcohol) and the combined organic layers were dried over magnesium sulfate, filtered through a fritted funnel, and concentrated under reduced pressure. The material was purified by trituration using ether:hexanes to yield the title compound (0.24 mg, 58% yield) as a colorless solid and a mixture of cis:trans isomers.

Rf=0.22 (20% MeOH/CH2Cl2 w/0.1% NH4OH); cis:trans isomers, diagnostic peaks 400 MHz 1H NMR (CD3OD) δ 7.58 (d, J=7.9 Hz), 3.30–4.10 (m), 2.37–2.25 (m), 2.01–1.91 (m); cis:trans isomers, diagnostic peaks 100 MHz 13C NMR (CD3OD) δ 146.8, 132.7, 130.0, 125.7, 60.6, 58.4, 41.9; LRMS m/z Calcd for C20H30N2O 314.47; obsd LRMS (M+1) 315.2.

EXAMPLE 211

1-(4-Piperidin-1-ylmethyl-phenyl)-3-pyrrolidin-1-ylmethyl-cyclobutanol

Preparation as described for Example 210 using the appropriate starting materials, 3-pyrrolidin-1-ylmethyl-cyclobutanone (Intermediate 6, General procedure, Step C) and PF-549393–00: 1-(4-Bromo-benzyl)-piperidine (Maier, Roland; Woitun, Eberhard; Mueller, Peter; Humaus, Rudolf; Mark, Michael; Eisele, Bernhard; Budzinski, Ralph-Michael. Preparation of N-acylphenylcyclohexylamines as cholesterol biosynthesis inhibitors. Ger. Offen. (1996)).

Rf=0.15 (40% MeOH/CH2Cl2 w/0.1% NH4OH; cis::trans, isomers, diagnostic peaks 500 MHz 1H NMR (CDCl3) δ 7.42 (d, J=6.2 Hz), 4.10 (bs), 3.42 (s), 2.8–2.33 (m); cis:trans isomers, diagnostic peaks 125 MHz 13C NMR (CDCl3) δ 145.1, 137.3, 129.5, 125.1, 124.8, 73.4, 63.7, 62.8, 62.2, 42.5, 41.6, 26.1, 24.5, 23.7, 23.5; LRMS m/z Calcd for C21H32N2O 328.497; obsd LRMS (M+1) 329.4.

EXAMPLE 212

1-(4-Benzyloxymethyl-phenyl)-3-pyrrolidin-1-ylmethyl-cyclobutanol

Preparation as described for Example 210 using the appropriate starting materials, 3-pyrrolidin-1-ylmethyl-cyclobutanone (Intermediate 6, General procedure B, Step C).

Rf=0.15 (25% MeOH/$CH_2Cl2$ w/0.1% NH4OH); cis:trans isomers, diagnostic peaks, 500 Mz 1H NMR (CDCl3) δ 7.47 (d, J=8.3 Hz), 2.65–2.63 (m), 2.50 (d, J=5.4 Hz), 2.40–2.37 (m); cis:trans isomers, diagnostic peaks 125 MHz 13C NMR (CDCl3) δ 146.5, 138.5, 137.0, 128.6, 127.9, 125.6, 125.3, 72.6, 72.1, 72.0, 62.8, 54.7, 43.0, 25.6, 23.6; LRMS m/z Calcd for C23H29NO2 351.4871; obsd LRMS (M+1) 352.2.

EXAMPLE 213

4-(1-Hydroxy-3-pyrrolidin-1-ylmethyl-cyclobutyl)-benzonitrile

Preparation as described for Example 210 using the appropriate starting materials, 3-pyrrolidin-1-ylmethyl-cyclobutanone (Intermediate 6, General procedure B, Step C) and 4-bromo benzonitrile.

Rf=0.12 (25% MeOH/CH2Cl2 w/0.1% NH4OH); cis:trans isomers, diagnostic peaks, 500 Mz 1H NMR (CDCl3) δ 7.63–7.69 (bs), 4.76 (bs), 3.42 (s), 2.74–2.68 (m), 2.66–2.61 (m), 2.33–2.26 (m), 1.80–1.74 (m); cis:trans isomers, diagnostic peaks 125 MHz 13C NMR (CDCl3) δ 152.1, 132.3, 126.0, 119.2, 110.7, 73.5, 61.5, 55.9, 54.6, 50.8, 42.5, 27.0, 23.8, 23.5; LRMS m/z Calcd for C16H2ON2O 256.347 obsd LRMS (M+1) 257.2.

EXAMPLE 214

1-(4-Morpholin-4-ylmethyl-phenyl)-3-piperidin-1-ylmethyl-cyclobutanol

Preparation as described for Example 210 using the appropriate starting materials, 3-piperidin-1-ylmethyl-cyclobutanone (Intermediate 7) and 4-(4-bromobenzyl)morpholine (Bioorg. Med. Chem. Lett. EN; 12; 20; 2002; 2987–2992).

Rf=0.22 (10% MeOH/CH2Cl2 w/NH4OH; mixture, trans:cis isomers, diagnositic peaks 400 MHz 1H NMR (CDCl3) δ 7.26–7.19 (m), 4.38 (s) and 3.37(s); mixture, cis:trans isomers, diagnostic peaks 100 MHz 13C NMR (CDCl3) δ 146.7, 145.7, 129.3, 125.4, 124.9, 67.0, 65.8, 55.5, 54.6; LRMS m/z Calcd for C21H32N2O2 344.496; obsd LRMS (M+1) 345.5.

EXAMPLE 215

3-Morpholin-4-ylmethyl-1-(4-morpholin-4-ylmethyl-phenyl)-cyclobutanol

Preparation as described for Example 210 using the appropriate starting materials, 3-morpholin-4-ylmethyl-cyclobutanone and 4-(4-bromobenzyl)morpholine (Bioorg. Med. Chem. Lett. EN; 12; 20; 2002; 2987–2992).

Rf=0.24 (10% MeOH/CH2Cl2 w/0.1% NH4OH); cis:trans isomers, diagnostic peaks, 500 Mz 1H NMR (CDCl3) δ 7.46–7.43 (m), 7.31–7.25(m), 3.73–3.67 (m), 3.44 (s), 2.48–2.37 (m); cistrans isomers, diagnostic peaks, $^{13}C$ NMR 125 MHz (CDCl3) δ 145.1, 129.6, 125.3, 73.6, 67.1, 53.7; LRMS m/z Calcd for C20H30N2O3 346.468; obsd LRMS (M+1) 347.4.

EXAMPLE 216

1-(4-Dimethylaminomethyl-phenyl)-3-pyrrolidin-1-ylmethyl-cyclobutanol

Preparation as described for Example 210 using the appropriate starting materials, 3-pyrrolidin-1-ylmethyl-cyclobutanone (Intermediate 6, General procedure B ,Step C) and (4-Bromo-benzyl)-dimethyl-amine (J. Amer. Chem. Soc.; EN; 105; 13; 1983; 4136–4142).
Rf=0.1 (30% MeOH/CH2Cl2 w/0.1% NH4OH); cis:trans isomers, diagnostic peaks 400 MHz 1H NMR (CD3OD) δ 7.53 major isomer (d, J=8.3 Hz), 7.31 major isomer (d, J=8.3 Hz), 2.23 (s), 2.21 (s); LRMS m/z Calcd for C18H28N2O 288.432; obsd LRMS (M+1) 289.4.

EXAMPLE 217

3-(4-Pyrimidin-2-yl-piperazin-1-ylmethyl)-1-(4-pyrrolidin-1-ylmethyl-phenyl)-cyclobutanol Preparation as described for Example 210 using the appropriate starting materials.
Rf=0.3 (20% MeOH/CH2Cl2 w/0.1% NH4OH); cis:trans isomers, diagnostic peaks, 400 Mz 1H NMR (CDCl3) δ 8.13 (d, J=4.6 Hz), 7.35 (d, J=7.9 Hz), 7.22–7.14 (m), 6.34 (dd, J=4.1, 4.1 Hz), 4.16 (bs), 3.67–3.65 (m), 3.47 major isomer (s), 3.45 minor isomer (s), 2.63–2.59 (m), 2.37–2.32 (m) 1.63–1.62 (m); cis:trans isomers, diagnostic peaks 100 MHz 13C NMR (CDCl3) δ 157.9, 145.3, 136.9, 129.3, 124.9, 110.1, 65.0, 54.0, 43.5, 23.3; LRMS m/z Calcd for C24H33N5O 407.559; obsd LRMS (M+1) 408.3.

EXAMPLE 218

General Procedure

Step E

1-[4-(3-Pyrrolidin-1-ylmethyl-cyclobutyl)-benzyl]-pyrrolidine

To a stirring solution of 3-pyrrolidin-1-ylmethyl-1-(4-pyrrolidin-1-ylmethyl-phenyl)-cyclobutanol (Example 210, General procedure B, Step D) (0.10 g, 0.32 mmol) in 1,2-dichloroethane (3.2 mL) was added methanesulfonic acid (0.31 g, 3.2 mmol). The reaction was then heated to 65 □C (oil bath) for 30 minutes. The reaction was then cooled to room temperature and transferred to a Parr bottle. To this crude solution was added 5 mL of MeOH, 10% Pd/C (100 mg), and then the reaction vessel was pressurized to 45 psi with H₂. After 30 min the reaction was purged with N₂, filtered through a pad of celite, and concentrated under reduced pressure. Purification of this material was accomplished flash column chromatography using a 15 g ISCO column, pre-packing material on silica, eluting with a gradient of 20%–45% MeOH/CH2Cl2 with 0.1% NH4OH. The product containing fractions were collected and concentrated to give the title compound as the (0.97 mg) as the bis-methanesulfonic acid salt.
Alternatively, to a stirring solution of 3-pyrrolidin-1-ylmethyl-1-(4-pyrrolidin-1-ylmethyl-phenyl)-cyclobutanol (Example 8, General procedure B, Step D) (1.1 g, 3.5 mmol) in TFA (5.4 mL, 70.1 mmol) was added triethyl silane (5.6 mL, 35.0 mmol). The reaction was then heated to 75 □C (oil bath) for 14 hours. The reaction was then cooled to rt and concentrated under reduced pressure. The residual was taken up in CH₂Cl₂ and washed with NaHCO₃. The aqueous layer was back extracted with 3:1 (CH₃Cl:isopropanol). The combined organic layers were dried over MgSO₄, filtered though a fritted funnel and concentrated under reduced pressure. Purification of this material was accomplished by flash column chromatography using a 40 M Biotage column, eluting with a gradient of 10%–20% MeOH/CH₂Cl₂ with 0.3% NH₄OH. The product containing fractions were collected and concentrated to give the title compound (324 mg, 18%) as the bis-TFA salt. To this material in EtOAc was added a solution of HCl (2 eq, 2M THF). The resulting solution was stirred over night, and then filtered through a fritted funnel. The solid was collected and dried under reduced pressure to yield the title compound as the bis-HCl salt and as a mixture of isomers.
Rf=0.3 (30% MeOH/CH2Cl2 w/0.1% NH4OH); cis:trans isomers, TFA salt, diagnostic peaks, 400 Mz 1H NMR (CDCl3) δ 7.40–7.11 (m), 4.15 (s), 4.14 (s), 3.56–3.36 (m), 3.26 (d, J=7.8 Hz), 3.08 (d, J=7.05 Hz); cis:trans isomers, TFA salt, diagnostic peaks 100 MHz 13C NMR (CDCl3) δ 146.7, 130.6, 128.1, 127.5, 127.3, 60.3, 57.9, 53.8, 52.9, 36.0, 34.7, 32.4; LRMS m/z Calcd for C20H30N2 298.471, obsd LRMS (M+1) 299.4.

EXAMPLE 219

4-[4-(3-Piperidin-1-ylmethyl-cyclobutyl)-benzyl]-morpholine

Preparation as described for Example 218 (General procedure A, Step E) using the appropriate starting material of example 214, 1-(4-morpholin-4-ylmethyl-phenyl)-3-piperidin-1-ylmethyl-cyclobutanol.)
Rf=0.23 (10% MeOH/CH2Cl2 w/0.1% NH4OH); HCl salt, mixture trans:cis isomers, diagnositic peaks 400 MHz 1H NMR (CD3OD) δ 7.60 (d, J=8.3 Hz), 7.43 (d, J=7.9 Hz) one set, 7.52 (d, J=8.3 Hz), 7.37 (d, J=8.4 Hz), 4.36 (s), 4.35 (s); LRMS m/z Calcd for C21H32N2O 328.497; obsd LRMS (M+1) 329.5.

EXAMPLE 220

1-[4-(3-Pyrrolidin-1-ylmethyl-cyclobutyl)-benzyl]-piperidine

Preparation as described for Example 218 (General procedure A, Step E) using the appropriate starting material of example 211, 1-(4-piperidin-1-ylmethyl-phenyl)-3-pyrrolidin-1-ylmethyl-cyclobutanol.
Rf=0.3 (30% MeOH/CH2Cl2 w/0.1% NH4OH); cis:trans isomers, TFA salt, diagnostic peaks, 400 Mz 1H NMR (CDCl3) δ 7.20 major isomer (d, J=7.9 Hz), 7.13 minor isomer (d, 8.3 Hz), 7.06 major isomer (d, J=7.9 Hz), 3.78 (s), 3.76 (s), 2.52–2.49 (m), 1.97–1.94 (m), 1.83–1.75 (m); cis:trans isomers, TFA salt, diagnostic peaks, 100 Mz 13C NMR (CDCl3) δ 145.3, 130.7, 126.8, 61.8, 53.9, 36.1, 23.4; LRMS m/z Calcd for C21H32N2 312.498 obsd LRMS (M+1) 313.4.

EXAMPLE 221

Dimethyl-[4-(3-pyrrolidin-1-ylmethyl-cyclobutyl)-benzyl]-amine

Preparation as described for Example 218 (General procedure A, Step E) using the appropriate starting material of example 216, 1-(4-dimethylaminomethyl-phenyl)-3-pyrrolidin-1-ylmethyl-cyclobutanol.

Rf=0.15 (30% MeOH/CH2Cl2 w/0.1% NH4OH); cis:trans isomers, TFA salt, diagnostic peaks, 400 Mz 1H NMR (CDCl3) δ 7.20 major isomer (d J=9.5 Hz), 3.47 minor isomer (s), 3.46 major isomer (s), 3.30–3.28 (m), 2.83–2.80 (m), 2.56–2.53 (m), 2.24 minor isomer (s), 2.23 major isomer (s); LRMS m/z Calcd for C18H28N2 272.433; obsd LRMS (M+1) 273.4.

EXAMPLE 222

4-(3-Pyrrolidin-1-ylmethyl-cyclobutyl)-benzonitrile

Preparation as described for Example 218 (General procedure A, Step E) using the appropriate starting material of example 213, 4-(1-Hydroxy-3-pyrrolidin-1-ylmethyl-cyclobutyl)-benzonitrile.

Rf=0.22 (10% MeOH/CH2Cl2 w/0.1% NH4OH); cis:trans isomers, diagnostic peaks, 500 Mz 1H NMR (CDCl3) δ 7.53 (d, J=6.6 Hz), 7.51 (d, J=8.3 Hz), 7.29 (d, J=8.3 Hz), 7.22 (d, J=8.3 Hz), 3.58 (dddd, J=7.9, 7.9, 7.9, 7.9 Hz), 3.43–3.36 (m), 2.60–2.48 (m), 2.80–1.76 (m); cis:trans isomers, diagnostic peaks 125 MHz 13C NMR (CDCl3) δ 151.4, 132.5, 132.3, 127.4, 119.4, 109.7, 62.8, 62.0, 54.7, 36.6, 35.2, 33.0, 23.6; LRMS m/z Calcd for C16H2ON2 240.348 obsd LRMS (M+1) 241.3.

EXAMPLE 223

General Procedure B

Step F 4-(3-Pyrrolidin-1-ylmethyl-cyclobutyl)-N-hydroxy-benzamidine

To a stirring solution of Example 222 (4-(3-Pyrrolidin-1-ylmethyl-cyclobutyl)-benzonitrile) (150 mg, 0.62 mmol) in MeOH (1.5 mL) was added NaHCO$_3$ (58 mg, 0.62 mmol), followed by hydroxylamine hydrochloride (43.4 mg, 0.62 mmol). The reaction was then heated to 70° C. over night. Both TLC and MS analysis indicated complete consumption of starting material. The reaction was cooled to room temperature and concentrated under reduced pressure. Water was added and a gummy solid formed. The water was removed and the residual was taken up in MeOH and concentrated under reduced pressure to yield the title compound (50 mg, 29% yield). This material was used without further purification.

Rf=0.22 (15% MeOH/CH2Cl2 w/0.1% NH4OH); cis:trans isomers, diagnostic peaks, 400 Mz 1H NMR (CD3OD) δ 7.60–7.52 (m), 7.30–7.15 (m), 3.58–3.41 (m), 2.64 (bs), 1.83 (bs); cis:trans isomers, diagnostic peaks 100 MHz 13C NMR (CD3OD) δ 154.2, 126.3, 62.2, 22.9; LRMS m/z Calcd for C16H23N3O 273.378; obsd LRMS (M+1) 274.3.

EXAMPLE 224

General Procedure B

Step G

5-Methyl-3-[4-(3-pyrrolidin-1-ylmethyl-cyclobutyl)-phenyl]-[1,2,4]oxadiazole

To a stirring solution of Example 223 (4-(3-Pyrrolidin-1-ylmethyl-cyclobutyl)-N-hydroxy-benzamidine) (89 mg, 0.33 mmol) in 1,2-dichlorethane (1 mL) was added acetic anhydride (200 uL, 2.1 mmol). The reaction was heated to reflux (oil bath 100 □C). After 2.5 hours the reaction was cooled to room temperature, concentrated under reduced pressure and purified. Purification of this material was accomplished by flash column chromatography using a 10 g ISCO column, eluting with a gradient of 2%–5% MeOH/CH$_2$Cl$_2$ with 0.2% NH$_4$OH. The product containing fractions were collected and concentrated to give the title compound (45 mg, 46% yield) as a mixture of isomers. The HCl salt was made by taking the free base up in EtOAc and adding a solution of HCl (1 eq, 2M in Et$_2$O), using ether to precipitate a gummy solid, dried under reduced pressure to yield a tan solid.

Rf=0.3 (10% MeOH/CH2Cl2 w/0.1% NH4OH); cis:trans isomers, diagnostic peaks, 500 Mz 1H NMR (CDCl3) δ 3.61–3.57 (m), 3.45–3.39 (m); cis:trans isomers, diagnostic peaks, 125 Mz 13C NMR (CDCl3) δ 176.6, 168.5, 127.6, 127.5, 54.6, 36.6, 35.4, 33.2, 31.0, 23.6; LRMS m/z Calcd for C18H23N3O 297.4; obsd LRMS (M+1) 298.2.

EXAMPLE 225

4-(3-Pyrrolidin-1-ylmethyl-cyclobutyl)-benzylamine

To a stirring soluiont of Example 213 (4-(1-Hydroxy-3-pyrrolidin-1-ylmethyl-cyclobutyl)-benzonitrile) (500 mg, 1.9 mmol) in 20 mL of each MeOH and EtOH was added methanesulfonic acid (1.3 mL, 19.5 mmol), followed by 125 mg of 10% palladium/carbon. The reaction vessel was purged several times with N$_2$ and then pressurized with 45 psi H$_2$. After 1 h the reaction mixture was purged with N$_2$ filtered through a plug of Celite and concentrated under reduced pressure. This mixture was re-dissolved in EtOH (20 mL) then 10% Pd/C (125 mg) was added. As before the reaction vessel was purged several times with N$_2$, pressurized with 45 psi H$_2$ and then heated to 50° C. After 2 hours the reaction mixture was purged with N$_2$, filtered through a plug of Celite, and concentrated under reduced pressure to yield viscous oil. This oil was taken up in MeOH and solid NaOH (780 mg, 19.5 mmol.) was added. This mixture was stirred overnight. The solid were then filtered off and the filtrate was concentrated. The HCl salt was made by the first dissolving the residual compound in EtOAc and then a solution of HCl (2N in Et$_e$O) was added. The solids was collected and dried under reduced pressure. Purification of this material was accomplished by dry pack method flash column chromatography using a 40 g ISCO column, eluting with a gradient of 10%–40% MeOH/CH$_2$Cl$_2$ with 0.2% NH$_4$OH. The product containing fractions were collected and concentrated to give the title compound (350 mg, 74% yield) as a colorless solid. The HCl salt of the title compound was made treating the title compound in EtOAc with a solution of HCl (2N in Et$_2$O).

Rf=0.12 (40% MeOH/CH2Cl2 w/0.1% NH4OH); cis:trans isomers, diagnostic peaks, 400 Mz 1H NMR (CD3OD)

δ 7.43 (d, J=8.3 Hz), 7.37 minor isomer (d, J=7.9 Hz), 7.32 major isomer (d, 8.3 Hz), 4.11 (s), major isomer 4.10 (s), 2.08 (bs), 2.01–1.93 (m); cis:trans isomers, diagnostic peaks 100 MHz 13C NMR (CD3OD) δ 145.9, 131.2, 129.2, 127.0, 59.6, 48.6, 43.0, 38.5, 22.8; LRMS m/z Calcd for C16H24N2 244.38; obsd LRMS (M+1) 245.3.

EXAMPLE 226

1-(3-p-Tolyl-cyclobutylmethyl)-pyrrolidine

To a stirring solution of Example 212, (1-(4-benzyloxymethyl-phenyl)-3-pyrrolidin-1-ylmethyl-cyclobutanol) (200 mg, 0.57 mmol) in EtOH (10 mL) was added methane sulfonic acid (370 uL, 5.7 mmol), followed by 10% Pd/C (200 mg). The reaction vessel was purged with $N_2$, and then pressurized with 45 psi $H_2$. After 30 minute the reaction vessel was purged with nitrogen. The reaction was filtered through a plug of Celite and then concentrated under reduced pressure. The residual was dissolved in EtOAc and a solution of HCl (2 N in ether) was added. The solution was decanted and the residual was purified. Purification of this material was accomplished by dry pack flash column chromatograpy using a 40 g ISCO column, eluting with a gradient of 5%–15% MeOH/CH$_2$Cl$_2$ with 0.2% NH$_4$OH. The product containing fractions were collected and concentrated to give the title compound (100 mg, 77% yield) as a colorless oil. The HCl salt of the title compound was made by dissolving the title compound in ethyl acetate and then adding a solution of HCl (2N in ether), the resulting colorless solid was collected and dried under reduced pressure.

Rf=0.5 (25% MeOH/CH2Cl2 w/0.1% NH4OH); cis:trans isomers, diagnostic peaks, 400 Mz 1H NMR (CD3OD) δ7.11–7.07 (m), 3.41–3.23 (m), 3.28 (d, J=7.0 Hz), 2.69 (s), 2.67–2.53 (m), 2.07–2.23 (m); cis:trans isomers, diagnostic peaks 100 MHz 13C NMR (CD3OD) δ 141.8, 135.5, 128.8, 126.2, 60.0, 54.0, 38.5, 38.4, 36.2, 34.5, 28.3, 22.7; LRMS m/z Calcd for C16H23N 229.365; obsd LRMS (M+1) 230.2.

EXAMPLE 227 trans-4-[3-(4-Pyrrolidin-1-ylmethyl-phenyl)-cyclobutylmethyl]-thiomorpholine

Preparation as described for Example 138, using the appropriate amine and the tosylate of Example 48 (trans-toluene-4-sulfonic acid 3-(4-pyrrolidin-1-ylmethyl-phenyl)-cyclobutylmethyl ester). Rf=0.33 (10% MeOH/CH2Cl2 w/0.1% NH4OH); 400 MHz 1H NMR (CDCl3) δ 7.24 (d, J=7.94 Hz, 2H), 7.20 (d, J=7.9 Hz, 2H), 3.57 (s, 2H), 3.5 (dddd, J=8.1, 7.9, 7.9, 8.1 Hz, 1H), 3.09–3.06 (m, 2H), 2.69–2.61 (m, 4H), 2.58–2.43 (m, 5H), 2.27–2.19 (m, 2H), 2.15–2.08 (m, 2H), 1.79–1.70 (m, 4H); 100 MHz 13C NMR (CDCl3) δ 145.2, 136.7, 129.1, 126.5, 65.2, 60.6, 55.3, 54.3, 48.1, 36.4, 33.6, 28.1, 23.6; LRMS m/z Calcd for C20H30N2S 330.5; obsd LRMS APCI (M+1) m/z 331.

EXAMPLE 228 trans-6-{4-[3-(4-Pyrrolidin-1-ylmethyl-phenyl)-cyclobutylmethyl]-piperazin-1-yl}-nicotinonitrile Preparation as described for Example 138, using the appropriate amine and the tosylate of Example 48 (trans-toluene-4-sulfonic acid 3-(4-pyrrolidin-1-ylmethyl-phenyl)-cyclobutylmethyl ester). Rf=0.25 (20% MeOH/CH2Cl2 w/0.4% NH4OH); 500 MHz 1H NMR (CDCl3) δ 8.36 (s, 1H), 7.54 (dd, J=2.5, 2.5 Hz, 1H), 7.22 (d, J=8.3 Hz, 2H), 7.10 (d, J=8.3 Hz, 2H), 6.54 (dd, J=0.8 Hz, 1H), 3.66–3.62 (m, 4H), 3.54 (s, 2H), 3.41–3.32 (m, 1H), 2.55–2.41 (m, 13H), 1.84–1.70 (m, 6H); 125 MHz 13C NMR (CDCl3) δ 159.5, 152.9, 144.4, 138.9, 137.1, 129.0, 126.3, 118.9, 105.9, 96.3, 65.3, 60.6, 54.3, 53.1, 44.6, 36.7, 35.9, 29.9, 23.6; LRMS m/z Calcd for C26H33N5 415.6; obsd LRMS APCI (M+1) m/z 416.

EXAMPLE 229 trans-1-Methanesulfonyl-4-[3-(4-pyrrolidin-1-ylmethyl-phenyl)-cyclobutylmethyl]-piperazine To a stirring solution of the compound of Example 111, (3-(4-Pyrrolidin-1-ylmethyl-phenyl)-cyclobutylmethyl]-piperazine) (121 mg, 0.38 mmol) in 1,2-dichloroethane (3 mL) was added diisopropyl ethyl amine (129 uL, 0.77 mmol) followed by dimethyl 4-amino pyridine (DMAP) (2 mg, 0.02 mmol) followed by methyl sulfonyl chloride (45 uL, 0.77 mmol). The reaction was then heated to 65 C. After 1 hr the reaction was cooled to rt, diluted with EtOAc, and quenched with 1 N NaOH. The aqueous layer was extracted with EtOAc, the combined organic layer were dried over MgSO4, filtered and concentrated under reduced pressure. Purification of this material was accomplished by generating the di-HCl salt. The bis-HCl salt was formed by taking the crude di-amine in EtOAc and adding 2 equivalents of HCl (2 M THF). The solid was filtered and washing with EtOAc. The solid was free based with 1N NaOH, and then extracted with EtOAc, dried, filtered and concentrated to give the title compound as a tan solid. Rf=0.55 (30% MeOH/CH2Cl2 w/0.1% NH4OH); 500 MHz 1H NMR (CDCl3) δ 7.26 (d, J=7.9 Hz, 2H), 7.17 (d, J=8.3 Hz, 2H), 3.59 (s, 2H), 3.54 (dddd, J=8.3, 7.9, 7.9, 8.3 Hz, 1H), 3.24–3.20 (m, 4H), 2.76 (s, 3H), 2.62–2.48 (m, 11H), 2.32–2.23(m, 2H), 2.19–2.11 (m, 2H), 1.81–1.74 (m, 4H); 125 MHz 13C NMR (CDCl3) δ 145.0, 136.7, 128.2, 126.5, 64.0, 60.6, 54.3, 52.8, 46.1, 36.4, 34.3, 33.3, 28.9, 23.6; LRMS m/z Calcd for C21H33N3O2S 391.6; obsd LRMS APCI (M+1) m/z 392.

EXAMPLE 230 trans-1-Ethanesulfonyl-4-[3-(4-pyrrolidin-1-ylmethyl-phenyl)-cyclobutylmethyl]-piperazine Preparation as described for Example 229, using the appropriate ethyl sulfonyl chloride to yield the compound. Rf=0.29 (10% MeOH/CH2Cl2 w/0.2% NH4OH); 500 MHz 1H NMR (CDCl3) δ 7.25 (d, J=8.3 Hz, 2H), 7.16 (d, J=8.3 Hz, 2H), 3.57 (s, 2H), 3.53 (dddd, J=8.3, 7.9, 7.9, 8.3 Hz, 1H), 3.30–3.26 (m, 4H), 2.92 (dd, J=7.5, 7.1 Hz, 2H), 2.60–2.46 (m, 12H), 2.30–2.21 (m, 2H), 2.18–2.10 (m, 2H), 1.80–1.72 (m, 4H), 1.35 (dd, J=7.5, 7.5 Hz, 3H); 100 MHz 13C NMR (CDCl3) δ 145.0, 136.8, 128.1, 126.5, 64.1, 60.6, 54.4, 53.2, 46.0, 43.7, 36.4, 33.4, 28.9, 23.6, 8.0; LRMS m/z Calcd for C22H35N3O2S 405.6; obsd LRMS APCI (M+1) m/z 406.

EXAMPLE 231 trans-1-(Propane-2-sulfonyl)-4-[3-(4-pyrrolidin-1-ylmethyl-phenyl)-cyclobutylmethyl]-piperazine Preparation as described for Example 229, using the appropriate isopropyl sulfonyl chloride yields the title compound. Rf=0.32 (10% MeOH/CH2Cl2 w/0.1% NH4OH);

400 MHz $^1$H NMR (CDCl3) δ 7.27 (d, J=7.9 Hz, 2H), 7.18 (d, J=8.3 Hz, 2H), 3.60 (s, 2H), 3.55 (dddd, J=8.3, 7.9, 7.9, 8.3 Hz, 1H), 3.39–3.34 (m, 4H), 3.18 (septet, J=7.1 Hz), 2.62–2.46 (m, 11H), 2.32–2.23 (m, 2H), 2.19–2.12 (m, 2H), 1.82–1.76 (m, 4H), 1.33 (d, J=6.6 Hz, 6H); 100 MHz 13C NMR (CDCl3) δ 145.2, 136.6, 129.2, 126.5, 64.2, 60.5, 54.5, 53.6, 53.4, 46.5, 36.4, 33.4, 28.9, 23.6, 17.0; LRMS m/z Calcd for C23H37N3O2S 419.6; obsd LRMS APCI (M+1) m/z 420.

EXAMPLE 232 trans-2-Methyl-1-{4-[3-(4-pyrrolidin-1-ylmethyl-phenyl)-cyclobutylmethyl]-piperazin-1-yl}-propan-1-one To a stirring solution of Example 111, (3-(4-Pyrrolidin-1-ylmethyl-phenyl)-cyclobutylmethyl]-piperazine) (100 mg, 0.32 mmol) in 1,2-dichloroethane (4 mL) was added diisopropyl ethylamine (111 uL, 0.64 mmol) followed by the addition of isobutyryl chloride (50 uL, 0.48 mmol). After 15 min the reaction was quenched with 1N NaOH, extracted with dichloromethane. The combined organic layers were dried over MgSO4, filtered through a fritted funnel and concentrated under reduced pressure. Purification of this material was accomplished by flash column chromatography, using a 12 g ISCO column, eluting with 4% MeOH/$CH_2Cl_2$ with 0.2% NH4OH. The product containing fractions were collected and concentrated to give the title compound (118 mg, 97% yield) as colorless oil. Rf=0.27 (10% MeOH/CH2Cl2 w/0.2% NH4OH); 500 MHz 1H NMR (CDCl3) δ 7.23 (d, J=8.3 Hz, 2H), 7.15 (d, J=8.3 Hz, 2H), 3.61–3.44 (m, 7H), 2.74 (septet, J=7.1 Hz, 1H), 2.56–2.45 (m, 7H), 2.42–2.34 (m, 4H), 2.28–2.20 (m, 2H), 2.17–2.09 (m, 2H), 1.79–1.70 (m, 4H), 1.08 (d, J=7.1 Hz, 6H); 125 MHz 13C NMR (CDCl3) δ 175.5, 145.1, 136.7, 129.1, 126.5, 64.3, 60.5, 54.3, 45.6, 41.8, 36.5, 33.4, 30.1, 29.0, 23.6, 19.6; LRMS m/z Calcd for C24H37N3O 383.6; obsd LRMS APCI (M+1) m/z 384.

EXAMPLE 233 trans-(1S,4S)-2-Methanesulfonyl-5-[3-(4-pyrrolidin-1-ylmethyl-phenyl)-cyclobutylmethyl]-2,5-diaza-bicyclo[2.2.1]heptane Preparation as described for Example 138, using the appropriated amine and the tosylate of Example 48 (trans-toluene-4-sulfonic acid 3-(4-pyrrolidin-1-ylmethyl-phenyl)-cyclobutylmethyl ester). Rf=0.24 (10% MeOH/CH2Cl2 w/0.2% NH4OH); 500 MHz 1H NMR (CDCl3) δ 7.21 (d, J=7.9 Hz, 2H), 7.13 (d, J=8.3 Hz, 2H), 4.21 (bs, 1H), 3.56–3.45 (m, 5H), 3.15 (dd, J=2.5 Hz, 1H), 2.90 (dd, J=2.5 Hz, 1H), 2.82 (s, 3H), 2.80–2.65 (m, 3H), 2.49–2.42 (m, 4H), 2.39–2.28 (m, 1H), 2.25–2.06 (m, 4H), 1.86 (d, J=9.0 Hz, 1H), 1.77–1.68 (m, 4H), 1.65 (d, J=9.9 Hz, 1H); 125 MHz 13C NMR (CDCl3) δ 145.0, 136.9, 129.1, 126.4, 62.0, 60.6, 59.5, 54.3, 50.9, 38.5, 36.6, 36.4, 32.9, 32.7, 30.8, 23.6; LRMS m/z Calcd for C22H33N3O2S 403.6; obsd LRMS APCI (M+1) m/z 404.

EXAMPLE 234 cis-1-{4-[3-(4-Pyrrolidin-1-ylmethyl-phenyl)-cyclobutylmethyl]-piperazin-1-yl}-ethanone Preparation as described for Example 100, General Procedure A, Step H, using the appropriated amine and the tosylate of Example 47 (cis-toluene-4-sulfonic acid 3-(4-pyrrolidin-1-ylmethyl-phenyl)-cyclobutylmethyl ester). Rf=0.24 (20% MeOH/CH2Cl2 w/0.5% NH4OH); LRMS m/z Calcd for C22H33N3O 355.5; obsd LRMS APCI (M+1) m/z 356.

EXAMPLE 235 cis-4-[3-(4-Pyrrolidin-1-ylmethyl-phenyl)-cyclobutylmethyl]-thiomorpholine

Preparation as described for Example 100, General Procedure A, Step H, using the appropriated amine and the tosylate of Example 47 (cis-toluene-4-sulfonic acid 3-(4-pyrrolidin-1-ylmethyl-phenyl)-cyclobutylmethyl ester); Rf=0.25 (20% MeOH/CH2Cl2 w/0.5% NH4OH); 400 MHz 1H NMR (CD3OD) δ 7.47 (d, J=7.9 Hz, 2H), 7.36 (d, J=7.9 Hz), 4.34 (s, 2H), 3.75 (d, J=12.0 Hz, 2H), 3.58–3.42 (m, 3H), 3.31–3.10 (m, 8H), 2.92–2.74 (m, 3H), 2.68–2.60 (m, 2H), 2.22–2.11 (m, 2H), 2.05–1.94 (m, 4H); 100 MHz 13C NMR (CD3OD) δ 146.6, 130.4, 128.8, 127.2, 62.3, 57.8, 54.0, 53.6, 36.4, 34.7, 26.4, 24.5, 22.6; LRMS m/z Calcd for C20H30N2S 330.5; obsd LRMS APCI (M+1) m/z 331.

The composition of the present invention may be a composition comprising a compound of formula I and optionally a pharmaceutically acceptable carrier. The composition of the present invention may also be a composition comprising a compound of formula I, a histamine $H_1$ antagonist and optionally a pharmaceutically acceptable carrier. The composition of the present invention may also be a composition comprising a compound of formula I, a neurotransmitter re-uptake blocker and optionally a pharmaceutically acceptable carrier.

The composition of the present invention may be formulated in a conventional manner using one or more pharmaceutically acceptable carriers. The composition may be formulated for oral, buccal, intranasal, parenteral (e.g., intravenous, intramuscular, intraperitoneal, or subcutaneous or through an implant) nasal, vaginal, sublingual, rectal or topical administration or in a form suitable for administration by inhalation or insufflation.

For oral administration, the pharmaceutical composition may take the form of, for example, tablets or capsules prepared by conventional means with pharmaceutically acceptable excipients such as binding agents such as pregelatinized maize starch, polyvinylpyrrolidone or hydroxypropyl methylcellulose; fillers such as lactose, microcrystalline cellulose or calcium phosphate; lubricants such as magnesium stearate, talc or silica; disintegrants such as potato starch or sodium starch glycolate; or wetting agents such as sodium lauryl sulphate. The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents such as sorbitol syrup, methyl cellulose or hydrogenated edible fats; emulsifying agents such as lecithin or acacia, non-aqueous vehicles such as almond oil, oily esters or ethyl alcohol; and preservatives such as methyl or propyl p-hydroxybenzoates or sorbic acid.

For buccal administration, the composition may take the form of tablets or lozenges formulated in conventional manner.

The composition of the invention may be formulated for parenteral administration by injection, including using conventional catheterization techniques or infusion. Formulations for injection may be presented in unit dosage form, for example, in ampoules or in multi-dose containers, with an added preservative. The composition may take such forms as suspensions, solutions or emulsions in oily or aqueous vehicles, and may contain formulating agents such as suspending, stabilizing and/or dispersing agents. Alternatively, the active ingredient or ingredients in a composition may be in powder form for reconstitution with a suitable vehicle, for example, sterile pyrogen-free water, before use. The term "active ingredient" as used herein refers to a compound of the formula I, a histamine $H_1$ antagonist, or a neurotransmitter re-uptake blocker.

The composition of the invention may also be formulated in a rectal composition such as suppositories or retention enemas, for example, containing conventional suppository bases such as cocoa butter or other glycerides. A composition for vaginal administration is preferably a suppository that may contain, in addition to the active ingredient or ingredients, excipients such as cocoa butter or a suppository wax. A composition for nasal or sublingual administration is also prepared with standard excipients well known in the art.

For intranasal administration or administration by inhalation, the composition may be conveniently delivered in the form of a solution or suspension from a pump spray container that is squeezed or pumped by the patient or as an aerosol spray presentation from a pressurized container or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active ingredient or ingredients. Capsules and cartridges, made, for example, from gelatin, for use in an inhaler or insufflator may be formulated containing a powder mix of an active ingredient or ingredients and a suitable powder base such as lactose or starch. The active ingredient or ingredients in the composition may range in size from nanoparticles to microparticles.

An exemplary dose of the composition of the invention comprising a compound of formula I for oral, parenteral or buccal administration to the average adult human for the treatment of the conditions referred to herein is about 0.01 to about 1000 mg of the compound of formula I per unit dose which could be administered, for example, 1 to 3 times per day.

An exemplary dose of the composition of the invention comprising a compound of formula I and a histamine $H_1$ antagonist or a neurotransmitter re-uptake blocker for oral, parenteral or buccal administration to the average adult human for the treatment of the conditions referred to herein is about 0.01 to about 500 mg of the compound of formula I and of about 0.01 mg to about 500 mg of the histamine $H_1$ antagonist or the neurotransmitter re-uptake blocker per unit dose which could be administered, for example, 1 to 3 times per day.

Aerosol formulations for treatment of the conditions referred to herein in the average adult human are preferably arranged so that each metered dose or "puff" of aerosol contains about 20 µg to about 1000 µg of the compound of formula I. The overall daily dose with an aerosol will be within the range about 100 µg to about 10 mg. Administration may be several times daily, for example 2, 3, 4 or 8 times, giving for example, 1, 2 or 3 doses each time. Aerosol formulations containing a compound of formula I and a histamine $H_1$ antagonist or a neurotransmitter re-uptake blocker are preferably arranged so that each metered dose or "puff" of aerosol contains about 100 µg to about 10,000 µg of the compound of formula I and about 100 µg to about 30,000 µg of the histamine $H_1$ antagonist or the neurotransmitter re-uptake blocker. Administration may be several times daily, for example 1, 3, 4 or 8 times, giving for example, 1, 2 or 3 doses each time. The composition of the invention comprising a compound of formula I and a histamine $H_1$ antagonist or a neurotransmitter re-uptake blocker may optionally contain a pharmaceutically acceptable carrier and may be administered in both single and multiple dosages as a variety of different dosage forms, such as tablets, capsules, lozenges, troches, hard candies, powders, sprays, aqueous suspension, injectable solutions, elixirs, syrups, and the like. The pharmaceutically acceptable carriers include solid diluents or fillers, sterile aqueous media and various non-toxic organic solvents, etc. Oral pharmaceutical formulations can be suitably sweetened and/or flavored by means of various agents of the type commonly employed for such purposes. In general, the compound of formula I is present in such dosage forms at concentration levels ranging from about 0.1% to about 99.9% by weight of the total composition, i.e., in amounts which are sufficient to provide the desired unit dosage, and the histamine $H_1$ antagonist or the neurotransmitter re-uptake blocker is present in such dosage forms at concentration levels ranging from about 0.1% to about 99.9% by weight of the total composition, i.e., in amounts which are sufficient to provide the desired unit dosage.

The compound of formula I and the histamine $H_1$ antagonist may be administered together or separately. When administered separately, the compound of formula I and the histamine $H_1$ antagonist may be administered in either order, provided that after administration of the first of the two active ingredients, the second active ingredient is administered within 24 hours or less, preferably 12 hours or less.

The compound of formula I and the neurotransmitter re-uptake blocker may be administered together or separately. When administered separately, the compound of formula I and the neurotransmitter re-uptake blocker may be administered in either order, provided that after administration of the first of the two active ingredients, the second active ingredient is administered within 24 hours or less, preferably 12 hours or less.

A preferred dose ratio of compound of formula I to the histamine $H_1$ antagonist or to the neurotransmitter re-uptake blocker for oral, parenteral or buccal administration to the average adult human for the treatment of the conditions referred to herein is from about 0.001 to about 1000, preferably from about 0.01 to about 100.

The composition may be homogeneous, wherein by homogeneous it is meant that the active ingredient or ingredients are dispersed evenly throughout the composition so that the composition may be readily subdivided into equally effective unit dosage forms such as tablets, pills and capsules. This solid composition is then subdivided into unit dosage forms of the type described herein containing from about 0.1 to about 1000 mg of the active ingredient or ingredients. Typical unit dosage forms contain from about 1 to about 300 mg, for example about 1, 2, 5, 10, 25, 50 or 100 mg, of the active ingredient or ingredients. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former.

The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The dosage of the active ingredient or ingredients in the composition and methods of this invention may be varied; however, it is necessary that the amount of the active ingredient or ingredients in such a composition be such that a suitable dosage form is obtained. The selected dosage depends upon the desired therapeutic effect, on the route of administration, the particular compounds administered, the duration of the treatment, and other factors. All dosage ranges and dosage levels mentioned herein refer to each active ingredient present in the pharmaceutical composition of the present invention, as well as those used in the methods of the present invention. Generally, dosage levels of between about 0.01 and about 100 mg/kg of body weight daily are administered to humans and other mammals. A preferred dosage range in humans is about 0.1 to about 50 mg/kg of body weight daily which can be administered as a single dose or divided into multiple doses. A preferred dosage range in mammals other than humans is about 0.01 to about 10.0 mg/kg of body weight daily which can be administered as a single dose or divided into multiple doses. A more preferred dosage range in mammals other than humans is about 0.1 to about 5.0 mg/kg of body weight daily which can be administered as a single dose or divided into multiple doses.

The pharmaceutical composition comprising the compound of formula I and the histamine $H_1$ antagonist or the neurotransmitter re-uptake blocker may be administered at dosages of a therapeutically effective amount of the compound of formula I and of the second active ingredient in single or divided doses.

The specific therapeutically effective dose level for any particular patient will depend upon a variety of factors including the disorder being treated and the severity of the disorder; activity of the specific compound employed; the specific composition employed; the age. However, some variation in dosage will necessarily occur depending upon the condition of the subject being treated. The person responsible for administration will, in any event, determine the appropriate dose for the individual subject.

The dosage amounts set forth in this description and in the appended claims may be used, for example, for an average human subject having a weight of about 65 kg to about 70 kg. The skilled practitioner will readily be able to determine any variation in the dosage amount that may be required for a subject whose weight falls outside the about 65 kg to about 70 kg range, based upon the medical history of the subject. The pharmaceutical combinations may be administered on a regimen of up to 6 times per day, preferably 1 to 3 times per day, such as 2 times per day or once daily.

Determination of Biological Activity

The in vitro affinity of the compounds in the present invention at the rat or human histamine H3 receptors can be determined according to the following procedure. Frozen rat frontal brain or frozen human post-mortem frontal brain is homogenized in 20 volumes of cold 50 mM Tris HCl containing 2 mM $MgCl_2$ (pH to 7.4 at 4 degrees C.). The homogenate is then centrifuged at 45,000 G for 10 minutes. The supernatant is decanted and the membrane pellet resuspended by Polytron in cold 50 mM Tris HCl containing 2 mM MgCl2 (pH to 7.4 at 4 degrees C.) and centrifuged again. The final pellet is resuspended in 50 mM Tris HCl containing 2 mM MgCl2 (pH to 7.4 at 25 degrees C.) at a concentration of 12 mg/mL. Dilutions of compounds are made in 10% DMSO/50 mM Tris buffer (pH 7.4) (at 10× final concentration, so that the final DMSO concentration is 1%). Incubations are initiated by the addition of membranes (200 microliters) to 96 well V-bottom polypropylene plates containing 25 microliters of drug dilutions and 25 microliters of radioligand (1 nM final concentration 3H—N-methyl-histamine). After a 1 hour incubation, assay samples are rapidly filtered through Whatman GF/B filters and rinsed with ice-cold 50 nM Tris buffer (pH 7.4) using a Skatron cell harvester. Radioactivity is quantified using a BetaPlate scintillation counter. The percent inhibition of specific binding can then be calculated.

A person of ordinary skill in the art could adapt the above procedure to other assays.

TABLE 1

Rat Histamine H3 Receptor Binding

| Example # | rH3 $K_i$ (nM) |
| --- | --- |
| 1 | 8.34 |
| 2 | 98.79 |
| 5 | 89.23 |
| 6 | 122.11 |
| 7 | 99.25 |
| 4 | 5.65 |
| 36 | 59.6 |
| 47 | 23.16 |
| 48 | 97.99 |
| 46 | 103.55 |
| 40 | 74.34 |
| 41 | 31.98 |
| 42 | 130.98 |
| 44 | 44.35 |
| 14 | 79.44 |
| 27 | 74.23 |
| 55 | 92.64 |
| 56 | 23.47 |
| 57 | 100.5 |
| 59 | 26.24 |
| 65 | 7.28 |
| 66 | 4.75 |
| 74 | 12.48 |
| 76 | 1.89 |
| 77 | 42.47 |
| 78 | 109.73 |
| 81 | 57.96 |
| 83 | 68.85 |
| 88 | 3.79 |
| 90 | 33.64 |
| 92 | 118.01 |
| 100 | 3.22 |
| 101 | 4.81 |
| 102 | 1.83 |
| 103 | 3.93 |
| 104 | 2.78 |
| 105 | 5.38 |
| 106 | 8.35 |
| 107 | 2.09 |
| 108 | 0.58 |
| 109 | 2.55 |
| 110 | 2.83 |
| 112 | 0.77 |
| 113 | 4.46 |
| 114 | 0.48 |
| 115 | 1.44 |
| 116 | 2.82 |
| 117 | 0.73 |
| 118 | 0.65 |
| 119 | 1.34 |
| 120 | 3.35 |
| 121 | 2.81 |

TABLE 1-continued

Rat Histamine H3 Receptor Binding

| Example # | rH3 $K_i$ (nM) |
|---|---|
| 122 | 2.71 |
| 123 | 6.84 |
| 124 | 0.49 |
| 125 | 1.77 |
| 126 | 1.89 |
| 127 | 101.02 |
| 128 | 8.91 |

The invention claimed is:
1. A compound of formula I

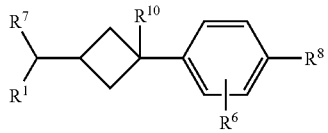

or a pharmaceutically acceptable salt thereof, wherein:
$R^1$ is selected from the group consisting of $N_3$, $OR^4$, and $NR^2R^3$;
$R^2$ and $R^3$ are each independently selected from the group consisting of hydrogen;
$C_1$–$C_8$ alkyl optionally substituted with 1 to 4 halogens;
$C_1$–$C_4$ alkyl group optionally substituted with a substituent selected from the group consisting of OH, one to four $C_1$–$C_4$ alkyl, $C_3$–$C_7$ cycloalkyl, $C_1$–$C_4$ dialkylamino, $C_6$–$C_{14}$ aryl optionally substituted with a halogen and optionally substituted with $C_6$–$C_{10}$ aryloxy optionally substituted with one to two halogens, and 5–10-membered heteroaryl optionally substituted with a $C_6$–$C_{10}$ aryl group and optionally substituted with one to three $C_1$–$C_4$ alkyl groups;
$C_3$–$C_7$ cycloalkyl;
$C_6$–$C_{14}$ aryl;
3–8-membered heterocycloalkyl optionally substituted with one or more $C_1$–$C_4$ alkyl-carbonyl group;
$C_6$–$C_{10}$ arylsulfonyl optionally substituted with one or more $C_1$–$C_2$ alkyl;
5–10-membered heteroaryl; and
$C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl;
wherein $R^3$ can be further selected from the group consisting of
$C_6$–$C_{14}$ arylcarbonyl-$C_6$–$C_{14}$ aryl; $C_6$–$C_{14}$ arylcarbonyl-3–8-membered heterocycloalkyl; $C_3$–$C_8$ cycloalkylcarbonyl-$C_6$–$C_{14}$ aryl; $C_3$–$C_8$ cycloalkylcarbonyl-3–8-membered heterocycloalkyl; 3–8-membered heterocycloalkylcarbonyl-$C_6$–$C_{14}$ aryl; and 3–8-membered heterocycloalkylcarbonyl-3–8-membered heterocycloalkyl;
or $R^3$ and $R^2$ together with the nitrogen of the $NR^2R^3$ group form a first 5-, 6-, or 7-membered aliphatic ring, wherein one of the carbons in the first 5-, 6-, or 7-membered aliphatic ring is optionally replaced by O, S, $NR^{2'}$, or CO, and the first 5-, 6-, or 7-membered aliphatic ring is optionally fused to a $C_6$–$C_{10}$ arylene and is optionally substituted at a ring carbon with a substituent selected from the group consisting of 5–10-membered heteroaryl optionally substituted with one or more halogens and optionally substituted with one or more $C_1$–$C_2$ alkyl,
$C_1$–$C_4$ alkoxy optionally substituted with one or more $C_1$–$C_2$ alkoxy and optionally substituted with one or more $C_1$–$C_4$ dialkylaminocarbonyl, and
one or two $C_1$–$C_4$ alkyl optionally and independently substituted with one or more $C_1$–$C_2$ alkoxy;
wherein $R^{2'}$ is
hydrogen;
$C_1$–$C_8$ alkyl optionally substituted with 1 to 4 halogens;
5–10-membered heteroaryl optionally substituted with a substituent selected from the group consisting of halogen, $C_1$–$C_4$ alkyl, $C_1$–$C_2$ alkoxy, $C_6$–$C_{10}$ aryl, $C_1$–$C_4$ alkylaminocarbonyl, and cyano;
$C_1$–$C_4$ alkyl group optionally substituted with a substituent selected from the group consisting of $C_1$–$C_2$ alkoxycarbonyl, 5–10-membered heteroaryl optionally substituted with one or more $C_1$–$C_2$ alkyl, one to four $C_1$–$C_4$ alkyl, $C_3$–$C_7$ cycloalkyl, and $C_6$–$C_{14}$ aryl;
$C_6$–$C_{10}$ aryl optionally substituted with one or two $C_1$–$C_2$ alkyl;
$C_1$–$C_4$ alkylcarbonyl;
or $C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl;
$R^4$ is
hydrogen;
$C_1$–$C_8$ alkyl optionally substituted with 1 to 4 halogens;
$C_1$–$C_4$ alkyl optionally substituted with a substituent selected from the group consisting of $C_3$–$C_7$ cycloalkyl, 5–10-membered heteroaryl, and
$C_6$–$C_{14}$ aryl optionally substituted with a substituent selected from the group consisting of one, two or three halogens, cyano, one or two $C_1$–$C_2$ alkoxy, $C_1$–$C_2$ di- or tri-fluoroalkyl, $C_1$–$C_4$ alkyl optionally substituted with $C_6$–$C_{10}$ arylsulfonyl, nitro, and 5–10-membered heteroaryl;
5–10-membered heteroaryl optionally fused to a $C_6$–$C_{10}$ arylene group that is optionally substituted with one or more halogens or one or more $C_1$–$C_2$ alkoxy, wherein the 5–10-membered heteroaryl is optionally substituted with a substituent selected from the group consisting of:
$C_6$–$C_{10}$ aryl optionally substituted with one or more halogens, one or more $C_1$–$C_2$ alkoxy, or one or more $C_1$–$C_2$ alkyl;
$C_6$–$C_{10}$ arylcarbonyl optionally substituted with one or more halogens;
one or more halogens;
one to three $C_1$–$C_4$ alkyl groups optionally substituted with one or more $C_6$–$C_{10}$ aryl optionally and independently substituted with one or more halogens or one or more $C_1$–$C_2$ alkoxy;
$C_1$–$C_2$ di- or tri-fluoroalkyl;
1 to 2 $C_1$–$C_2$ alkoxy groups;
3–8-membered heterocycloalkyl;
5–10-membered heteroarylamino;
$C_1$–$C_2$ alkylaminocarbonyl-$C_1$–$C_2$-alkylamino;
$C_6$–$C_{10}$ arylaminocarbonyl;
$C_6$–$C_{10}$ arylaminocarbonyl-$C_1$–$C_2$-alkylamino optionally substituted with one or more halogens at the $C_6$–$C_{10}$ aryl moiety of $C_6$–$C_{10}$ arylaminocarbonyl;
5–10-membered heteroaryl optionally substituted with one or more $C_6$–$C_{10}$ aryl or one or more $C_1$–$C_2$ alkyl;
$C_6$–$C_{10}$ aryloxy optionally substituted with one or more $C_1$–$C_2$ alkoxy or one or more halogens; and $C_1$–$C_4$ dialkylamino;

$C_6$–$C_{14}$ aryl optionally substituted with one or more halogens and optionally substituted with one or more $C_6$–$C_{10}$ aryloxy optionally and independently substituted with one to two halogens;

$C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl; or $C_6$–$C_{10}$ arylsulfonyl optionally substituted with $C_1$–$C_2$ alkyl;

$R^6$ is hydrogen, $C_1$–$C_4$ alkyl or halogen;

$R^7$ is hydrogen, $SO_2C_1$–$C_{10}$ alkyl, $C_1$–$C_8$ alkyl optionally substituted with 1 to 4 halogens, $C_3$–$C_7$ cycloalkyl-$C_0$–$C_4$ alkyl, $C_6$–$C_{14}$ aryl-$C_0$–$C_4$ alkyl, 5–10-membered heteroaryl-$C_0$–$C_4$ alkyl, or $C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl;

$R^{10}$ is OH, halogen or hydrogen;

$R^8$ is CN, —CHR$^7$NR$^{2''}$, R$^{3''}$ or C(=NR$^{12}$)—NR$^{13}$R$^{13'}$, wherein $R^{13}$ and $R^{13'}$ are each independently hydrogen or $C_1$–$C_6$ alkyl and $R^{12}$ is hydrogen, $C_1$–$C_6$ alkyl OH, O—$C_1$–$C_6$ alkyl, NH$_2$, NHC$_1$–$C_6$alkyl, or N(C$_1$–$C_6$alkyl)$_2$, or wherein C(=NR$^{12}$)—NR$^{13}$R$^{13'}$ represents a five-membered heteroaryl group, wherein $R^{12}$ is O, NH, or NC$_1$–$C_6$ alkyl, $R^{13}$ and $R^{13'}$ taken together represent N or CR$^{13''}$ double bonded to the nitrogen of the NR$^{13}$R$^{13'}$ group, and $R^{13''}$ is hydrogen or $C_1$–$C_6$ alkyl;

or when $R^8$ is ortho to $R^6$, $R^6$ and $R^8$ together with the carbons of the aromatic ring to which $R^6$ and $R^8$ are attached may form a 5-membered carbocyclic ring;

$R^{2''}$ is hydrogen, $C_1$–$C_8$ alkyl optionally substituted with 1 to 4 halogens, $C_3$–$C_7$ cycloalkyl-$C_0$–$C_4$ alkyl, $C_6$–$C_{14}$ aryl-$C_0$–$C_4$ alkyl, 5–10-membered heteroaryl-$C_0$–$C_4$ alkyl, or $C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl;

$R^{3''}$ is hydrogen, $C_1$–$C_8$ alkyl optionally substituted with 1 to 4 halogens, $C_6$–$C_{14}$ aryl, $C_6$–$C_{14}$ arylcarbonyl-$C_6$–$C_{14}$ aryl, $C_6$–$C_{14}$ arylcarbonyl-3–8-membered heterocycloalkyl, $C_3$–$C_8$ cycloalkylcarbonyl-$C_6$–$C_{14}$ aryl, $C_3$–$C_8$ cycloalkylcarbonyl-3–8-membered heterocycloalkyl, 3–8-membered heterocycloalkyl, 3–8-membered heterocycloalkylcarbonyl-$C_6$–$C_{14}$ aryl, or 3–8-membered heterocycloalkylcarbonyl-3–8-membered heterocycloalkyl;

or $R^{3''}$ and $R^{2''}$ together with the nitrogen of the CHR$^7$NR$^{2''}$R$^{3''}$ group form a second 5-, 6- or 7-membered aliphatic ring, wherein one of the carbons in the second 5-, 6-, or 7-membered aliphatic ring is optionally replaced by O, S, NR$^{11}$, or C=O and the second 5-, 6-, or 7-membered aliphatic ring is optionally substituted with one or two $C_1$–$C_4$ alkyl or optionally substituted with OH, wherein $R^{11}$ is hydrogen, $C_1$–$C_8$ alkyl optionally substituted with 1 to 4 halogens, $C_3$–$C_7$ cycloalkyl-$C_0$–$C_4$ alkyl, $C_6$–$C_{14}$ aryl-$C_0$–$C_4$ alkyl, 5–10-membered heteroaryl-$C_0$–$C_4$ alkyl, or $C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl; and $R^{7'}$ is hydrogen, $C_1$–$C_8$ alkyl optionally substituted with 1 to 4 halogens, $C_3$–$C_7$ cycloalkyl-$C_0$–$C_4$ alkyl, $C_6$–$C_{14}$ aryl-$C_0$–$C_4$ alkyl, 5–10-membered heteroaryl-$C_0$–$C_4$ alkyl, $C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl, or SO$_2$C$_1$–C$_{10}$ alkyl.

2. The compound of claim 1, wherein $R^{10}$ is hydrogen, F or OH.

3. The compound of claim 1, wherein $R^6$ is hydrogen.

4. The compound of claim 1, wherein $R^7$ is methyl.

5. The compound of claim 1, wherein $R^8$ is CHR$^7$NR$^{2''}$R$^{3''}$, wherein $R^{7'}$ is hydrogen and $R^{3''}$ and $R^{2''}$ together with the nitrogen of the CHR$^7$NR$^{2''}$R$^{3''}$ group form a second 5-, 6- or 7-membered aliphatic ring, wherein one of the carbons in the second 5-, 6-, or 7-membered aliphatic ring is optionally replaced by O, S, NR$^{11}$, or CO and the second 5-, 6-, or 7-membered aliphatic ring is optionally substituted with one or two $C_1$–$C_4$ alkyl or optionally substituted with OH, wherein $R^{11}$ is hydrogen, $C_1$–$C_8$ alkyl optionally substituted with 1 to 4 halogens, $C_3$–$C_7$ cycloalkyl-$C_0$–$C_4$ alkyl, $C_6$–$C_{14}$ aryl-$C_0$–$C_4$ alkyl, 5–10-membered heteroaryl-$C_0$–$C_4$ alkyl, or $C_6$–$C_{14}$ aryl-$C_0$–$C_4$ alkylene-O—$C_0$–$C_4$ alkyl, wherein each $C_0$–$C_4$ alkyl and each $C_0$–$C_4$ alkylene is optionally substituted with one to four $C_1$–$C_4$ alkyl.

6. The compound of claim 5, wherein $R^{7'}$ is hydrogen and $R^{3''}$ and $R^{2''}$ together with the nitrogen of the CHR$^7$NR$^{2''}$R$^{3''}$ group form a pyrrolidinyl, 3-hydroxypyrrolidinyl, morpholinyl, or piperidinyl group.

7. The compound of claim 5, wherein $R^{7'}$ is hydrogen and $R^{3''}$ and $R^{2''}$ are each methyl.

8. The compound of claim 1, wherein $R^1$ is selected from the group consisting of a) NR$^2$R$^3$, wherein $R^2$ and $R^3$ are each independently $C_1$–$C_4$ alkyl optionally substituted with a substituent selected from the group consisting of OH, $C_3$–$C_7$ cycloalkyl, $C_1$–$C_4$ dialkylamino, $C_6$–$C_{14}$ aryl optionally substituted with one or more halogens and optionally substituted with $C_6$–$C_{10}$ aryloxy optionally substituted with one to two halogens, and 5–10-membered heteroaryl optionally substituted with a $C_6$–$C_{10}$ aryl group and optionally substituted with one to three $C_1$–$C_4$ alkyl groups;

$C_3$–$C_7$ cycloalkyl;

3–8-membered heterocycloalkyl optionally substituted with one or more $C_1$–$C_4$ alkylcarbonyl groups; and $C_6$–$C_{10}$ arylsulfonyl optionally substituted with one or more $C_1$–$C_2$ alkyl;

or $R^3$ and $R^2$ together with the nitrogen of the NR$^2$R$^3$ group form a first 5, 6, or 7-membered aliphatic ring, wherein one of the carbons in the first 5, 6, or 7-membered aliphatic ring is optionally replaced by O, S, NR$^{2'}$, or CO, and the first 5, 6, or 7-membered aliphatic ring is optionally fused to a $C_6$–$C_{10}$ arylene and is optionally substituted at a ring carbon with a substituent selected from the group consisting of 5–10-membered heteroaryl optionally substituted with one or more halogens and optionally substituted with one or more $C_1$–$C_2$ alkyl, $C_1$–$C_4$ alkoxy optionally substituted with one or more $C_1$–$C_2$ alkoxy and optionally substituted with one or more $C_1$–$C_4$ dialkylaminocarbonyl, and one or two C1–C4 alkyl optionally and independently substituted with one or more $C_1$–$C_2$ alkoxy;

wherein $R^{2'}$ is

5–10-membered heteroaryl optionally substituted with a substituent selected from the group consisting of halogen, $C_1$–$C_4$ alkyl, $C_1$–$C_2$ alkoxy, $C_6$–$C_{10}$ aryl, $C_1$–$C_4$ alkylaminocarbonyl, and cyano;

$C_1$–$C_4$ alkyl optionally substituted with a substituent selected from the group consisting of $C_1$–$C_2$ alkoxycarbonyl and 5–10-membered heteroaryl optionally substituted with one or more $C_1$–$C_2$ alkyl;

$C_6$–$C_{10}$ aryl optionally substituted with one or two $C_1$–$C_2$ alkyl;

or $C_1$–$C_4$ alkylcarbonyl;

b) $OR^4$, wherein $R^4$ is $C_1$–$C_4$ alkyl optionally substituted with $C_6$–$C_{14}$ aryl optionally substituted with a substituent selected from the group consisting of one, two or three halogens, cyano, one or two $C_1$–$C_2$ alkoxy, $C_1$–$C_2$ di- or tri-fluoroalkyl, $C_1$–$C_4$ alkyl optionally substituted with $C_6$–$C_{10}$ arylsulfonyl, nitro, and 5–10-membered heteroaryl;

5–10-membered heteroaryl optionally fused to a $C_6$–$C_{10}$ arylene group that is optionally substituted with one or more halogens or one or more $C_1$–$C_2$ alkoxy, wherein the 5–10-membered heteroaryl is optionally substituted with a substituent selected from the group consisting of:

$C_6$–$C_{10}$ aryl optionally substituted with one or more halogens, one or more $C_1$–$C_2$ alkoxy, or one or more $C_1$–$C_2$ alkyl;

$C_6$–$C_{10}$ arylcarbonyl optionally substituted with one or more halogens;

one or more halogens;

one to three $C_1$–$C_4$ alkyl groups optionally substituted with one or more $C_6$–$C_{10}$ aryl optionally and independently substituted with one or more halogens or one or more $C_1$–$C_2$ alkoxy;

$C_1$–$C_2$ di- or tri-fluoroalkyl;

one or two $C_1$–$C_2$ alkoxy groups;

3–8-membered heterocycloalkyl;

5–10-membered heteroaryl-amino;

$C_1$–$C_2$ alkylaminocarbonyl-$C_1$–$C_2$-alkylamino;

$C_6$–$C_{10}$ arylaminocarbonyl;

$C_6$–$C_{10}$ arylaminocarbonyl-$C_1$–$C_2$-alkylamino optionally substituted with one or more halogens at the $C_6$–$C_{10}$ aryl moiety of $C_6$–$C_{10}$ arylaminocarbonyl;

5–10-membered heteroaryl optionally substituted with one or more $C_6$–$C_{10}$ aryl or one or more $C_1$–$C_2$ alkyl;

$C_6$–$C_{10}$ aryloxy optionally substituted with one or more $C_1$–$C_2$ alkoxy or one or more halogens; and $C_1$–$C_4$ dialkylamino; or $C_6$–$C_{10}$ arylsulfonyl optionally substituted with $C_1$–$C_2$ alkyl; and c) $N_3$.

9. The compound of claim 8, wherein $R^1$ is $NR^2R^3$, wherein $R^2$ and $R^3$ are each independently $C_1$–$C_4$ alkyl.

10. The compound of claim 8, wherein $R^1$ is $NR^2R^3$, wherein $R^3$ and $R^2$ together with the nitrogen of the $NR^2R^3$ group form a first 5, 6, or 7-membered aliphatic ring, wherein one of the carbons in the first 5, 6, or 7-membered aliphatic ring is optionally replaced by O, S, $NR^{2'}$, or CO wherein $R^{2'}$ is $C_1$–$C_4$ alkyl.

11. The compound of claim 8, wherein $R^1$ is pyrrolidinyl, morpholinyl, 3-hydroxypyrrolidinyl, or piperidinyl.

12. The compound of claim 8, wherein $R^1$ is $OR^4$, wherein $R^4$ is $C_1$–$C_4$ alkyl.

13. The compound of claim 1, wherein the compound is selected from the group consisting of:

3-Benzyloxymethyl-1-(4-pyrrolidin-1-ylmethyl-phenyl)-cyclobutanol,

1-[4-(3-Benzyloxymethyl-cyclobutyl)-benzyl]-pyrrolidine,

1-[4-(3-Benzyloxymethyl-cyclobutyl)-benzyl]-pyrrolidine,

[3-(4-Pyrrolidin-1-ylmethyl-phenyl)-cyclobutyl]-methanol,

Toluene-4-sulfonic acid 3-(4-pyrrolidin-1-ylmethyl-phenyl)-cyclobutylmethyl ester, 3-[3-(4-Pyrrolidin-1-ylmethyl-phenyl)-cyclobutylmethoxymethyl]-benzonitrile, 2-[3-(4-Pyrrolidin-1-ylmethyl-phenyl)-cyclobutylmethoxymethyl]-benzonitrile, 4-[3-(4-Pyrrolidin-1-ylmethyl-phenyl)-cyclobutylmethoxymethyl]-benzonitrile, 1-{4-[3-(3-Methoxy-benzyloxymethyl)-cyclobutyl]-benzyl}-pyrrolidine, 1-{4-[3-(3-Fluoro-benzyloxymethyl)-cyclobutyl]-benzyl}-pyrrolidine, 1-{4-[3-(4-Trifluoromethoxy-benzyloxymethyl)-cyclobutyl]-benzyl}-pyrrolidine, 1-(4-{3-[(3-Chloro-2-fluoro-phenyl)methoxymethyl]-cyclobutyl}-benzyl)-pyrrolidine, 1-{4-[3-(3-Methoxy-benzyloxymethyl)-cyclobutyl]-benzyl}-pyrrolidine, 1-(4-{3-[(3,4-Dichloro-phenyl)methoxymethyl]-cyclobutyl}-benzyl)-pyrrolidine, 1-(4-{3-[(3,5-Difluoro-phenyl)methoxymethyl]-cyclobutyl}-benzyl)-pyrrolidine, 1-{4-[3-(3-Methyl-benzyloxymethyl)-cyclobutyl]-benzyl}-pyrrolidine, 1-{4-[3-(3-Fluoro-benzyloxymethyl)-cyclobutyl]-benzyl}-pyrrolidine, 1-{4-[3-(4-Fluoro-benzyloxymethyl)-cyclobutyl]-benzyl}-pyrrolidine, 1-{4-[3-(4-Trifluoromethyl-benzyloxymethyl)-cyclobutyl]-benzyl}-pyrrolidine, 1-(4-{3-[(2,4-Difluoro-phenyl)methoxymethyl]-cyclobutyl}-benzyl)-pyrrolidine, 1-(4-{3-[(3,4-Difluoro-phenyl)methoxymethyl]-cyclobutyl}-benzyl)-pyrrolidine, 1-{4-[3-(3-Trifluoromethyl-benzyloxymethyl)-cyclobutyl]-benzyl}-pyrrolidine, 1-{4-[3-(4-tert-Butyl-benzyloxymethyl)-cyclobutyl]-benzyl}-pyrrolidine, 1-{4-[3-(2-Fluoro-benzyloxymethyl)-cyclobutyl]-benzyl}-pyrrolidine, 1-{4-[3-(3-Difluoromethoxy-benzyloxymethyl)-cyclobutyl]-benzyl}-pyrrolidine, 1-{4-[3-(2-Benzenesulfonylmethyl-benzyloxymethyl)-cyclobutyl]-benzyl}-pyrrolidine, 1-{4-[3-(1-Phenyl-ethoxymethyl)-cyclobutyl]-benzyl}-pyrrolidine, 1-{4-[3-(4-Methyl-benzyloxymethyl)-cyclobutyl]-benzyl}-pyrrolidine, 1-{4-[3-(3-Nitro-benzyloxymethyl)-cyclobutyl]-benzyl}-pyrrolidine, 1-(4-{3-[(2-Methoxy-5-nitro-phenyl)methoxymethyl]-cyclobutyl}-benzyl)-pyrrolidine, 1-{4-[3-(3-Trifluoromethoxy-benzyloxymethyl)-cyclobutyl]-benzyl}-pyrrolidine, 1-(4-{3-[(3,5-Dimethoxy-phenyl)methoxymethyl]-cyclobutyl}-benzyl)-pyrrolidine, 2-[3-(4-Pyrrolidin-1-ylmethyl-phenyl)-cyclobutylmethoxymethyl]-pyridine, 1-(4-{3-[(2,3,4-Trifluoro-phenyl)methoxymethyl]-cyclobutyl}-benzyl)-pyrrolidine, 1-{4-[3-(4-Pyrrolidin-1-ylmethyl-phenyl)-cyclobutylmethoxymethyl]-phenyl}-1H-pyrazole, 1-(4-{3-[(3,5-Dimethyl-phenyl)methoxymethyl]-cyclobutyl}-benzyl)-pyrrolidine,
2-[3-(4-Pyrrolidin-1-ylmethyl-phenyl)-cyclobutylmethoxy]-pyrimidine,
8-Methoxy-2-[3-(4-pyrrolidin-1-ylmethyl-phenyl)-cyclobutylmethoxy]-quinoline,
7-Fluoro-4-methyl-2-[3-(4-pyrrolidin-1-ylmethyl-phenyl)-cyclobutylmethoxy]-quinoline,
4,6-Dimethyl-2-[3-(4-pyrrolidin-1-ylmethyl-phenyl)-cyclobutylmethoxy]-pyrimidine,
2-[3-(4-Pyrrolidin-1-ylmethyl-phenyl)-cyclobutylmethoxy]-pyrazine,
2,5-Dimethyl-3-[3-(4-pyrrolidin-1-ylmethyl-phenyl)-cyclobutylmethoxy]-pyrazine,
2-[3-(4-Pyrrolidin-1-ylmethyl-phenyl)-cyclobutylmethoxy]-pyridine,
2-Methyl-6-[3-(4-pyrrolidin-1-ylmethyl-phenyl)-cyclobutylmethoxy]-pyridine,
3-Methoxy-6-[3-(4-pyrrolidin-1-ylmethyl-phenyl)-cyclobutylmethoxy]-pyridazine,
1-{4-[3-(2-Bromo-benzyloxymethyl)-cyclobutyl]-benzyl}-pyrrolidine,
2,4-Dimethoxy-6-[3-(4-pyrrolidin-1-ylmethyl-phenyl)-cyclobutylmethoxy]-pyrimidine,
cis-Toluene-4-sulfonic acid 3-(4-pyrrolidin-1-ylmethyl-phenyl)-cyclobutylmethyl ester,
trans-Toluene-4-sulfonic acid 3-(4-pyrrolidin-1-ylmethyl-phenyl)-cyclobutylmethyl ester,
trans-[3-(4-Pyrrolidin-1-ylmethyl-phenyl)-cyclobutyl]-methanol,
cis-[3-(4-Pyrrolidin-1-ylmethyl-phenyl)-cyclobutyl]-methanol,
cis4,6-Dimethyl-2-[3-(4-pyrrolidin-1-ylmethyl-phenyl)-cyclobutylmethoxy]-pyrimidine,
cis-2-[3-(4-Pyrrolidin-1-ylmethyl-phenyl)-cyclobutylmethoxy]-pyrimidine,
cis-5-Ethyl-2-[3-(4-pyrrolidin-1-ylmethyl-phenyl)-cyclobutylmethoxy]-pyrimidine,
cis-3-Methyl-6-[3-(4-pyrrolidin-1-ylmethyl-phenyl)-cyclobutylmethoxy]-pyridazine,
trans-4,6-Dimethyl-2-[3-(4-pyrrolidin-1-ylmethyl-phenyl)-cyclobutylmethoxy]-pyrimidine,
trans-2-[3-(4-Pyrrolidin-1-ylmethyl-phenyl)-cyclobutylmethoxy]-pyrimidine,
trans-5-Ethyl-2-[3-(4-pyrrolidin-1-ylmethyl-phenyl)-cyclobutylmethoxy]-pyrimidine,
trans-3-Methyl-6-[3-(4-pyrrolidin-1-ylmethyl-phenyl)-cyclobutylmethoxy]-pyridazine,
cis-5-Methyl-4-piperidin-3-yl-2-[3-(4-pyrrolidin-1-ylmethyl-phenyl)-cyclobutylmethoxy]-pyrimidine,
cis-Pyridin-4-yl-{6-[3-(4-pyrrolidin-1-ylmethyl-phenyl)-cyclobutylmethoxy]-pyridazin-3-yl}-amine,
cis-2-{[3-(4-Pyrrolidin-1-ylmethyl-phenyl)-cyclobutylmethyl]oxy}-4-trifluoromethyl-pyrimidine,
cis-5-Phenyl-2-[3-(4-pyrrolidin-1-ylmethyl-phenyl)-cyclobutylmethoxy]-pyrimidine,
cis-(4-Chloro-phenyl)-{6-[3-(4-pyrrolidin-1-ylmethyl-phenyl)-cyclobutylmethoxy]-pyridazin-3-yl}-methanone,
cis-1,3-Dimethyl-1-{6-[3-(4-pyrrolidin-1-ylmethyl-phenyl)-cyclobutylmethoxy]-pyridazin-3-yl}-urea,
cis-4-Pyrrolidin-3-yl-2-[3-(4-pyrrolidin-1-ylmethyl-phenyl)-cyclobutylmethoxy]-pyrimidine,
cis-4-Methyl-6-pyrrolidin-3-yl-2-[3-(4-pyrrolidin-1-ylmethyl-phenyl)-cyclobutylmethoxy]-pyrimidine,
cis-4-(3-Chloro-phenyl)-2-[3-(4-pyrrolidin-1-ylmethyl-phenyl)-cyclobutylmethoxy]-quinazoline,
cis-3-(3-Chloro-phenyl)-1-methyl-1-{6-[3-(4-pyrrolidin-1-ylmethyl-phenyl)-cyclobutylmethoxy-pyridazin-3-yl}-urea,
cis-5-(4-Methoxy-phenoxy)-2-[3-(4-pyrrolidin-1-ylmethyl-phenyl)-cyclobutylmethoxy]-pyrimidine,
cis-4-Pyridin-2-yl-2-[3-(4-pyrrolidin-1-ylmethyl-phenyl)-cyclobutylmethoxy]-quinazoline,
cis-5-(3-Chloro-phenoxy)-2-[3-(4-pyrrolidin-1-ylmethyl-phenyl)-cyclobutylmethoxy]-pyrimidine,
cis-4-Phenyl-6-piperidin-4-yl-2-[3-(4-pyrrolidin-1-ylmethyl-phenyl)-cyclobutylmethoxy]-pyrimidine,
cis-3-(3-Methyl-5-phenyl-pyrazol-1-yl)-6-{[3-(4-pyrrolidin-1-ylmethyl-phenyl)-cyclobutylmethyl]oxy}-pyridazine,
5-Fluoro-4-piperidin-4-yl-2-[3-(4-pyrrolidin-1-ylmethyl-phenyl)-cyclobutylmethoxy]-pyrimidine,
cis-3-piperazin-1-yl-6-[3-(4-pyrrolidin-1-ylmethyl-phenyl)-cyclobutylmethoxy]-pyridazine,
cis-4-Phenyl-2-{[3-(4-pyrrolidin-1-ylmethyl-phenyl)-cyclobutylmethyl]oxy}-6-trifluoromethyl-pyrimidine,
cis-4-Methyl-6-piperidin-4-yl-2-[3-(4-pyrrolidin-1-ylmethyl-phenyl)-cyclobutylmethoxy]-pyrimidine,
cis-1-Methyl-4-[3-(4-pyrrolidin-1-ylmethyl-phenyl)-cyclobutylmethoxy]-phthalazine,
cis-2-[3-(4-Pyrrolidin-1-ylmethyl-phenyl)-cyclobutylmethoxy]-4-o-tolyl-pyrimidine,
cis-5-(5-Iodo-2-methoxy-benzyl)-3-{[3-(4-pyrrolidin-1-ylmethyl-phenyl)-cyclobutyl]methoxy}-pyridazine,
cis-5-Methyl-4-piperidin-4-yl-2-[3-(4-pyrrolidin-1-ylmethyl-phenyl)-cyclobutylmethoxy]-pyrimidine,
cis-4-(2-Methyl-2H-pyrazol-3-yl)-2-[3-(4-pyrrolidin-1-ylmethyl-phenyl)-cyclobutylmethoxy]-quinazoline,
cis-6-Methyl-2-[3-(4-pyrrolidin-1-ylmethyl-phenyl)-cyclobutylmethoxy]-pyrimidine-4-carboxylic acid phenylamide,
cis-4-Phenyl-2-[3-(4-pyrrolidin-1-ylmethyl-phenyl)-cyclobutylmethoxy]-pyrimidine,
cis-3-(2-Methoxy-benzyl)-6-[3-(4-pyrrolidin-1-ylmethyl-phenyl)-cyclobutylmethoxy]-pyridazine,
cis-Dimethyl-{6-[3-(4-pyrrolidin-1-ylmethyl-phenyl)-cyclobutylmethoxy]-pyridazin-3-yl}-amine,
cis-4-Methyl-6-phenyl-2-[3-(4-pyrrolidin-1-ylmethyl-phenyl)-cyclobutylmethoxy]-pyrimidine,
cis-5-Methyl-4-pyrrolidin-3-yl-2-[3-(4-pyrrolidin-1-ylmethyl-phenyl)-cyclobutylmethoxy]-pyrimidine,
cis-3-(3,5-Dimethyl-pyrazol-1-yl)-6-{[3-(4-pyrrolidin-1-ylmethyl-phenyl)-cyclobutylmethyl]oxy}-pyridazine,
cis-3-(2,5-Dimethyl-pyrrol-1-yl)-6-{[3-(4-pyrrolidin-1-ylmethyl-phenyl)-cyclobutylmethyl]oxy}-pyridazine,
cis-5-(3-Chloro-phenyl)-2-[3-(4-pyrrolidin-1-ylmethyl-phenyl)-cyclobutylmethoxy]-pyrimidine,
cis-5-(4-Methoxy-phenyl)-2-[3-(4-pyrrolidin-1-ylmethyl-phenyl)-cyclobutylmethoxy]-pyrimidine,
cis-4-Phenyl-6-pyridin-2-yl-2-[3-(4-pyrrolidin-1-ylmethyl-phenyl)-cyclobutylmethoxy]-pyrimidine,
cis-4-Phenyl-6-pyridin-3-yl-2-[3-(4-pyrrolidin-1-ylmethyl-phenyl)-cyclobutylmethoxy]-pyrimidine,
2-{4-[3-(4-Pyrrolidin-1-ylmethyl-phenyl)-cyclobutylmethyl]-piperazin-1-yl}-pyrimidine,
Dimethyl-[3-(4-pyrrolidin-1-ylmethyl-phenyl)-cyclobutylmethyl]-amine,
1-{4-[3-(4-Pyrrolidin-1-ylmethyl-phenyl)-cyclobutylmethyl]-piperazin-1-yl}-ethanone,
4-[3-(4-Pyrrolidin-1-ylmethyl-phenyl)-cyclobutylmethyl]-morpholine,
5-Fluoro-2-{4-[3-(4-pyrrolidin-1-ylmethyl-phenyl)-cyclobutylmethyl]-piperazin-1-yl}-pyrimidine, cis-4-[3-(4-Pyrrolidin-1-ylmethyl-phenyl)-cyclobutylmethyl]-morpholine,
cis-1-[3-(4-Pyrrolidin-1-ylmethyl-phenyl)-cyclobutylmethyl]-piperazine,
cis-5-Fluoro-2-{4-[3-(4-pyrrolidin-1-ylmethyl-phenyl)-cyclobutylmethyl]-piperazin-1-yl}-pyrimidine,
cis-1-[3-(4-Pyrrolidin-1-ylmethyl-phenyl)-cyclobutylmethyl]-pyrrolidine,
cis-1-[3-(4-Pyrrolidin-1-ylmethyl-phenyl)-cyclobutylmethyl]-piperidine,
cis-2-{1-[3-(4-Pyrrolidin-1-ylmethyl-phenyl)-cyclobutylmethyl]-pyrrolidin-2-yl}-pyridine,
cis-(2R,6S)-2,6-Dimethyl-4-[3-(4-pyrrolidin-1-ylmethyl-phenyl)-cyclobutylmethyl]-morpholine,
trans-1-[3-(4-Pyrrolidin-1-ylmethyl-phenyl)-cyclobutylmethyl]-pyrrolidine,
trans-1-[3-(4-Pyrrolidin-1-ylmethyl-phenyl)-cyclobutylmethyl]-piperidine,
trans-2-{1-[3-(4-Pyrrolidin-1-ylmethyl-phenyl)-cyclobutylmethyl]-pyrrolidin-2-yl}-pyridine,
trans-4-[3-(4-Pyrrolidin-1-ylmethyl-phenyl)-cyclobutylmethyl]-morpholine,
trans-1-[3-(4-Pyrrolidin-1-ylmethyl-phenyl)-cyclobutylmethyl]-piperazineyl paratoluenesulfonate,
trans-5-Fluoro-2-{4-[3-(4-pyrrolidin-1-ylmethyl-phenyl)-cyclobutylmethyl]-piperazin-1-yl}-pyrimidine,
trans-2-{Ethyl-[3-(4-pyrrolidin-1-ylmethyl-phenyl)-cyclobutylmethyl]-amino}-ethanol,
trans-3,5-Dimethyl-1-[3-(4-pyrrolidin-1-ylmethyl-phenyl)-cyclobutylmethyl]-piperidine,
trans-Cyclohexyl-methyl-[3-(4-pyrrolidin-1-ylmethyl-phenyl)-cyclobutylmethyl]-amine,
trans-Benzyl-methyl-[3-(4-pyrrolidin-1-ylmethyl-phenyl)-cyclobutylmethyl]-amine,
trans-2-Methyl-1-[3-(4-pyrrolidin-1-ylmethyl-phenyl)-cyclobutylmethyl]-piperidine,
trans-3-Methyl-1-[3-(4-pyrrolidin-1-ylmethyl-phenyl)-cyclobutylmethyl]-piperidine,
trans-4-Methyl-1-[3-(4-pyrrolidin-1-ylmethyl-phenyl)-cyclobutylmethyl]-piperidine,
trans-2-Methyl-1-[3-(4-pyrrolidin-1-ylmethyl-phenyl)-cyclobutylmethyl]-pyrrolidine,
trans-2,6-Dimethyl-1-[3-(4-pyrrolidin-1-ylmethyl-phenyl)-cyclobutylmethyl]-piperidine,
trans-Methyl-pyridin-3-ylmethyl-[3-(4-pyrrolidin-1-ylmethyl-phenyl)-cyclobutylmethyl]-amine,
trans-(2R,5R)-2,5-Dimethyl-1-[3-(4-pyrrolidin-1-ylmethyl-phenyl)-cyclobutylmethyl]-pyrrolidine,
trans-Cyclopropylmethyl-propyl-[3-(4-pyrrolidin-1-ylmethyl-phenyl)-cyclobutylmethyl]-amine,
trans-2-[3-(4-Pyrrolidin-1-ylmethyl-phenyl)-cyclobutylmethyl]-2,3-dihydro-1H-isoindole,
trans-(2R,6S)-2,6-Dimethyl-4-[3-(4-pyrrolidin-1-ylmethyl-phenyl)-cyclobutylmethyl]-morpholine,
trans-4-[3-(4-Pyrrolidin-1-ylmethyl-phenyl)-cyclobutylmethyl]-piperazin-2-one,
trans-(S)-2-Methoxymethyl-1-[3-(4-pyrrolidin-1-ylmethyl-phenyl)-cyclobutylmethyl]-pyrrolidine,
trans-(3,5-Bis-trifluoromethyl-benzyl)-{[3-(4-pyrrolidin-1-ylmethyl-phenyl)-cyclobutyl]methyl}-amine,
trans-(5-Methyl-pyrazin-2-ylmethyl)-[3-(4-pyrrolidin-1-ylmethyl-phenyl)-cyclobutylmethyl]-amine,
trans-(2-Methyl-pyridin-3-ylmethyl)-[3-(4-pyrrolidin-1-ylmethyl-phenyl)-cyclobutylmethyl]-amine,
trans-Pyridin-2-ylmethyl-[3-(4-pyrrolidin-1-ylmethyl-phenyl)-cyclobutylmethyl]-amine,
trans-trans-2-{4-[3-(4-Pyrrolidin-1-ylmethyl-phenyl)-cyclobutylmethyl]-piperazin-1-yl}-isonicotinonitrile,
trans-Methyl-pyridin-2-ylmethyl-[3-(4-pyrrolidin-1-ylmethyl-phenyl)-cyclobutylmethyl]-amine,
trans-(3-Chloro-5-trifluoromethyl-pyridin-2-ylmethyl)-{[3-(4-pyrrolidin-1-ylmethyl-phenyl)-cyclobutyl]methyl}-amine,
trans-3-Ethyl-5-{(R)-1-[3-(4-pyrrolidin-1-ylmethyl-phenyl)-cyclobutylmethyl]-pyrrolidin-2-yl}-[1,2,4]oxadiazole,
trans-(6-Methyl-pyridin-2-ylmethyl)-[3-(4-pyrrolidin-1-ylmethyl-phenyl)-cyclobutylmethyl]-amine,
trans-(2-Chloro-6-fluoro-benzyl)-propyl-[3-(4-pyrrolidin-1-ylmethyl-phenyl)-cyclobutylmethyl]-amine,
trans-[3-(3,5-Dimethyl-pyrazol-1-yl)-benzyl]-methyl-[3-(4-pyrrolidin-1-ylmethyl-phenyl)-cyclobutylmethyl]-amine,
trans-1-(5-Chloro-2-methoxy-benzyl)-4-[3-(4-pyrrolidin-1-ylmethyl-phenyl)-cyclobutylmethyl]-piperazine,
trans-(3S,4aS,8aS)-2-[3-(4-Pyrrolidin-1-ylmethyl-phenyl)-cyclobutylmethyl]-decahydro-isoquinoline-3-carboxylic acid tert-butylamide,
trans-(1-Benzyl-piperidin-4-ylmethyl)-methyl-[3-(4-pyrrolidin-1-ylmethyl-phenyl)-cyclobutylmethyl]-amine,
trans-(S)-1-[3-(4-Pyrrolidin-1-ylmethyl-phenyl)-cyclobutylmethyl]-pyrrolidine-2-carboxylic acid amide,
trans-(8-Methoxy-quinolin-5-ylmethyl)-methyl-[3-(4-pyrrolidin-1-ylmethyl-phenyl)-cyclobutylmethyl]-amine,
trans-4-(4-Chloro-phenoxy)-1-[3-(4-pyrrolidin-1-ylmethyl-phenyl)-cyclobutylmethyl]-piperidine,
trans-4-(2-Methoxy-phenoxy)-1-[3-(4-pyrrolidin-1-ylmethyl-phenyl)-cyclobutylmethyl]-piperidine,
trans-4-(3-Chloro-phenoxy)-1-[3-(4-pyrrolidin-1-ylmethyl-phenyl)-cyclobutylmethyl]-piperidine,
trans-Methyl-(4-phenoxy-benzyl)-[3-(4-pyrrolidin-1-ylmethyl-phenyl)-cyclobutylmethyl]-amine,
trans-[1-(2-Methoxy-ethyl)-piperidin-4-ylmethyl]-methyl-[3-(4-pyrrolidin-1-ylmethyl-phenyl)-cyclobutylmethyl]-amine,
trans-1-[3-(4-Pyrrolidin-1-ylmethyl-phenyl)-cyclobutylmethyl]-4-p-tolyloxy-piperidine,
trans-2-{Benzyl-[3-(4-pyrrolidin-1-ylmethyl-phenyl)-cyclobutylmethyl]-amino}-ethanol,
trans-[2-(3,4-Dimethoxy-phenyl)-ethyl]-methyl-[3-(4-pyrrolidin-1-ylmethyl-phenyl)-cyclobutylmethyl]-amine,
trans-Methyl-prop-2-ynyl-[3-(4-pyrrolidin-1-ylmethyl-phenyl)-cyclobutylmethyl]-amine,
trans-4-Pyrrolidin-1-yl-1-[3-(4-pyrrolidin-1-ylmethyl-phenyl)-cyclobutylmethyl]-piperidine,
trans-Isopropyl-(2-methoxy-ethyl)-[3-(4-pyrrolidin-1-ylmethyl-phenyl)-cyclobutylmethyl]-amine,
trans-1-Benzyl-4-[3-(4-pyrrolidin-1-ylmethyl-phenyl)-cyclobutylmethyl]-piperazine,
trans-1-Ethyl-4-[3-(4-pyrrolidin-1-ylmethyl-phenyl)-cyclobutylmethyl]-piperazine,
trans-2-{Isopropyl-[3-(4-pyrrolidin-1-ylmethyl-phenyl)-cyclobutylmethyl]-amino}-ethanol,
trans-(2-Methoxy-ethyl)-propyl-[3-(4-pyrrolidin-1-ylmethyl-phenyl)-cyclobutylmethyl]-amine,
trans-Methyl-((R)-1-phenyl-ethyl)-[3-(4-pyrrolidin-1-ylmethyl-phenyl)-cyclobutylmethyl]-amine,
trans-(4S,4aS)-4-Phenyl-1-[3-(4-pyrrolidin-1-ylmethyl-phenyl)-cyclobutylmethyl]-decahydro-quinolin-4-ol,
trans-1-{4-[3-(4-Pyrrolidin-1-ylmethyl-phenyl)-cyclobutylmethyl]-piperazin-1-yl}-ethanone, trans-1-Methyl-4-[3-(4-pyrrolidin-1-ylmethyl-phenyl)-cyclobutylmethyl]-[1,4]diazepane,
trans-2-{4-[3-(4-Pyrrolidin-1-ylmethyl-phenyl)-cyclobutylmethyl]-piperazin-1-yl}-nicotinonitrile,
trans-Ethyl-(2-methoxy-ethyl)-[3-(4-pyrrolidin-1-ylmethyl-phenyl)-cyclobutylmethyl]-amine,
trans-Methyl-(3-methyl-pyridin-2-ylmethyl)-[3-(4-pyrrolidin-1-ylmethyl-phenyl)-cyclobutylmethyl]-amine,
trans-Diethyl-[3-(4-pyrrolidin-1-ylmethyl-phenyl)-cyclobutylmethyl]-amine,
trans-Benzyl-isopropyl-[3-(4-pyrrolidin-1-ylmethyl-phenyl)-cyclobutylmethyl]-amine,
trans-(S)-2-Pyrrolidin-1-ylmethyl-1-[3-(4-pyrrolidin-1-ylmethyl-phenyl)-cyclobutylmethyl]-pyrrolidine,
trans-((S)-1-Benzyl-pyrrolidin-3-yl)-ethyl-[3-(4-pyrrolidin-1-ylmethyl-phenyl)-cyclobutylmethyl]-amine,
trans-tert-Butyl-(2-methoxy-ethyl)-[3-(4-pyrrolidin-1-ylmethyl-phenyl)-cyclobutylmethyl]-amine,
trans-4-(2-Chloro-phenoxy)-1-[3-(4-pyrrolidin-1-ylmethyl-phenyl)-cyclobutylmethyl]-piperidine,
trans-N-Ethyl-N',N'-dimethyl-N-[3-(4-pyrrolidin-1-ylmethyl-phenyl)-cyclobutylmethyl]-ethane-1,2-diamine,
trans-Dicyclopropylmethyl-methyl-[3-(4-pyrrolidin-1-ylmethyl-phenyl)-cyclobutylmethyl]-amine,
trans-Butyl-methyl-[3-(4-pyrrolidin-1-ylmethyl-phenyl)-cyclobutylmethyl]-amine,
trans-N,N,N'-Trimethyl-N'-[3-(4-pyrrolidin-1-ylmethyl-phenyl)-cyclobutylmethyl]-ethane-1,2-diamine,
trans-1-(1-Methyl-1H-imidazol-2-ylmethyl)-4-[3-(4-pyrrolidin-1-ylmethyl-phenyl)-cyclobutylmethyl]-piperazine,
trans-2,5-Dimethyl-1-[3-(4-pyrrolidin-1-ylmethyl-phenyl)-cyclobutylmethyl]-2,5-dihydro-1H-pyrrole,
trans-((S)-1-Benzyl-pyrrolidin-3-yl)-methyl-[3-(4-pyrrolidin-1-ylmethyl-phenyl)-cyclobutylmethyl]-amine,
trans-(4-Fluoro-benzyl)-methyl-[3-(4-pyrrolidin-1-ylmethyl-phenyl)-cyclobutylmethyl]-amine,
trans-1-Phenyl-8-[3-(4-pyrrolidin-1-ylmethyl-phenyl)-cyclobutylmethyl]-1,3,8-triaza-spiro[4.5]decan-4-one,
trans-2{Methyl-[3-(4-pyrrolidin-1-ylmethyl-phenyl)-cyclobutylmethyl]-amino}-ethanol,
trans-3-Benzyl-7-[3-(4-pyrrolidin-1-ylmethyl-phenyl)-cyclobutylmethyl]-5,6,7,8-tetrahydro-[1,2,4]triazolo[4,3-a]pyrazine,
trans-3-{Benzyl-[3-(4-pyrrolidin-1-ylmethyl-phenyl)-cyclobutylmethyl]-amino}-propan-1-ol,
trans-Isobutyl-methyl-[3-(4-pyrrolidin-1-ylmethyl-phenyl)-cyclobutylmethyl]-amine,
trans-Ethyl-isopropyl-[3-(4-pyrrolidin-1-ylmethyl-phenyl)-cyclobutylmethyl]-amine,
trans-Dimethyl-{(R)-1-[3-(4-pyrrolidin-1-ylmethyl-phenyl)-cyclobutylmethyl]-pyrrolidin-3-yl}-amine,
trans-Isopropyl-methyl-[3-(4-pyrrolidin-1-ylmethyl-phenyl)-cyclobutylmethyl]-amine,
trans-Methyl-(5-propyl-1H-pyrazol-3-ylmethyl)-[3-(4-pyrrolidin-1-ylmethyl-phenyl)-cyclobutylmethyl]-amine,
trans-(1R,2S)-2-{Methyl-[3-(4-pyrrolidin-1-ylmethyl-phenyl)-cyclobutylmethyl]-amino}-1-phenyl-propan-1-ol,
trans-2-{1-[3-(4-Pyrrolidin-1-ylmethyl-phenyl)-cyclobutylmethyl]-piperidin-4-yl}-benzooxazole,
trans-3-Propyl-7-[3-(4-pyrrolidin-1-ylmethyl-phenyl)-cyclobutylmethyl]-5,6,7,8-tetrahydro-[1,2,4]triazolo[4,3-a]pyrazine,
trans-Benzyl-((R)-1-phenyl-ethyl)-[3-(4-pyrrolidin-1-ylmethyl-phenyl)-cyclobutylmethyl]-amine,
trans-tert-Butyl-ethyl-[3-(4-pyrrolidin-1-ylmethyl-phenyl)-cyclobutylmethyl]-amine,
trans-1-Methyl-4-[3-(4-pyrrolidin-1-ylmethyl-phenyl)-cyclobutylmethyl]-piperazine,
trans-Isopropyl-[3-(4-pyrrolidin-1-ylmethyl-phenyl)-cyclobutylmethyl]-(1,3,5-trimethyl-1H-pyrazol-4-ylmethyl)-amine,
trans-4-{Benzyl-[3-(4-pyrrolidin-1-ylmethyl-phenyl)-cyclobutylmethyl]-amino}-butan-1-ol,
trans-(1R,2R)-2-{Methyl-[3-(4-pyrrolidin-1-ylmethyl-phenyl)-cyclobutylmethyl]-amino}-1-phenyl-propan-1-ol,
trans-Benzyl-ethyl-[3-(4-pyrrolidin-1-ylmethyl-phenyl)-cyclobutylmethyl]-amine,
trans-6-{4-[3-(4-Pyrrolidin-1-ylmethyl-phenyl)-cyclobutylmethyl]-piperazin-1-yl}-nicotinonitrile,
trans-Methyl-[3-(4-pyrrolidin-1-ylmethyl-phenyl)-cyclobutylmethyl]-(2-trifluoromethyl-benzyl)-amine,
trans-3-(3-Methoxy-phenyl)-6-[3-(4-pyrrolidin-1-ylmethyl-phenyl)-cyclobutylmethyl]-5,6,7,8-tetrahydro-4H-1,2,3a,6-tetraaza-azulene,
trans-Methyl-phenethyl-[3-(4-pyrrolidin-1-ylmethyl-phenyl)-cyclobutylmethyl]-amine,
trans-3-{Pyridin-2-ylmethyl-[3-(4-pyrrolidin-1-ylmethyl-phenyl)-cyclobutylmethyl]-amino}-propan-1-ol,
trans-Bis-pyridin-2-ylmethyl-[3-(4-pyrrolidin-1-ylmethyl-phenyl)-cyclobutylmethyl]-amine,
trans-Bis-(3-chloro-benzyl)-[3-(4-pyrrolidin-1-ylmethyl-phenyl)-cyclobutylmethyl]-amine,
trans-Cyclopropyl-[3-(4-pyrrolidin-1-ylmethyl-phenyl)-cyclobutylmethyl]-(1,3,5-trimethyl-1H-pyrazol-4-ylmethyl)-amine,
trans-Methyl-pyridin-4-ylmethyl-[3-(4-pyrrolidin-1-ylmethyl-phenyl)-cyclobutylmethyl]-amine,
trans-3-(3,4-Difluoro-phenyl)-6-[3-(4-pyrrolidin-1-ylmethyl-phenyl)-cyclobutylmethyl]-5,6,7,8-tetrahydro-4H-1,2,3a,6-tetraaza-azulene,
3-Pyrrolidin-1-ylmethyl-1-(4-pyrrolidin-1-ylmethyl-phenyl)-cyclobutanol,
1-(4-Piperidin-1-ylmethyl-phenyl)-3-pyrrolidin-1-ylmethyl-cyclobutanol,
1-(4-Benzyloxymethyl-phenyl)-3-pyrrolidin-1-ylmethyl-cyclobutanol,
4-(1-Hydroxy-3-pyrrolidin-1-ylmethyl-cyclobutyl)-benzonitrile,
1-(4-Morpholin-4-ylmethyl-phenyl)-3-piperidin-1-ylmethyl-cyclobutanol,
3-Morpholin-4-ylmethyl-1-(4-morpholin-4-ylmethyl-phenyl)-cyclobutanol,
1-(4-Dimethylaminomethyl-phenyl)-3-pyrrolidin-1-ylmethyl-cyclobutanol,
3-(4-Pyrimidin-2-yl-piperazin-1-ylmethyl)-1-(4-pyrrolidin-1-ylmethyl-phenyl)-cyclobutanol,
1-[4-(3-Pyrrolidin-1-ylmethyl-cyclobutyl)-benzyl]-pyrroline,
4-[4-(3-Piperidin-1-ylmethyl-cyclobutyl)-benzyl]-morpholine,
1-[4-(3-Pyrrolidin-1-ylmethyl-cyclobutyl)-benzyl]-piperidine,
Dimethyl-[4-(3-pyrrolidin-1-ylmethyl-cyclobutyl)-benzyl]-amine,
4-(3-Pyrrolidin-1-ylmethyl-cyclobutyl)-benzonitrile,
4-(3-Pyrrolidin-1-ylmethyl-cyclobutyl)-N-hydroxy-benzamidine,
5-Methyl-3-[4-(3-pyrrolidin-1-ylmethyl-cyclobutyl)-phenyl]-[1,2,4]oxadiazole,
4-(3-Pyrrolidin-1-ylmethyl-cyclobutyl)-benzylamine, 1-(3-p-Tolyl-cyclobutylmethyl)-pyrrolidine, trans-1-[4-(3-Benzyloxymethyl-cyclobutyl)-benzyl]-pyrrolidine, and trans-1-[4-(3-Azidomethyl-cyclobutyl)-benzyl]-pyrrolidine.

14. The compound of claim 1, wherein the compound is selected from the group consisting of:

trans-2-[3-(4-Pyrrolidin-1-ylmethyl-phenyl)-cyclobutylmethoxy]-pyrimidine;

trans-5-Ethyl-2-[3-(4-pyrrolidin-1-ylmethyl-phenyl)-cyclobutylmethoxy]-pyrimidine;

trans-3-Methyl-6-[3-(4-pyrrolidin-1-ylmethyl-phenyl)-cyclobutylmethoxy]-pyridazine;

cis-5-Methyl-4-piperidin-3-yl-2-[3-(4-pyrrolidin-1-ylmethyl-phenyl)-cyclobutylmethoxy]-pyrimidine;

cis-Pyridin-4-yl-{6-[3-(4-pyrrolidin-1-ylmethyl-phenyl)-cyclobutylmethoxy]-pyridazin-3-yl}-amine;

cis-2-{[3-(4-Pyrrolidin-1-ylmethyl-phenyl)-cyclobutylmethyl]oxy}-4-trifluoromethyl-pyrimidine;

cis-5-Phenyl-2-[3-(4-pyrrolidin-1-ylmethyl-phenyl)-cyclobutylmethoxy]-pyrimidine;

cis-(4-Chloro-phenyl)-{6-[3-(4-pyrrolidin-1-ylmethyl-phenyl)-cyclobutylmethoxy]-pyridazin-3-yl}-methanone;

cis-1,3-Dimethyl-1-{6-[3-(4-pyrrolidin-1-ylmethyl-phenyl)-cyclobutylmethoxy]-pyridazin-3-yl}-urea;

cis-4-Pyrrolidin-3-yl-2-[3-(4-pyrrolidin-1-ylmethyl-phenyl)-cyclobutylmethoxy]-pyrimidine;

cis-4-Methyl-6-pyrrolidin-3-yl-2-[3-(4-pyrrolidin-1-ylmethyl-phenyl)-cyclobutylmethoxy]-pyrimidine;

cis-4-(3-Chloro-phenyl)-2-[3-(4-pyrrolidin-1-ylmethyl-phenyl)-cyclobutylmethoxy]-quinazoline;

cis-3-(3-Chloro-phenyl)-1-methyl-1-{6-[3-(4-pyrrolidin-1-ylmethyl-phenyl)-cyclobutylmethoxy]-pyridazin-3-yl}-urea;

cis-5-(4-Methoxy-phenoxy)-2-[3-(4-pyrrolidin-1-ylmethyl-phenyl)-cyclobutylmethoxy]-pyrimidine;

cis-4-Pyridin-2-yl-2-[3-(4-pyrrolidin-1-ylmethyl-phenyl)-cyclobutylmethoxy]-quinazoline;

cis-5-(3-Chloro-phenoxy)-2-[3-(4-pyrrolidin-1-ylmethyl-phenyl)-cyclobutylmethoxy]-pyrimidine;

cis-4-Phenyl-6-piperidin-4-yl-2-[3-(4-pyrrolidin-1-ylmethyl-phenyl)-cyclobutylmethoxy]-pyrimidine;

cis-3-(3-Methyl-5-phenyl-pyrazol-1-yl)-6-{[3-(4-pyrrolidin-1-ylmethyl-phenyl)-cyclobutylmethyl]oxy}-pyridazine;

5-Fluoro-4-piperidin-4-yl-2-[3-(4-pyrrolidin-1-ylmethyl-phenyl)-cyclobutylmethoxy]-pyrimidine;

cis-3-piperazin-1-yl-6-[3-(4-pyrrolidin-1-ylmethyl-phenyl)-cyclobutylmethoxy]-pyridazine;

cis-4-Phenyl-2-{[3-(4-pyrrolidin-1-ylmethyl-phenyl)-cyclobutylmethyl]oxy}-6-trifluoromethyl-pyrimidine;

cis-4-Methyl-6-piperidin-4-yl-2-[3-(4-pyrrolidin-1-ylmethyl-phenyl)-cyclobutylmethoxy]-pyrimidine;

cis-1-Methyl-4-[3-(4-pyrrolidin-1-ylmethyl-phenyl)-cyclobutylmethoxy]-phthalazine;

cis-2-[3-(4-Pyrrolidin-1-ylmethyl-phenyl)-cyclobutylmethoxy]-4-o-tolyl-pyrimidine;

cis-5-(5-Iodo-2-methoxy-benzyl)-3-{[3-(4-pyrrolidin-1-ylmethyl-phenyl)-cyclobutyl-methoxy}-pyridazine;

cis-5-Methyl-4-piperidin-4-yl-2-[3-(4-pyrrolidin-1-ylmethyl-phenyl)-cyclobutylmethoxy]-pyrimidine;

cis-4-(2-Methyl-2H-pyrazol-3-yl)-2-[3-(4-pyrrolidin-1-ylmethyl-phenyl)-cyclobutylmethoxy]-quinazoline;

cis-6-Methyl-2[3-(4-pyrrolidin-1-ylmethyl-phenyl)-cyclobutylmethoxy]-pyrimidine-4-carboxylic acid phenylamide;

cis-4-Phenyl-2-[3-(4-pyrrolidin-1-ylmethyl-phenyl)-cyclobutylmethoxy]-pyrimidine;

cis-3-(2-Methoxy-benzyl)-6-[3-(4-pyrrolidin-1-ylmethyl-phenyl)-cyclobutylmethoxy]-pyridazine;

cis-Dimethyl-{6-[3-(4-pyrrolidin-1-ylmethyl-phenyl)-cyclobutylmethoxy]-pyridazin-3-yl}-amine;

cis-4-Methyl-6-phenyl-2-[3-(4-pyrrolidin-1-ylmethyl-phenyl)-cyclobutylmethoxy]-pyrimidine;

cis-5-Methyl-4-pyrrolidin-3-yl-2-[3-(4-pyrrolidin-1-ylmethyl-phenyl)-cyclobutylmethoxy]-pyrimidine;

cis-3-(3,5-Dimethyl-pyrazol-1-yl)-6-{[3-(4-pyrrolidin-1-ylmethyl-phenyl)-cyclobutylmethyl]oxy}-pyridazine;

cis-3-(2,5-Dimethyl-pyrrol-1-yl)-6-{[3-(4-pyrrolidin-1-ylmethyl-phenyl)-cyclobutylmethyl]oxy}-pyridazine;

cis-5-(3-Chloro-phenyl)-2-[3-(4-pyrrolidin-1-ylmethyl-phenyl)-cyclobutylmethoxy]-pyrimidine;

cis-5-(4-Methoxy-phenyl)-2-[3-(4-pyrrolidin-1-ylmethyl-phenyl)-cyclobutylmethoxy]-pyrimidine;

cis-4-Phenyl-6-pyridin-2-yl-2-[3-(4-pyrrolidin-1-ylmethyl-phenyl)-cyclobutylmethoxy]-pyrimidine;

cis-4-Phenyl-6-piperidin-3-yl-2-[3-(4-pyrrolidin-1-ylmethyl-phenyl)-cyclobutylmethoxy]-pyrimidine;

2-{4-[3-(4-Pyrrolidin-1-ylmethyl-phenyl)-cyclobutylmethyl]-piperazin-1-yl}-pyrimidine;

Dimethyl-[3-(4-pyrrolidin-1-ylmethyl-phenyl)-cyclobutylmethyl]-amine;

1-{4-[3-(4-Pyrrolidin-1-ylmethyl-phenyl)-cyclobutylmethyl]-piperazin-1-yl}-ethanone;

4-[3-(4-Pyrrolidin-1-ylmethyl-phenyl)-cyclobutylmethyl]-morpholine;

5-Fluoro-2-{4-[3-(4-pyrrolidin-1-ylmethyl-phenyl)-cyclobutylmethyl]-piperazin-1-yl}-pyrimidine; and cis-4-[3-(4-Pyrrolidin-1-ylmethyl-phenyl)-cyclobutylmethyl]-morpholine.

15. The compound of claim 1, wherein the compound is selected from the group consisting of:

trans-4-[3-(4-Pyrrolidin-1-ylmethyl-phenyl)-cyclobutylmethyl]-thiomorpholine;

trans-6-{4-[3-(4-Pyrrolidin-1-ylmethyl-phenyl)-cyclobutylmethyl]-piperazin-1-yl}-nicotinonitrile;

trans-1-Methanesulfonyl-4-[3-(4-pyrrolidin-1-ylmethyl-phenyl)-cyclobutylmethyl]-piperazine;

trans-1-Ethanesulfonyl-4-[3-(4-pyrrolidin-1-ylmethyl-phenyl)-cyclobutylmethyl]-piperazine;

trans-1-(Propane-2-sulfonyl)-4-[3-(4-pyrrolidin-1-ylmethyl-phenyl)-cyclobutylmethyl]-piperazine;

trans-2-Methyl-1-{4-[3-(4-pyrrolidin-1-ylmethyl-phenyl)-cyclobutylmethyl]-piperazin-1-yl}-propan-1-one;

trans-(1S,4S)-2-Methanesulfonyl-5-[3-(4-pyrrolidin-1-ylmethyl-phenyl)-cyclobutylmethyl]-2,5-diaza-bicyclo[2.2.1]heptane;

cis-1-{4-[3-(4-Pyrrolidin-1-ylmethyl-phenyl)-cyclobutylmethyl]-piperazin-1-yl}-ethanone; and cis-4-[3-(4-Pyrrolidin-1-ylmethyl-phenyl)-cyclobutylmethyl]-thiomorpholine.

16. A pharmaceutical composition comprising a compound of formula I as described in claim 1, and optionally a pharmaceutically acceptable carrier.

17. A method of treatment of a disorder or condition selected from the group consisting of depression, mood disorders, schizophrenia, anxiety disorders, attention-deficit hyperactivity disorder (ADHD), psychotic disorders, sleep disorders, obesity, dizziness, epilepsy, motion sickness, allergy, allergy-induced airway responses, allergic rhinitis, nasal congestion, allergic congestion, congestion, hypotension, diseases of the GI tract, hyper and hypo motility and acidic secretion of the gastro-intestinal tract, the method comprising administering to a mammal in need of such treatment a compound of formula I as described in claim 1.

18. A composition comprising a compound of formula I as defined in claim 1, a histamine $H_1$ antagonist, and optionally a pharmaceutically acceptable carrier.

19. A method of treating a condition selected from the group consisting of allergic rhinitis, nasal congestion, and allergic congestion in a mammal, the method comprising administering a compound of formula I as defined in claim 1 and a histamine $H_1$ antagonist to a mammal in need of such treatment.

20. A composition comprising a compound of formula I as defined in claim 1, a neurotransmitter re-uptake blocker and optionally a pharmaceutically acceptable carrier.

21. A method of treating a condition selected from the group consisting of depression, mood disorders and schizophrenia in a mammal, the method comprising administering a compound of formula I as defined in claim 1 and a neurotransmitter re-uptake blocker to a mammal in need of such treatment.

22. A process for the preparation of a compound according to formula I in claim 1, wherein $R^{10}$ is OH, and wherein the process comprises the step of reacting a compound of the formula 4

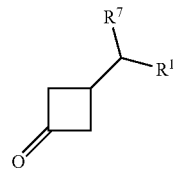

4 wherein $R^1$ is $OR^4$ or $NR^2R^3$, with an aryl halide, wherein the aryl group of the aryl halide has of the formula 20

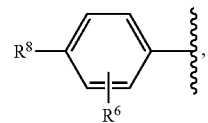

20 in the presence of an organometallic reagent.

* * * * *